(12) United States Patent
Davies et al.

(10) Patent No.: US 7,819,805 B2
(45) Date of Patent: Oct. 26, 2010

(54) SUB-NYQUIST SAMPLING OF ACOUSTIC SIGNALS IN ULTRASOUND IMAGING

(75) Inventors: Timothy J. Davies, Calgary (CA); Richard Evans, Bristol (GB)

(73) Assignee: MGB Investments Limited Partnership, Calgary (CA)

( * ) Notice: Subject to any disclaimer, the term of this patent is extended or adjusted under 35 U.S.C. 154(b) by 1252 days.

(21) Appl. No.: 11/314,139

(22) Filed: Dec. 21, 2005

(65) Prior Publication Data

US 2006/0122506 A1 Jun. 8, 2006

Related U.S. Application Data

(63) Continuation-in-part of application No. 10/945,459, filed on Sep. 20, 2004.

(51) Int. Cl.
*A61B 8/00* (2006.01)
(52) U.S. Cl. .................................................. 600/437
(58) Field of Classification Search ................. 600/437; 702/76; 375/24; 73/602
See application file for complete search history.

(56) References Cited

U.S. PATENT DOCUMENTS

| | | | |
|---|---|---|---|
| 3,895,381 | A | 7/1975 | Kock |
| 4,325,257 | A | 4/1982 | Kino et al. |
| 4,817,434 | A | 4/1989 | Anderson |
| 5,269,309 | A * | 12/1993 | Fort et al. ................ 600/447 |
| 5,299,576 | A | 4/1994 | Shiba |
| 5,345,426 | A | 9/1994 | Lipschutz et al. |
| 5,465,722 | A | 11/1995 | Fort et al. |
| 5,544,659 | A * | 8/1996 | Banjanin ................ 600/455 |
| 5,558,092 | A * | 9/1996 | Unger et al. ............. 600/439 |
| 5,628,320 | A * | 5/1997 | Teo ........................ 600/443 |

(Continued)

FOREIGN PATENT DOCUMENTS

EP    0 812 005 A2    12/1997

(Continued)

OTHER PUBLICATIONS

Morten H. Pedersen, Kim L. Gammelmark, and Jorgen A. Jensen; Preliminary In-Vivo Evaluation of Convex Array Synthetic Aperture Imaging; SPIE 2004.

(Continued)

*Primary Examiner*—Long V Le
*Assistant Examiner*—Vani Gupta
(74) *Attorney, Agent, or Firm*—Oyen Wiggs Green & Mutala LLP

(57) ABSTRACT

Systems and methods are disclosed for improving the resolution and quality of an image formed by signals from an array of receivers. Multiple receivers introduce variations in arrival times that can be less than the period of an operating signal, and also less than the period associated with a sampling operation. Thus, multiple receivers allow sampling of fine features of reflected signals that would be considered beyond the resolution associated with the operating signal. Use of multiple receivers also provides an effective sampling rate that is greater than the sampling rate of an individual receiver. Similar advantages can be obtained using multiple transmitters. Such advantageous features can be used to obtain high resolution images of objects in a medium in applications such as ultrasound imaging. Sub-Nyquist sampling is discussed.

28 Claims, 41 Drawing Sheets

U.S. PATENT DOCUMENTS

| | | | |
|---|---|---|---|
| 5,920,285 | A | 7/1999 | Benjamin |
| 5,969,661 | A | 10/1999 | Benjamin |
| 6,049,509 | A | 4/2000 | Sonneland et al. |
| 6,135,960 | A | 10/2000 | Holmberg |
| 6,363,033 | B1 * | 3/2002 | Cole et al. ................. 367/138 |
| 6,526,163 | B1 | 2/2003 | Halmann et al. |
| 6,719,693 | B2 | 4/2004 | Richard |
| 2005/0131300 | A1 * | 6/2005 | Bakircioglu et al. ........ 600/453 |

FOREIGN PATENT DOCUMENTS

FR     2 851 662 A    8/2004

OTHER PUBLICATIONS

William D. Richard, A Scalable Architecture for Real-Time Synthetic-Focus Imaging, Ultrasonic Imaging 25, pp. 151-161, 2003.

Mark A. Franklin, Abhijit Mahajan and R. Martin Arthur; Parallel Implementations of an Ultrasonic Image Generation Algorithm using MPI; Parallel and Distributed Computing and Systems, pp. 589-596, Nov. 3-6, 1999.

Stephen W. Smith, Henry G. Pavy, Jr., and Olaf T. von Ramm; High-Speed Ultrasound Volumetric Imaging System—Part I: Transducer Design and Beam Steering; IEEE Transactions on Ultrasonics, Ferroelectrics, and Frequency Control, vol. 38, No. 2, pp. 100-108, Mar. 1991.

Peter Cheesman, Bob Kanefsky, Richard Kraft, John Stutz and Robin Hanson; Super-Resolved Surface Reconstruction from Multiple Images; NASA Ames Research Center, Dec. 14, 1994.

Jorgen Arendt Jensen, Ole Holm, Lars Joost Jensen, Henrik Bendsen, Henrik Moller Pedersen, Kent Salomonsen, Johnny Hansen and Svetoslav Nikolov; Experimental Ultrasound System for Real-Time Synthetic Imaging; IEEE International Ultrasonics Symposium, Lake Tahoe, 1999.

Yiming Pi, Hui Long and Shunji Huang; A SAR Parallel Processing Algorithm and its Implementation; Conference Proceedings FIEOS 2002.

Donald Bailey; Image Resolution Improvement from Multiple Images; Massey University, available online at www.poly.edu/Podium/eef2001.cfm, Nov. 2001.

Steven R. Broadstone and R. Martin Arthur; An Approach to Real-Time Reflection Tomography Using the Complete Dataset; pp. 829-831, 1986 Ultrasonics symposium.

Catherine H. Frazier and William D. O'Brien, Jr.; Synthetic Aperture Techniques with a Virtual Source Element; IEEE Transactions on Ultrasonics., vol. 45, No. 1, pp. 196-207, Jan. 1998.

D.K. Peterson and Gordon S. Kino; Real-Time Digital Image Reconstruction; A Description of Imaging Hardware and an Analysis of Quantization Errors; IEEE Transactions on Sonics and Ultrasonics, vol. SU-31, No. 4, pp. 337-351, Jul. 1984.

P.D. Corl, P.M. Grant and G.S. Kino; A Digital Synthetic Focus Acoustic Imaging System for NDE; IEEE Ultrasonics Symposium Proceedings; pp. 263-268, 1978.

Svetoslav I. Nikolov, Jorgen A. Jensen, Remi Dufait and Armin Schoisswohl; Three-Dimensional Real-Time Synthetic Aperture Imaging Using a Rotating Phased Array Transducer; IEEE International Ultrasonics Symposium, 2002.

Mark A. Franklin, Abhijit Mahajan, and R. Martin Arthur; Parallel Implementations of 3D Synthetic-Focus Ultrasonic Image Generation Using MPI; Parallel and Distributed Computing and Systems; vol. I, pp. 239-246, Nov. 6-9, 2000.

Daryl G. Beetner and R. Martin Arthur; Generation of Synthetic-Focus Images from Pulse-Echo Ultrasound Using Difference Equations; IEEE Transactions on Medical imaging, vol. 15, No. 5, pp. 665-672, Oct. 1996.

William. D. Richard and R. Martin Arthur; Real-Time Ultrasonic Scan Conversion via Linear Interpolation of Oversampled Vectors; Ultrasonic Imaging 16, 109-123, 1994.

An Introduction to the Sampling Theorem; National Semiconductor Application Note 236, Jan. 1980.

Samuel H. Gray; The Bleeding Edge of Seismic Imaging; CSEG Recorder, Dec. 2003.

Steven D. Glaser and Mi Kyong Hand; Imaging of Rock Fractures with Low-Frequency Ultrasonic Reflection/Diffraction; American Society for Testing Materials, Geotechnical Testing Journal, vol. 21, No. 4, pp. 317-327, Dec. 1998.

Samuel H. Gray; Nuts and Bolts of Beam Migration; CSEG National Convention 2004.

Mark A. Haun; Douglas L. Jones and William D. O'Brien, Jr; Adaptive Focusing Through Layered Media Using the Geophysical "Time Migration" Concept; Proc. Intl. Ultrasonics Symposium, Munich, Germany, Oct. 8-11, 2002.

Improved Resolution in Infrared Imaging Using Randomly Shifted Images, available online at http://www.ph.tn.tudelft.nl/~cris/MastersProject.html, Nov. 1998.

George Papanicolaou; Interferometric Imaging in Clutter II; ARO/DARPA MURI, Aug. 15, 2003.

Jorgen Arendt Jensen; Ultrasound Imaging and its Modeling; 84 Imaging of Complex Media with Acoustic and Seismic Waves, pp. 135-165, 2002.

Olaf T. Von Ramm, Stephen W. Smith, and Henry G. Pavy, Jr.; High Speed Ultrasound Volumetric Imaging System—Part II: Parallel Processing and Image Display; IEEE Transactions on Ultrasonics, Ferroelectrics, and Frequency Control, vol. 38, No. 2, pp. 109-115, Mar. 1991.

John E. Greivenkamp, Sub-Nyquist interferometry, Dec. 15, 1997, vol. 26, No. 24, Applied Optics, Rochester, New York.

Lyons RG: Understanding Digital Signal Processing, 2nd ed. (2004), Section 2.3.

* cited by examiner

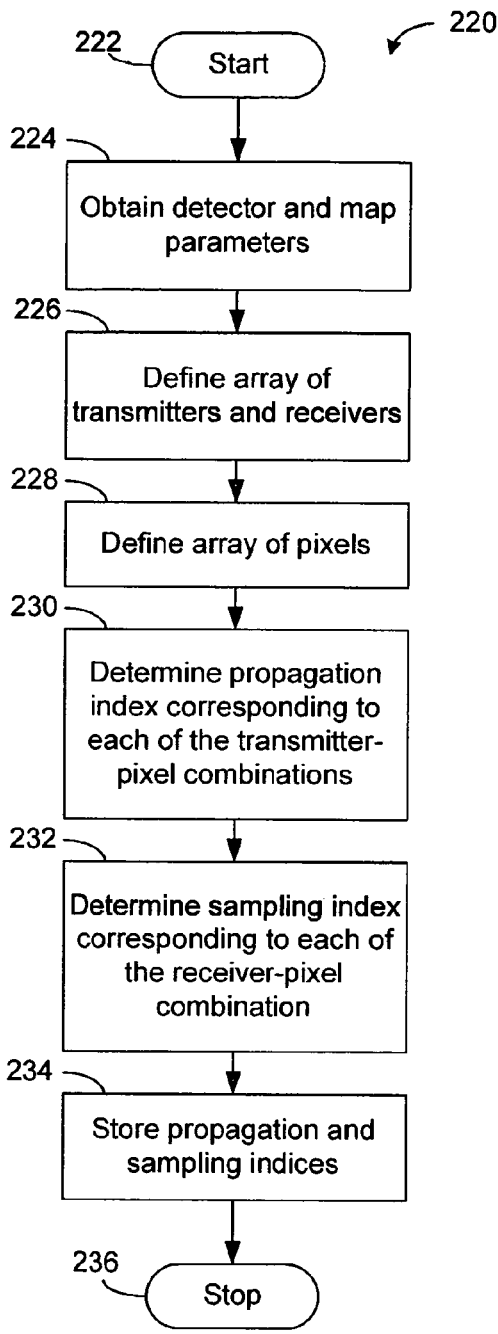
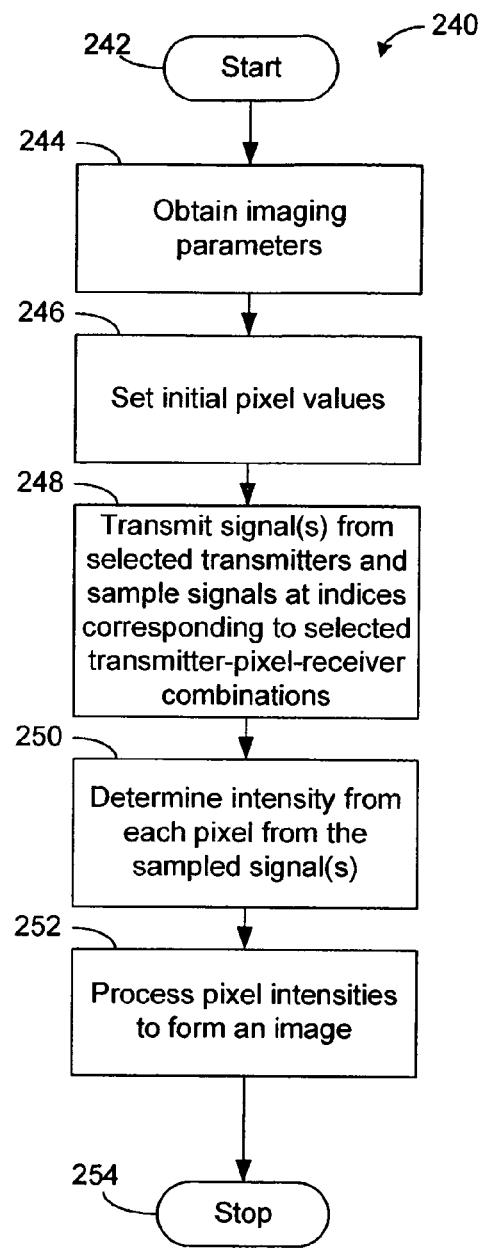
Fig. 7
Fig. 8

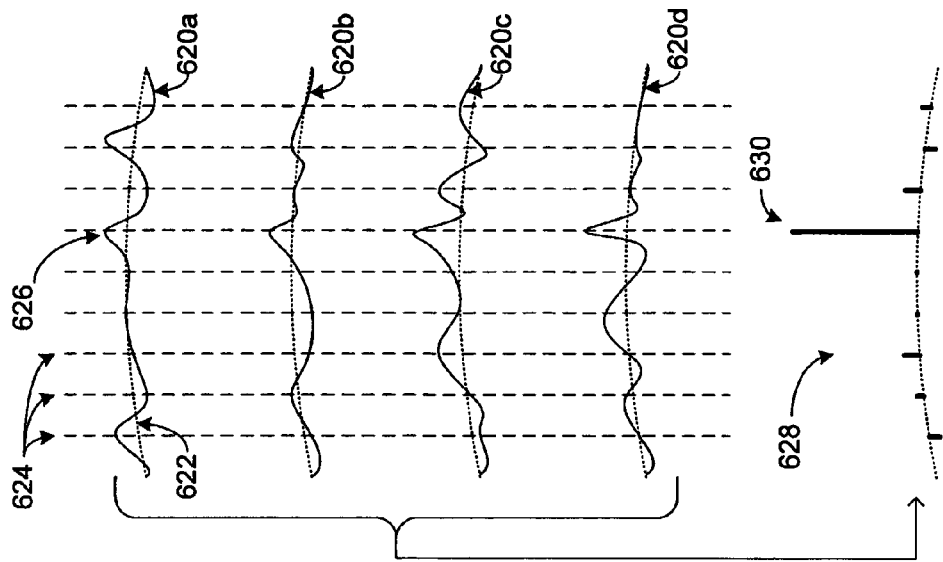
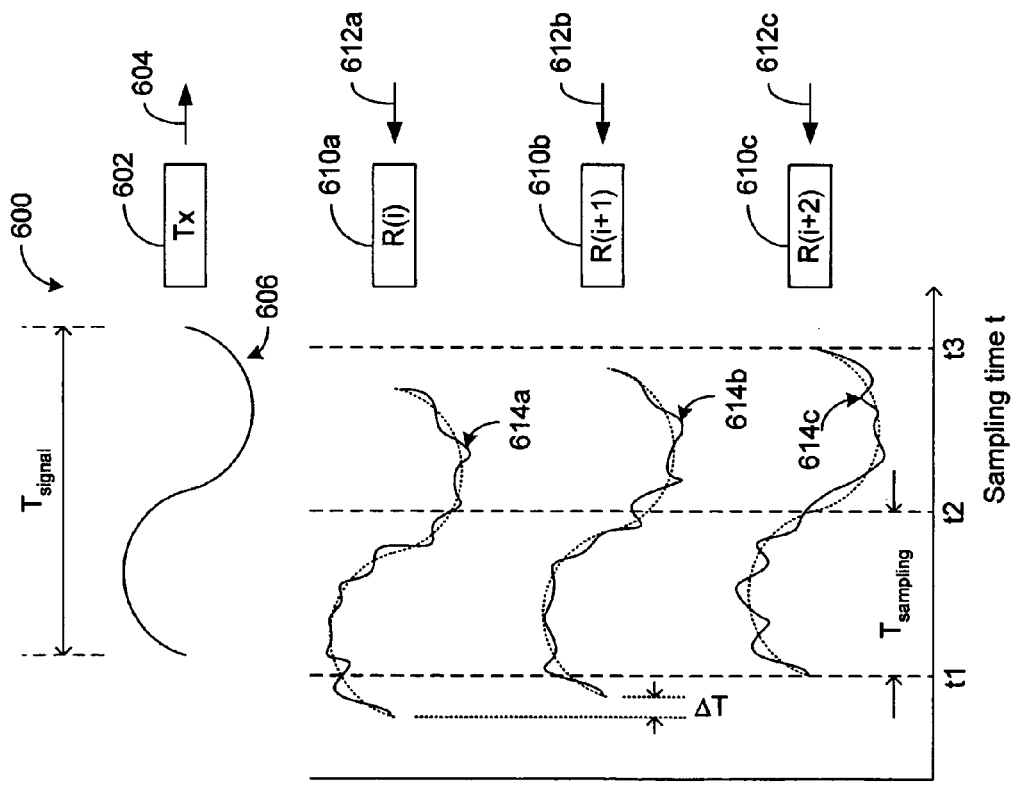
Fig. 17
Fig. 16

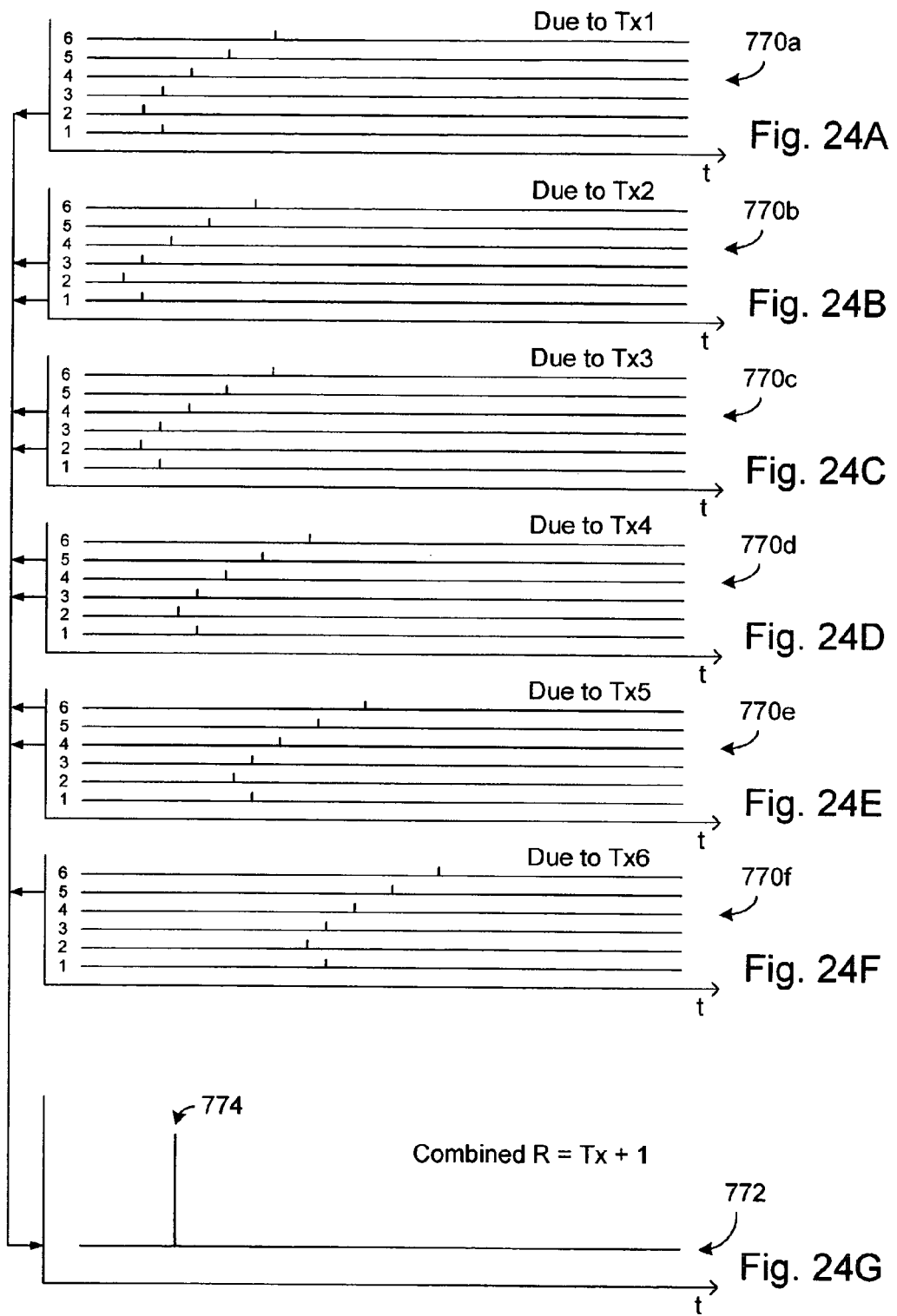

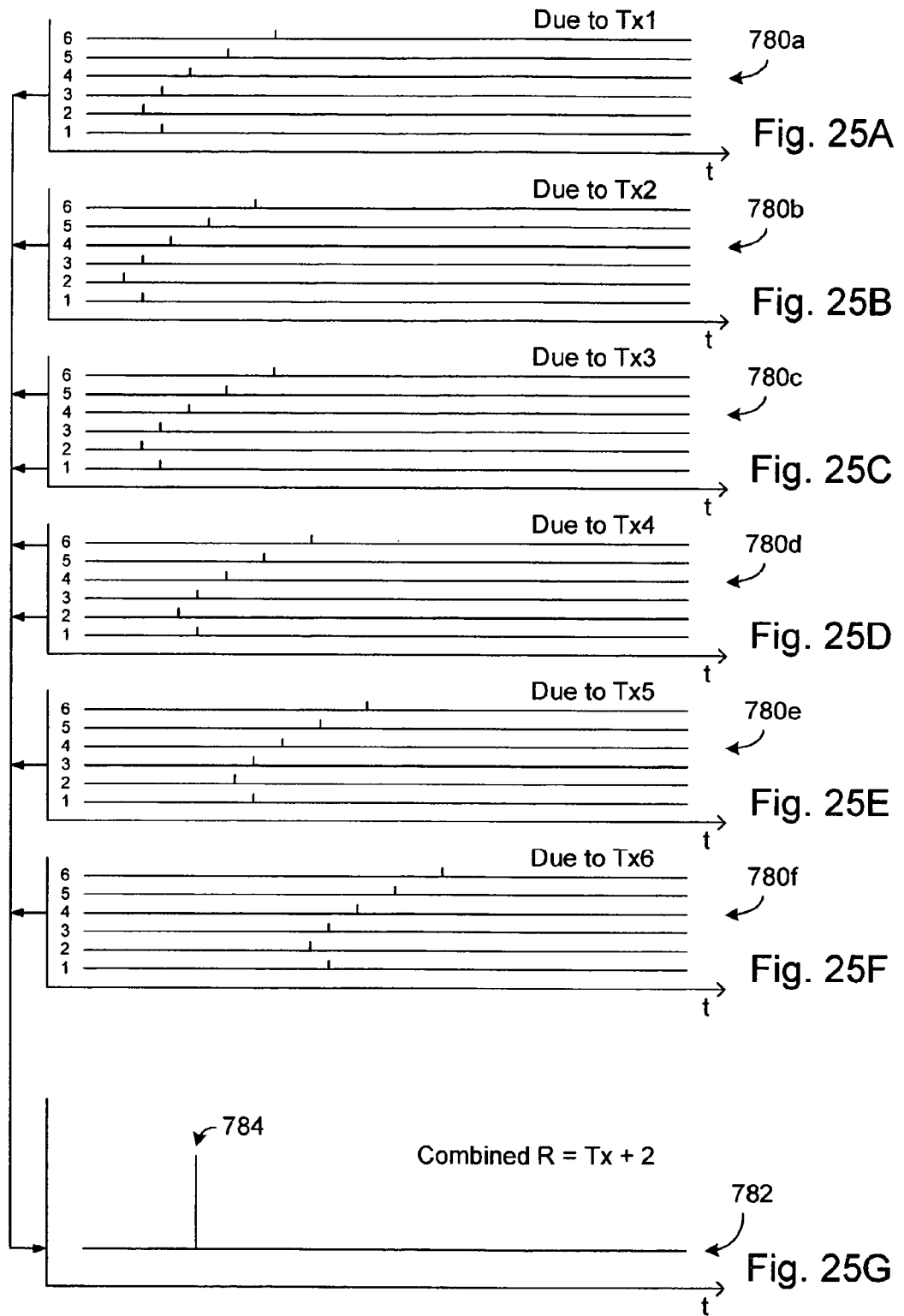

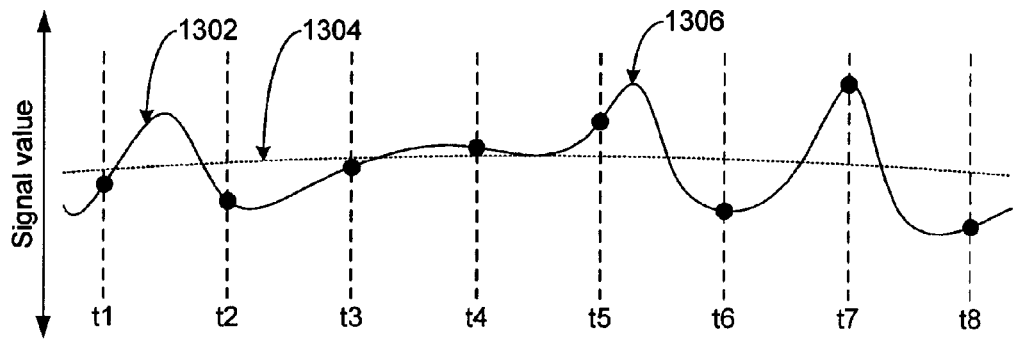
Fig. 37
| Sample time | Signal value | Sampled value |
|---|---|---|
| t1 | S1 | D1 |
| t2 | S2 | D2 |
| t3 | S3 | D3 |
| t4 | S4 | D4 |
| t5 | S5 | D5 |
| t6 | S6 | D6 |
| t7 | S7 | D7 |
| t8 | S8 | D8 |
Fig. 38
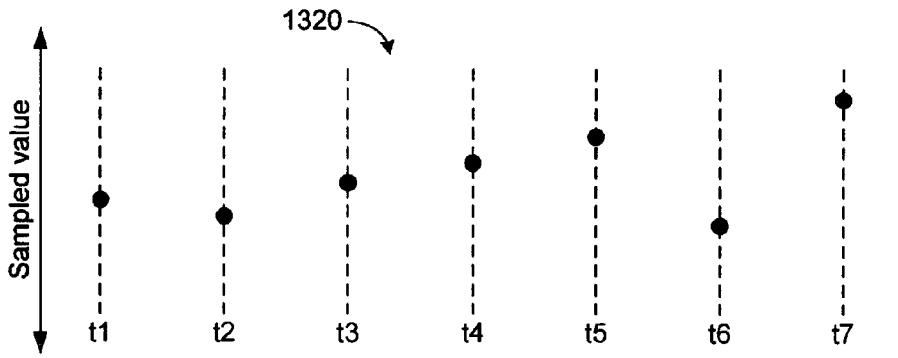
Fig. 39

SUB-NYQUIST SAMPLING OF ACOUSTIC SIGNALS IN ULTRASOUND IMAGING

RELATED APPLICATIONS

This application is a continuation-in-part of, and claims priority to, U.S. patent application Ser. No. 10/945,459, filed Sep. 20, 2004, entitled "SYSTEMS AND METHODS FOR IMPROVED IMAGING," which is hereby incorporated by reference herein in its entirety.

BACKGROUND

1. Field

The present teachings generally relate to the field of imaging using waves and more particularly, to systems and methods for improving the resolution of images obtained by an array of transmitters and receivers.

2. Description of the Related Art

Imaging devices such as ultrasound devices transmit a signal into a medium, and measure reflections from various features in the medium. An image of a given feature can be reconstructed based on quantities such as intensity and frequency of the reflected signal from that feature. To form the image, one needs to somehow determine the relative location of the feature with respect to the imaging device, and in particular, to a location of a receiving element of the device.

Conventional ultrasound devices typically have an array of transmitter-receiver pairs. In operation, each pair only "sees" along a line, commonly referred to as a scanline, that extends from the pair into the medium. With such an assumption, a feature along that scanline can be brought into "focus" by determining the propagation times of the transmitted and reflected signals to and from the feature. A propagation time t can be calculated as t=d/v where v is the velocity of the signal in the medium, and d is the distance of interest (e.g., from the feature to the receiver). The distance d can be determined by dividing the scanline into discrete elements in a predetermined manner, such that the location of each element is known. The velocity v can either be assumed as a constant in the medium, or can be calculated in a manner generally known in the art.

Based on such an operation, one can see that the resolution and quality of the image formed can be limited by the size of the scanline element. Even if the scanline element can be made arbitrarily small, the effective operation of and obtaining an image from the device is subject to the intrinsic resolution of the transmitter-receiver pair, as well as the sampling criteria for yielding a meaningful result.

The intrinsic resolution of a detector can be expressed as depending on the ratio of the operating wavelength of the signal to the effective dimension of the detector (commonly referred to as a Rayleigh or Sparrow criteria). One can change such a resolution of the detector by either changing the wavelength and/or the effective dimension of the detector. For example, reducing the wavelength (increasing the frequency) and/or increasing the effective dimension of the detector can improve the resolution. However, such a change can be accompanied by undesired effects. For example, an increased frequency signal has a smaller penetration depth in ultrasound applications.

Furthermore, an increased operating frequency also forces the minimum sampling frequency. Commonly known as the Nyquist sampling criteria, a signal needs to be sampled at a frequency that is at least approximately twice the frequency of the operating signal to yield a meaningful result.

Because of the foregoing challenges and limitations, there is an ongoing need to improve the manner in which imaging devices are designed and operated.

SUMMARY

The foregoing needs can be addressed by systems and methods for improving the resolution and quality of an image formed by signals from an array of receivers. Multiple receivers introduce variations in arrival times that can be less than the period of an operating signal, and also less than the period associated with a sampling operation. Thus, multiple receivers allow sampling of fine features of reflected signals that would be considered beyond the resolution associated with the operating signal. Use of multiple receivers can also provide an effective sampling rate that is greater than the sampling rate of an individual receiver. Similar advantages can be obtained using multiple transmitters. Such advantageous features can be used to obtain high resolution images of objects in a medium in applications such as ultrasound imaging.

In some embodiments, the present teachings relate to a method of imaging an object in a medium with ultrasound. The method includes transmitting acoustic energy from a transmitter to the object such that the acoustic energy becomes scattered. The method further includes receiving the scattered energy at a plurality of receivers so as to produce respective analog echo signals. The method further includes sampling the analog echo signals at a frequency of F. Prior to sampling, each of the analog echo signals includes substantial spectral frequency components above a frequency of F/2 and including substantial nonnegative spectral frequency components below or at said frequency of F/2. Such sampling produces a respective plurality of digital echo signals. The method further includes combining the plurality of digital echo signals, with each of the digital echo signals being offset by time with respect to another of the digital echo signals, so as to produce a combined digital signal that is selected from a plurality of different combinations of the plurality of digital echo signals. The method further includes producing an image pixel of the object from the combined digital signal.

In one embodiment, the method further includes producing a plurality of image pixels from the plurality of different combinations of the plurality of digital echo signals. In one embodiment, such a method can distinctly depict two objects in the medium that are closer together than approximately 100 micrometers when the acoustic energy has a central peak frequency of approximately 3.5 MHz. In one embodiment, the acoustic energy propagates in the medium with an average velocity of approximately 1540 m/s.

In one embodiment of the method, the substantial spectral frequency components above a frequency of F/2 include a higher frequency having an intensity that is above a predetermined value. Such a predetermined value can have different values, such as 50 dB, 40 dB, 30 dB, 20 dB, 10 dB, or 5 dB less than a maximum intensity of the spectral frequency components of one of the sampled analog echo signals.

In one embodiment of the method, the step of combining the plurality of digital echo signals includes selecting a first digital echo signal associated with a first receiver. The step further includes performing a plurality of time-shift combinations of the first digital echo signal with one or more digital echo signals associated with one or more other receivers about a selected time window of the first signal. Each of the plurality of combinations has a quality value indicative of a quality of the combination.

In one embodiment of the method, the step of combining the plurality of digital echo signals further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of the one of the plurality of combinations.

In one embodiment of the method, the step of combining the plurality of digital echo signals further includes splitting a parent layer into two or more sublayers and performing time-shift combinations on each of the sublayers. The step further includes determining a best quality value for each of the sublayers. The step further includes comparing a best quality value of the parent layer to the best quality value of each of the sublayers. If the best quality value of the parent layer is substantially less than the best quality value of each of the sublayers, then the step further includes continuing to divide each of the sublayers into final sublayers, where each of the best quality values of the final sublayers is less than the best quality value of a parent layer of the final sublayers. In one embodiment, the step further includes assigning a combined digital signal of the parent layer of the final sublayers to the scanline.

In one embodiment of the method, the scanline is divided into a plurality of layers, and determinations of the particular qualities of the combinations are performed successively starting from a layer closest to the receiver.

In one embodiment of the method, the combining of the plurality of digital echo signals substantially negates the effects of aliasing within at least the sampled analog echo signals.

In some embodiments, the present teachings relate to a method of imaging an object with ultrasound. The method includes providing an array of transmitters Tx(i), where i represents a relative positional index that ranges from 1 to N, and where N is greater than or equal to 2. The method further includes providing an array of receivers Rx(i), where each of the receivers Rx(i) is associated with a respective transmitter Tx(i). The method further includes transmitting ultrasound energy from the transmitters to the object such that the ultrasound energy is scattered. The method further includes receiving scattered energy at every receiver Rx(i+j) that was transmitted from transmitter Tx(i), where j represents a relative positional offset from i, and where j is greater than zero. The method further includes generating a first plurality of signals in response to the scattered energies received at every receiver Rx(i+j). The method further includes combining the plurality of signals so as to produce an image of the object.

In one embodiment of the method, the value of j is one. In one embodiment, the method further includes receiving scattered energy at every receiver Rx(i+k) that was transmitted from transmitter Tx(i), where k represents a relative positional offset from i, and where k is greater than zero and is not equal to j. The method further includes generating a second plurality of signals in response to the scattered energies received at every receiver Rx(i+j) and Rx(i+k). The method further includes combining the first and second pluralities of signals so as to produce an image of the object.

In some embodiments, the present teachings relate to an ultrasound imaging apparatus that includes a plurality of transmitters configured to transmit acoustic energy to one or more objects in a medium such that the acoustic energy becomes scattered. The apparatus further includes a plurality of receivers configured to receive the scattered energy and in response produce respective analog echo signals. The apparatus further includes a processor that is configured to facilitate sampling of the analog echo signals at a frequency of F. Prior to sampling, each of the analog echo signals includes substantial spectral frequency components above a frequency of F/2 and includes substantial nonnegative spectral frequency components below or at said frequency of F/2. The sampling of the plurality of analog echo signals produces a respective plurality of digital echo signals. The processor further facilitates combining of the plurality of digital echo signals, with each of the digital echo signals being offset by time with respect to another of the digital echo signals, so as to produce a combined digital signal that is selected from a plurality of different combinations of the plurality of digital echo signals. The processor further facilitates production of an image pixel of the object from the combined digital signal.

In one embodiment of the apparatus, the processor further facilitates production of a plurality of image pixels from the plurality of different combinations of the plurality of digital echo signals. In one embodiment, such an apparatus can distinctly depict two objects in the medium that are closer together than approximately 100 micrometers when the acoustic energy has a central peak frequency of approximately 3.5 MHz. In one embodiment, the acoustic energy propagates in the medium with an average velocity of approximately 1540 m/s.

In one embodiment of the apparatus, the substantial spectral frequency components above a frequency of F/2 include a higher frequency having an intensity that is above a predetermined value. Such a predetermined value can have different values, such as 50 dB, 40 dB, 30 dB, 20 dB, 10 dB, or 5 dB less than a maximum intensity of the spectral frequency components of one of the sampled analog echo signals.

In one embodiment of the apparatus, the processor facilitates combining of the plurality of digital echo signals by a process that selects a first digital echo signal associated with a first receiver. The process further performs a plurality of time-shift combinations of the first digital echo signal with one or more digital echo signals associated with one or more other receivers about a selected time window of the first signal. Each of the plurality of combinations has a quality value indicative of a quality of the combination.

In one embodiment of the apparatus, the process further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of one of the plurality of combinations.

In one embodiment of the apparatus, the process further includes splitting a parent layer into two or more sublayers, and performing time-shift combinations on each of the sublayers. The process further includes determining a best quality value for each of the sublayers. The process further includes comparing a best quality value of the parent layer to the best quality value of each of the sublayers. If the best quality value of the parent layer is substantially less than the best quality value of each of the sublayers, then the process continues to divide each of the sublayers into final sublayers. Each of the best quality values of the final sublayers is less than the best quality value of a parent layer of the final sublayers.

In one embodiment, the scanline is divided into a plurality of layers, and the determinations of the particular qualities of the combinations are performed successively starting from a layer closest to the receiver.

In some embodiments, the present teachings relate to an ultrasound imaging apparatus that includes a transducer assembly having a plurality of transmitting elements and a plurality of receiving elements. The plurality of transmitting elements are configured to transmit ultrasound energy, having a wavelength $\lambda$ corresponding to a central peak frequency of the ultrasound energy, toward a region in a medium. The plurality of receiver elements generate a plurality of signals in response to scattered energy from the region. An aperture size D of the transducer assembly is the maximum distance between any two receiving elements in the transducer assembly. The apparatus further includes a processor configured to sample the plurality of signals to produce a plurality of corresponding digital echo signals. The processor is further configured to combine the plurality of digital echo signals to generate an image having a spatial resolution limit that is equal to or better than $\theta=(0.25)\lambda/D$, where $\theta$ is the minimum resolvable angular separation of two objects in the medium.

In one embodiment of the apparatus, the spatial resolution limit allows resolving of two objects in the medium that are closer together than approximately 100 micrometers when the ultrasound energy has a central peak frequency of approximately 3.5 MHz. In one embodiment, the acoustic energy propagates in the medium with an average velocity of approximately 1540 m/s. In one embodiment, the processor combines the plurality of digital echo signals by a process that includes selecting a first digital echo signal associated with a first receiver, and performing a plurality of time-shift combinations of the first digital echo signal with one or more digital echo signals associated with one or more other receivers about a selected time window of the first signal. Each of the plurality of combinations has a quality value indicative of a quality of the combination.

In one embodiment of the apparatus, the process further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of the one of the plurality of combinations.

In one embodiment of the apparatus, the process further includes splitting a parent layer into two or more sublayers, and performing time-shift combinations on each of the sublayers. The process further includes determining a best quality value for each of the sublayers. The process further includes comparing a best quality value of the parent layer to the best quality value of each of the sublayers. If the best quality value of the parent layer is substantially less than the best quality value of each of the sublayers, then the process further includes continuing to divide each of the sublayers into final sublayers, where each of the best quality values of the final sublayers is less than the best quality value of a parent layer of the final sublayers.

In one embodiment of the apparatus, the process further includes assigning a combined digital signal of the parent layer of the final sublayers to the scanline. In one embodiment, the scanline is divided into a plurality of layers, and determinations of the particular qualities of the combinations are performed successively starting from a layer closest to the receiver.

In some embodiments, the present teachings relate to a method of imaging with ultrasound. The method includes transmitting ultrasound energy, having a wavelength $\lambda$ corresponding to a central peak frequency of the ultrasound energy, from a plurality of transmitters in a transducer assembly into a medium such that the transmission energy is scattered. An aperture size D of the transducer assembly is the maximum distance between any two transmitters in the transducer assembly. The method further includes receiving scattered energies from the medium at a plurality of receivers. The method further includes digitally combining signals generated from the scattered energies so as to produce an image having a spatial resolution limit that is equal to or better than $\theta=(0.25)\lambda/D$, where $\theta$ is the minimum resolvable angular separation of two objects in the medium.

In one embodiment of the method, the spatial resolution limit allows resolving of the two objects in the medium that are closer together than approximately 100 micrometers when the ultrasound energy has a central peak frequency of approximately 3.5 MHz. In one embodiment, the acoustic energy propagates in the medium with an average velocity of approximately 1540 m/s. In one embodiment, the step of digitally combining the signals includes digitally sampling the signals so as to produce a plurality of digital echo signals. The step further includes selecting a first digital echo signal associated with a first receiver. The step further includes performing a plurality of time-shift combinations of the first digital echo signal with one or more digital echo signals associated with one or more other receivers about a selected time window of the first signal. Each of the plurality of combinations has a quality value indicative of a quality of the combination.

In one embodiment of the method, the step of digitally combining the signals further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of the one of the plurality of combinations.

In one embodiment, the method further includes splitting a parent layer into two or more sublayers, and performing time-shift combinations on each of the sublayers. The method further includes determining a best quality value for each of the sublayers. The method further includes comparing a best quality value of the parent layer to the best quality value of each of the sublayers. If the best quality value of the parent layer is substantially less than the best quality value of each of the sublayers, then the method further includes continuing to divide each of the sublayers into final sublayers. Each of the best quality values of the final sublayers is less than the best quality value of a parent layer of the final sublayers. In one embodiment, the method further includes assigning a combined digital signal of the parent layer of the final sublayers to the scanline.

In one embodiment of the method, the scanline is divided into a plurality of layers, and determinations of the particular qualities of the combinations are performed successively starting from a layer closest to the receiver.

In some embodiments, the present teachings relate to a method of replicating information from a waveform energy emanating from an object over time, where the information includes a spectral frequency distribution having frequency components above a frequency F/2. The method includes digitally sampling the waveform energy at a temporal frequency of less than F to obtain sampled data. The method further includes producing a replica of the information from the sampled data, where the replica includes a spectral frequency distribution that substantially matches the spectral frequency distribution in a range above the frequency F/2. The energy is emitted from a plurality of emitters and is reflected from the object.

In one embodiment of the method, the energy is sampled with a plurality of detectors. In one embodiment, the energy is acoustic energy. In one embodiment, the energy is electromagnetic energy.

In some embodiments, the present teachings relate to an ultrasound imaging apparatus having a plurality of transmitters configured to transmit acoustic energy to an object in a medium such that the acoustic energy becomes scattered. The apparatus further includes a plurality of receivers configured to receive the scattered energy and in response produce respective analog echo signals. The apparatus further includes a sampling module configured to sample the analog echo signals at a frequency of F. Prior to sampling, each of the analog echo signals includes substantial spectral frequency components above a frequency of F/2 and includes substantial nonnegative spectral frequency components below or at the frequency of F/2. The sampling of the analog echo signals produces a respective plurality of digital echo signals. The apparatus further includes a combining module configured to combine the plurality of digital echo signals. Each of the digital echo signals is offset by time with respect to another of the digital echo signals, so as to produce a combined digital signal that is selected from a plurality of different combinations of the plurality of digital echo signals. The apparatus further includes an image producing module configured to produce an image pixel of the object from the combined digital signal.

In one embodiment, the image producing module further produces a plurality of image pixels from the plurality of different combinations of the plurality of digital echo signals. In one embodiment, the two objects in the medium are closer together than approximately 100 micrometers when the acoustic energy has a central peak frequency of approximately 3.5 MHz. In one embodiment, the acoustic energy propagates in the medium with an average velocity of approximately 1540 m/s.

In one embodiment, the substantial spectral frequency components above a frequency of F/2 include a higher frequency having an intensity that is above a predetermined value. In one embodiment, the predetermined value is 50 dB less than a maximum intensity of the spectral frequency components of one of the sampled analog echo signals. In one embodiment, the predetermined value is 40 dB less than a maximum intensity of the spectral frequency components of one of the sampled analog echo signals. In one embodiment, the predetermined value is 30 dB less than a maximum intensity of the spectral frequency components of one of the sampled analog echo signals. In one embodiment, the predetermined value is 20 dB less than a maximum intensity of the spectral frequency components of one of the sampled analog echo signals. In one embodiment, the predetermined value is 10 dB less than a maximum intensity of the spectral frequency components of one of the sampled analog echo signals. In one embodiment, the predetermined value is 5 dB less than a maximum intensity of the spectral frequency components of one of the sampled analog echo signals.

In one embodiment, the combining module combines the plurality of digital echo signals by a process that includes selecting a first digital echo signal associated with a first receiver; and performing a plurality of time-shift combinations of the first digital echo signal with one or more digital echo signals associated with one or more other receivers about a selected time window of the first signal. Each of the plurality of combinations has a quality value indicative of a quality of the combination.

In one embodiment, the process performed by the combining module further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of the one of the plurality of combinations.

In one embodiment, the process performed by the combining module further includes splitting a parent layer into two or more sublayers; performing time-shift combinations on each of the sublayers; determining a best quality value for each of the sublayers; comparing a best quality value of the parent layer to the best quality value of each of the sublayers; and if the best quality value of the parent layer is substantially less than the best quality value of each of the sublayers, then continuing to divide each of the sublayers into final sublayers. Each of the best quality values of the final sublayers is less than the best quality value of a parent layer of the final sublayers. In one embodiment, the process further includes assigning a combined digital signal of the parent layer of the final sublayers to the scanline.

In one embodiment, the scanline is divided into a plurality of layers. Determinations of the particular qualities of the combinations are performed successively starting from a layer closest to the receiver.

In one embodiment, the sampling module includes an analog-to-digital converter. In one embodiment, the sampling module includes a processor. In one embodiment, the processor includes a single unit configured to perform one or more processes. In one embodiment, the processor includes a plurality of separate units configured to perform one or more processes.

In one embodiment, the combining module includes a processor. In one embodiment, the processor includes a single unit configured to perform one or more processes. In one embodiment, the processor includes a plurality of separate units configured to perform one or more processes.

In one embodiment, the combining of the plurality of digital echo signals substantially negates the effects of aliasing within at least the sampled analog echo signals.

One embodiment of the present disclosure relates to an ultrasound imaging apparatus that includes a sampling module configured to sample, at a frequency of F, a plurality of analog echo signals received from a respective plurality of receivers. Prior to sampling, each of the analog echo signals includes substantial spectral frequency components above a frequency of F/2 and includes substantial nonnegative spectral frequency components below or at the frequency of F/2. The sampling produces a respective plurality of digital echo signals. The apparatus further includes a combining module configured to combine the plurality of digital echo signals. Each of the digital echo signals is offset by time with respect to another of the digital echo signals, so as to produce a combined digital signal that is selected from a plurality of different combinations of the plurality of digital echo signals.

The apparatus further includes an image-producing module configured to produce an image pixel of an object from the combined digital signal.

One embodiment of the present disclosure relates to an ultrasound imaging apparatus having a plurality of sampling modules. Each sampling module is configured to sample, at a frequency of F, an analog echo signal received from a receiver. Prior to sampling, each of the analog echo signals includes substantial spectral frequency components above a frequency of F/2 and includes substantial nonnegative spectral frequency components below or at the frequency of F/2. The plurality of sampling modules produces a respective plurality of digital echo signals. The apparatus further includes a combining module configured to combine the plurality of digital echo signals. Each of the digital echo signals is offset by time with respect to another of the digital echo signals, so as to produce a combined digital signal that is selected from a plurality of different combinations of the plurality of digital echo signals. The apparatus further includes an image-producing module configured to produce an image pixel of an object from the combined digital signal.

One embodiment of the present disclosure relates to an ultrasound imaging apparatus having a plurality of means for sampling, with each means for sampling configured to sample, at a frequency of F, an analog echo signal received from a receiver. Prior to sampling, each of the analog echo signals includes substantial spectral frequency components above a frequency of F/2 and includes substantial nonnegative spectral frequency components below or at the frequency of F/2. The plurality of means for sampling produces a respective plurality of digital echo signals. The apparatus further includes means for combining the plurality of digital echo signals, with each of the digital echo signals being offset by time with respect to another of the digital echo signals, so as to produce a combined digital signal that is selected from a plurality of different combinations of the plurality of digital echo signals. The apparatus further includes means for producing an image pixel of an object from the combined digital signal.

One embodiment of the present disclosure relates to an ultrasound imaging apparatus having a plurality of transmitters configured to transmit acoustic energy to an object in a medium such that said acoustic energy becomes scattered. The apparatus further includes a plurality of receivers configured to receive said scattered energy and in response produce respective analog echo signals. The apparatus further includes a plurality of sampling modules, with each configured to sample, at a frequency of F, a corresponding one of said plurality of analog echo signals. Prior to sampling, each of said analog echo signals includes substantial spectral frequency components above a frequency of F/2 and includes substantial nonnegative spectral frequency components below or at said frequency of F/2. The plurality of sampling modules produces a respective plurality of digital echo signals. The apparatus further includes a combining module configured to combine said plurality of digital echo signals, with each of said digital echo signals being offset by time with respect to another of said digital echo signals, so as to produce a combined digital signal that is selected from a plurality of different combinations of said plurality of digital echo signals. The apparatus further includes an image producing module configured to produce an image pixel of said object from said combined digital signal.

BRIEF DESCRIPTION OF THE DRAWINGS

FIG. 7 shows a process for obtaining a set of indices separately for transmitters and receivers for a given array of pixels;

FIG. 8 shows a process for using the indices to selectively sample signals obtained by one or more receivers;

FIG. 16 shows how use of multiple receivers can allow sampling of fine perturbation features that are significantly smaller than that of a carrier signal;

FIG. 17 shows how signals from the multiples receivers can be combined to enhance a fine perturbation feature of interest;

FIGS. 24A-F show a simplified depiction of example digitized data trace from the example signal traces of FIGS. 23A and B;

FIG. 24G shows an example of a combination of digitized data associated with receivers that are offset by one from their respective transmitters;

FIGS. 25A-F show a simplified depiction of example digitized data trace from the example signal traces of FIGS. 23A and B;

FIG. 25G shows an example of a combination of digitized data associated with receivers that are offset by two from their respective transmitters;

FIG. 37 shows an example analog echo signal, having one or more relatively fine features, being sampled periodically;

FIG. 38 shows an example table of signal values and the corresponding sampled values at example sampling times of the example analog signal of FIG. 37;

FIG. 39 shows an example plot of the sampled values analog signal of FIG. 37, showing that such sampling can be susceptible to aliasing effects;

These and other aspects, advantages, and novel features of the present teachings will become apparent upon reading the following detailed description and upon reference to the accompanying drawings. In the drawings, similar elements have similar reference numerals.

DETAILED DESCRIPTION OF SOME EMBODIMENTS

Figure 1:
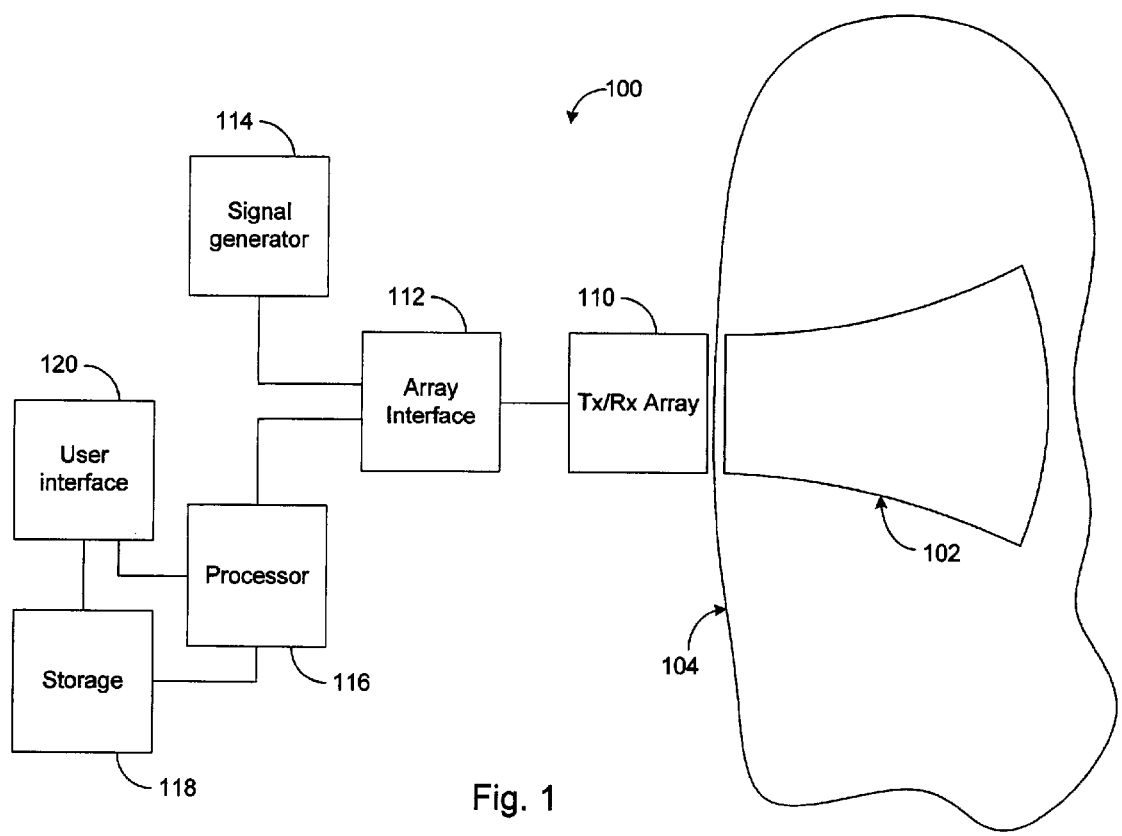
FIG. 1 shows a block diagram of one embodiment of an imaging system that images a defined volume in a medium.

The present teachings generally relate to systems and methods for forming an image of a portion of a medium. FIG. 1 shows a block diagram of one embodiment of an imaging device 100 that includes an array 110 of transducers. A transducer can represent a transmitter or a receiver. As is known, some transducers can operate as transmitters and as receivers. Thus for the purpose of description, a transducer can represent a transmitter, a receiver, or a combination thereof.

As shown in FIG. 1, the imaging device 100 further includes an array interface 112 that facilitates operation of the array 110 of transducers. The array interface 112 may, for example, multiplex and/or demultiplex a plurality of signals to and/or from transmitters and/or receivers. The transducer array 110 via the interface 112 may be supplied with a signal from a signal generator 114. The operation of the interface 112 in providing the signal to the array 110 and/or readout of the received signals from the receivers can be performed by a processor 116. As described below in greater detail, the processor 116 can operate the imaging device 100 in a manner that improves the resolution of the obtained image.

As shown in FIG. 1, the imaging device 100 further includes a storage device 118 that allows retrievable storage of various operating parameters in a manner described below. The imaging device 100 may further include a user interface 120 that provides an output for a user and/or allows a user to control some manner in which the imaging device 100 is operated.

As shown in FIG. 1, the imaging device 100 projects one or more signals into a medium 104 and detects responses of such transmitted signals therefrom. A region 102 that provides measurements in such a manner can be defined as an image volume 102. In the description herein, image volumes are sometimes represented as a two-dimensional plane. In many applications, image "planes" accurately describe the image volume. It will be understood, however, that such representation is in no way intended to limit the scope of the present teachings. It will also be understood that the shape and size of the image volume 102 may vary depending on factors such as the medium, the type of signal being used, and the properties of the imaging device.

It will also be understood that the imaging device, such as the device 100 of FIG. 1, may include both longitudinal-wave and transverse-wave devices. The longitudinal-wave device may include, but is not limited to, ultrasound-based devices, sonar-based devices, or devices that probe underground geological features. The transverse-wave device may include, but is not limited to, devices that operate based on electromagnetic waves such as optical devices or radar-type devices.

Figure 2:
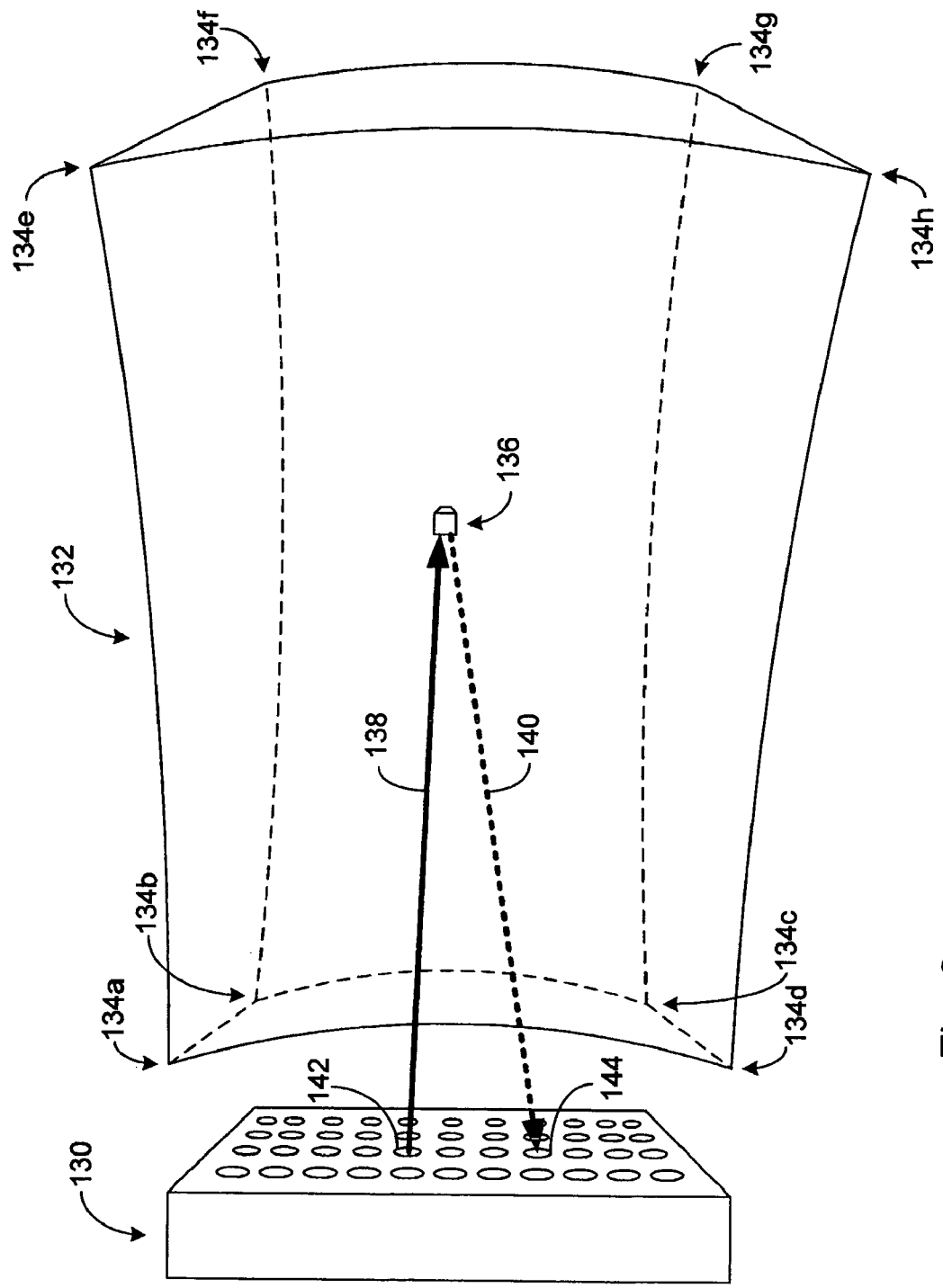
FIG. 2 shows an example transmitter and an example receiver of one embodiment of an array forming an image associated with an example pixel of an image volume.

FIG. 2 shows one embodiment of an example array 130 of transducers that images a volume 132. The example volume 132 can be defined by a plurality of corner locations 134a-h. Within the volume 132 is shown an example elemental volume 136 (also referred to as a pixel and/or voxel herein). A plurality of such pixels 136 make up the volume 132. It will be understood that the terms pixel (picture element) and voxel (volume element) are used interchangeably throughout the description.

In one embodiment, one or more transducers of the array 130 transmit one or more signals into the volume 132 so as to cover each of the pixels therein. A wave impinging on a pixel can be transmitted through the pixel, reflected from the pixel, or any combination thereof. For example, if an object occupies the pixel, that object can cause a partial reflection and a partial transmission. Measurement of the reflected wave or lack of the reflected wave can yield an image of the pixel.

Thus as shown in FIG. 2, the example pixel 136 is depicted as being probed by a transmitted signal 138 from an example transmitter 142. The pixel's response to that signal 138 as measured by an example receiver 144 is indicated by a dashed arrow 140.

One can see that the resolution of an image of the volume depends on the size of the pixels, and the imaging device's ability to resolve such pixels. As described herein, one aspect of the present teachings relates to systems and methods of probing and measuring the pixels in a manner that improves the resolution of images formed therefrom.

Figure 3:
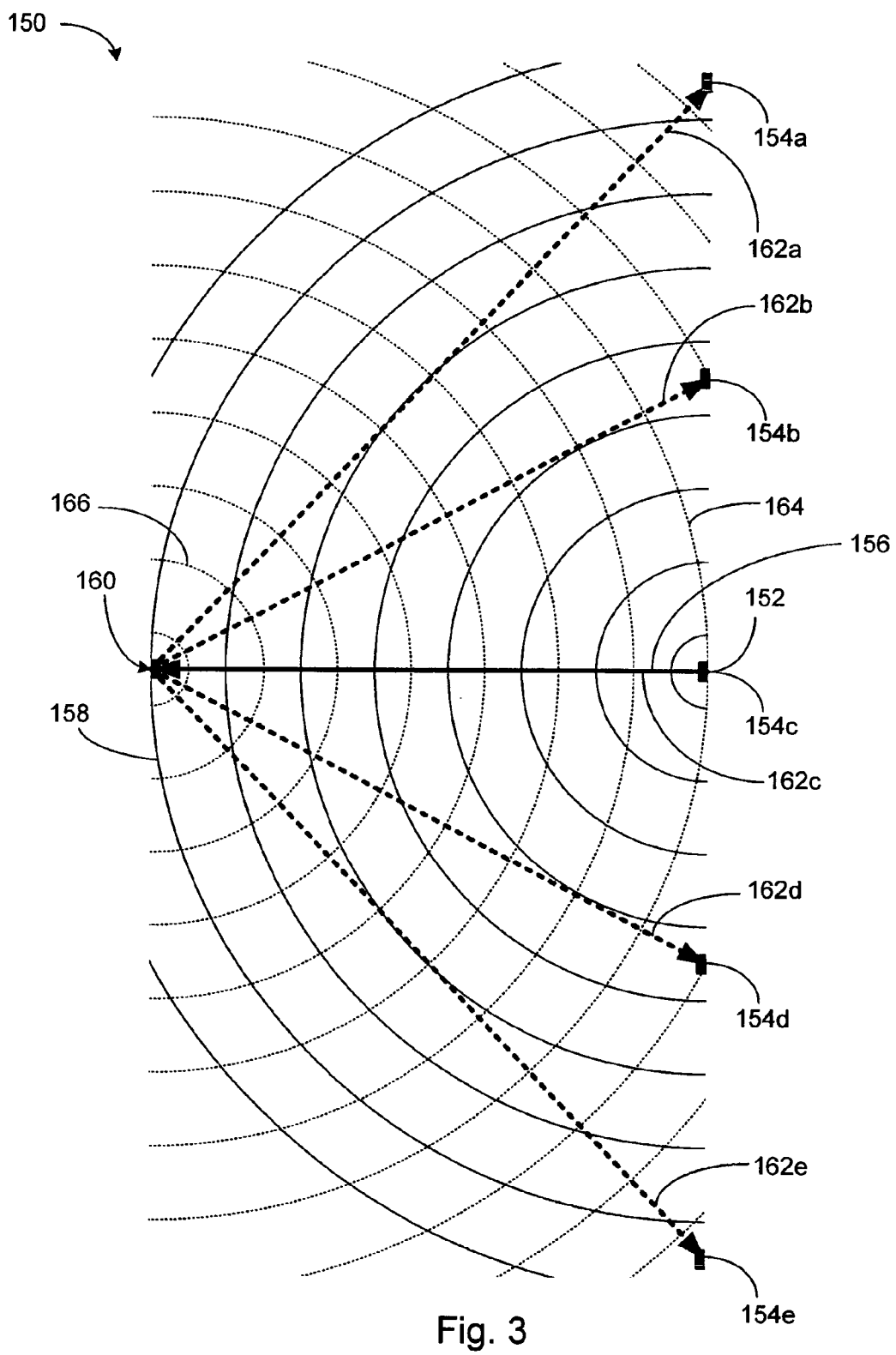
FIG. 3 shows a wave representation of an example array of transducers, where a transmitted signal from one example transducer is shown to reflect from an example target object such that the reflected wave can be detected by a plurality of receivers.

FIG. 3 shows an example wavefront representation 150 of one embodiment of an array of transducers 154a-e probing a target object 160. In the example, the transducers 154 are shown to function as transmitters and receivers, and one receiver 152 is shown to transmit a signal 156. A wavefront 158 impinges on the target 160 and reflects therefrom into a reflected wave 166. A propagated wave 164 is shown to be received first by the transducer 154c. The same wavefront 164 would then be received by other transducers 154a, b, d, e at later times. Rays representing the reflected wave propagation towards the transducers 154a-e are indicated by dashed arrows 162a-e.

By synchronizing and combining the measurements of the reflected wave (example wave 164) by the various transducers, an improved image of the target can be formed. Although FIG. 3 shows a single-transmitter and multiple-receiver operation, it will be understood that any other combinations of transmitters and receivers can be used. As an example, the imaging device can be operated where multiple transmitters transmit multiple signals that are measured by a single receiver. In another example, a plurality of transmitters and a plurality of receivers can be used in various combinations. One aspect of the present teachings relates to performing synchronization and combination of transmitters and/or receivers to improve the performance of the imaging device.

The imaging device can form an image of a portion of a medium containing one or more targets by defining that portion into a plurality of pixels. Thus, the example target of FIG. 3 can occupy one or more pixels. Probing of those pixels, along with other pixels, can yield an image of the target in its medium.

Figure 4:
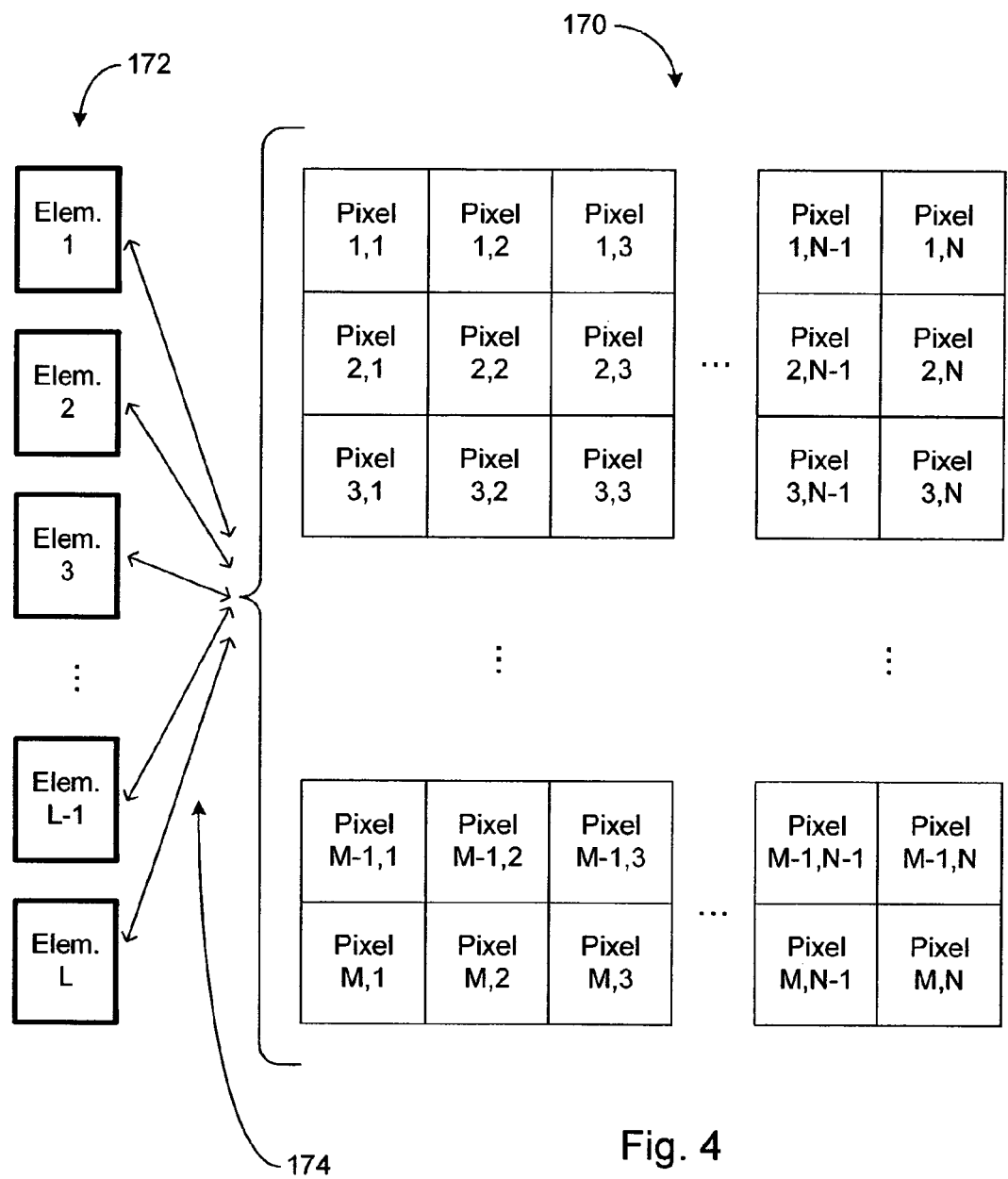
FIG. 4 shows how an image volume can be mapped into a plurality of pixels with respect to a plurality of transducers.

FIG. 4 shows one embodiment of an array of such pixels defined for an image plane 170. The image plane 170 is shown to be divided into an M×N array of pixels. Although FIG. 4 depicts the pixels as squares for the purpose of description, it will be understood that the pixels can be of any definable shape. Furthermore, the overall shape of the image plane 170 need not be rectangular shaped. Moreover, the image plane 170 is referred to as a "plane" for the purpose of description, and is not intended to limit the scope of the present teachings.

Some or all of the pixels of the image plane 170 can be probed by an array 172 of transducer elements. Such probing of the pixels is depicted by a plurality of arrows 174.

FIG. 4 shows L elements arranged along a line to form the array 172. It will be understood that the line arrangement of the transducer elements is for the purpose of description of the image plane 170. The array 172 of transducer elements can be arranged in a two-dimensional array, either in a planar manner or along some curved surface.

Figure 5:
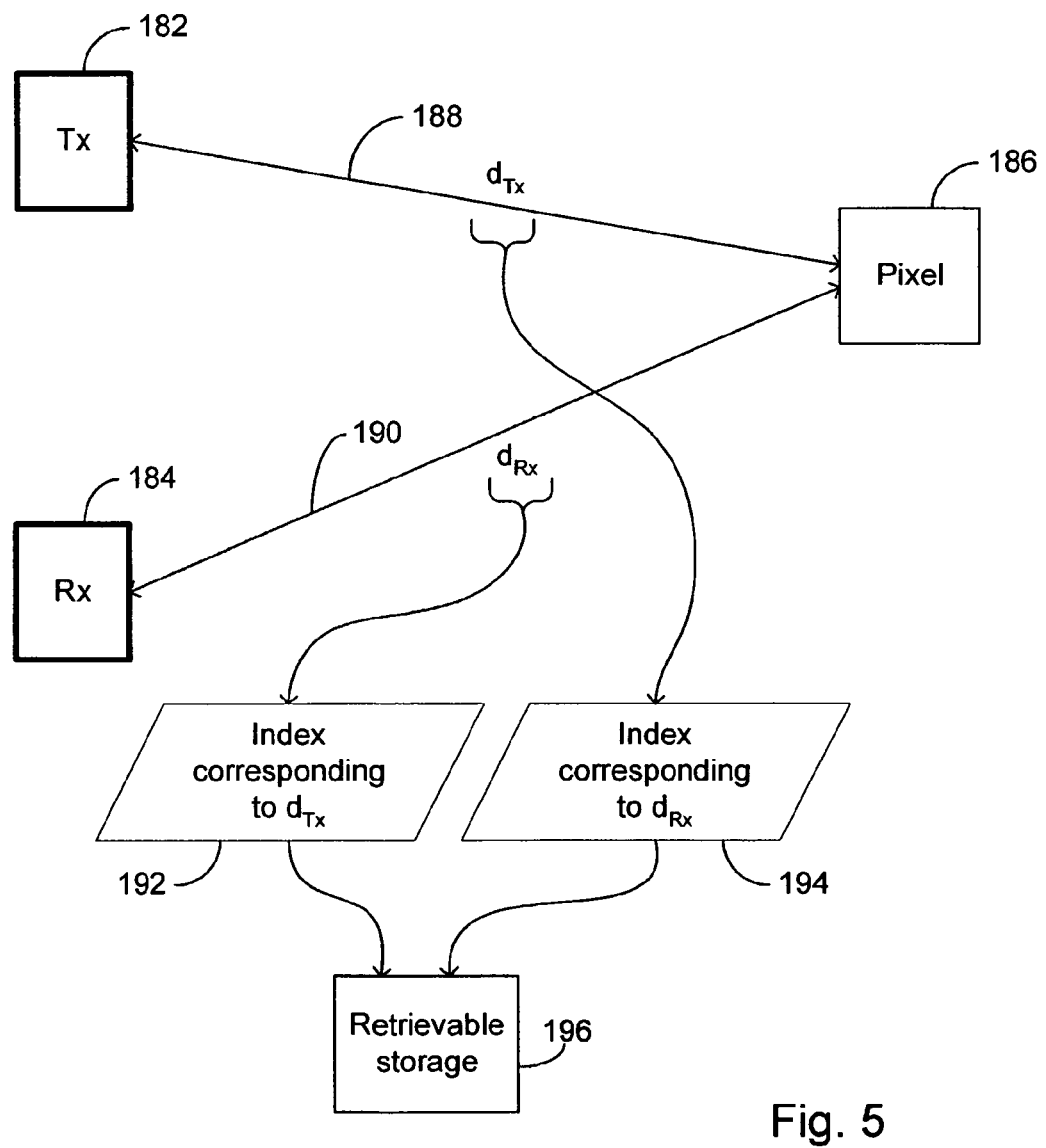
FIG. 5 shows an example of how a position of a pixel relative to a transmitter and a receiver can be stored independently as time-dependent indices based on their respective distances and wave propagation speed.

FIG. 5 shows how a pixel 186 can be associated with a transmitter 182 and with a receiver 184. By performing such associations for all possible transmitter-pixel and receiver-pixel combinations, a spatial and/or temporal alignment set (also referred to as an "alignment set" herein) of an array of pixel is obtained with respect to an array of transmitters and receivers. One aspect of the present teachings relates to mapping the pixels with respect to the transmitters separately from the receiver-pixel mapping. As described below, such a feature provides significant advantages during certain types of high-resolution imaging operations.

As shown in FIG. 5, the pixel 186 is positioned relative to the transmitter 182 by a distance $d_{Tx}$ (as indicated by arrow 188). Similarly, the pixel 186 is positioned relative to the receiver 184 by a distance $d_{Rx}$ (as indicated by arrow 190). The distance $d_{Tx}$ can be used to determine when a signal from the transmitter 182 can be expected to reach the pixel 186. Similarly, the distance $d_{Rx}$ can be used to determine when a possibly-reflected signal from the pixel 186 can be expected to reach the receiver 184. Such expectation information can be used to effectively combine signals associated with different transmitter-pixel and/or receiver-pixel combinations.

The expectation arrival information for the transmitter-pixel combination depends on the distance $d_{Tx}$, and can be represented as some form of an index. Such an index can also account for factors other than the distance that affect the arrival of the signal. As an example, electronic circuitry associated with the transmitter may cause the signal to be transmitted after a delay from some start time. Thus, an index data 194 corresponding to the distance $d_{Tx}$ may also include such other factors.

Similarly, the expectation arrival information for the receiver-pixel combination depends on the distance $d_{Rx}$, and can be represented as some form of an index. Such an index can also account for factors other than the distance that affect the arrival of the signal. As an example, a readout process associated with the receiver may cause the signal to be sampled after a delay from the time when the signal impinges on the receiver. Thus, an index data 192 corresponding to the distance $d_{Rx}$ may also include such other factors.

As shown in FIG. 5, the indices 194 and 192 can be stored independently in a retrievable storage 196. A collection of such indices for all possible transmitter-pixel and receiver-pixel combinations then defines the alignment set of the array of pixels.

Figure 6:
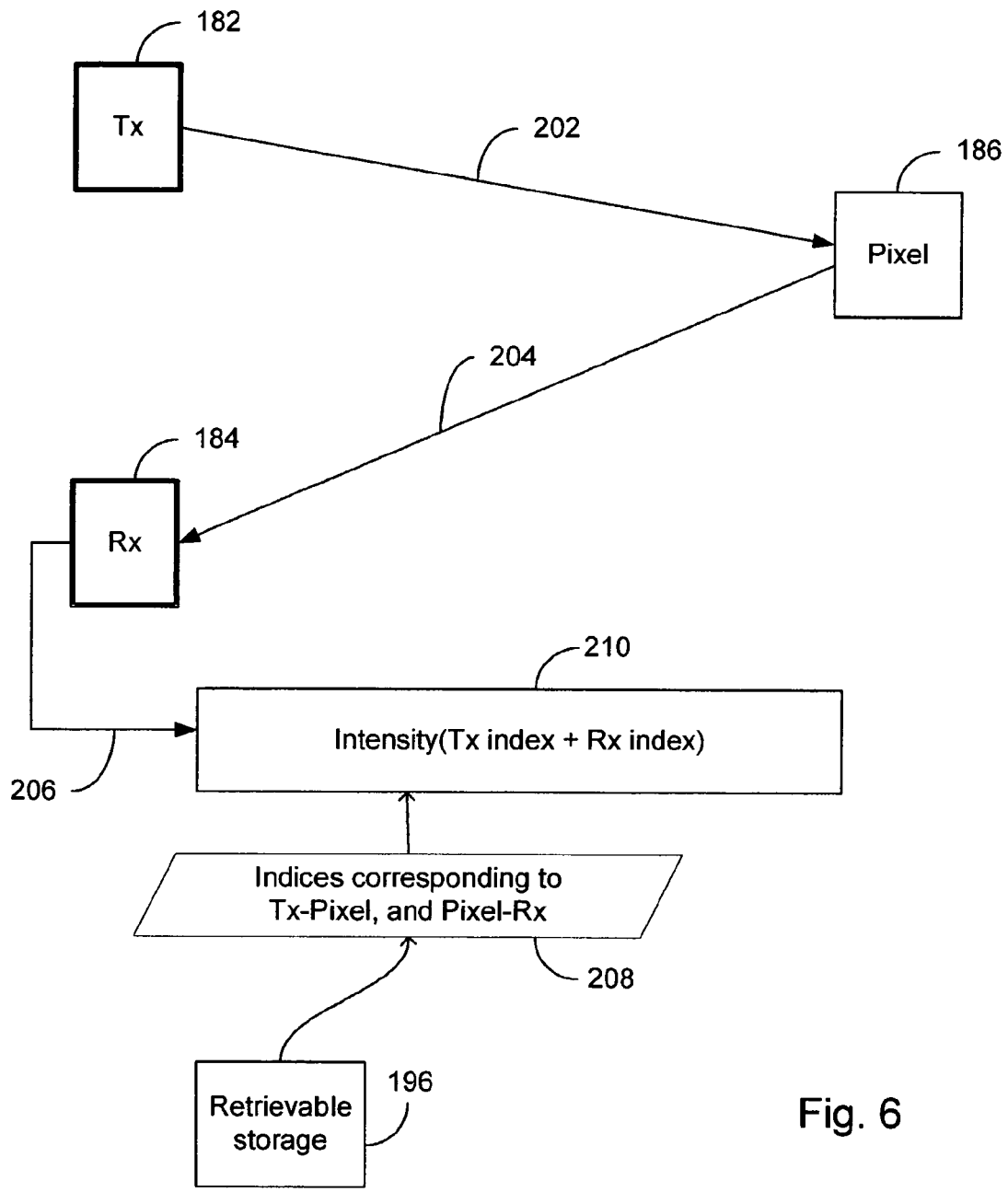
FIG. 6 shows how the indices can be used to selectively sample a signal received by a receiver.

FIG. 6 shows how an alignment set for the pixel 186 can be used to obtain a selectively sampled signal 210 from an output 206 of the receiver 184. A transmitted signal from the transmitter 182 propagating towards the pixel 186 is depicted as an arrow 202. The signal 202 may or may not experience reflection from the pixel 186. Thus, an arrow 204 represents how a reflected signal would propagate from the pixel 186 to the receiver 184.

As further shown in FIG. 6, data 208 having the transmitter-pixel and receiver-pixel indices can be retrieved from the storage 196, and be used to selectively sample the output 206 of the receiver 184. In one embodiment, such selectively sampled signal 210 is obtained by sampling the output 206 at an index corresponding to the sum of the transmitter-pixel and receiver-pixel indices. Some possible forms of the indices are described below in greater detail.

FIGS. 7 and 8 show processes that perform the index determination and subsequent use, respectively, for an array of transducers. A process 220 determines the indices for a given pixel array with respect to a given array of transducers. The process 220 begins at a start state 222, and in a process block 224, the process 220 obtains detector and map parameters. Detector parameters may include the number of transmitters and the number of receivers. Map parameters may include the number of pixels, the desired size of the pixels, and the arrangement of the pixels.

The process 220 in a process block 226 defines the array of transmitters and receivers. In one embodiment, each transmitter and each receiver are defined in terms of their positions relative to a chosen coordinate system. In an embodiment where transmitter and receiver function are performed by a common transducer, the array definition only needs to be performed for the transducer array. An example array definition is described below in greater detail.

The process 220 in a process block 228 defines the array of pixels as determined by the map parameters. In one embodiment, each pixel is defined in terms of its position relative to the transmitter/receiver array. An example array definition is described below in greater detail.

The process 220 in a process block 230 determines a propagation index corresponding to each transmitter-pixel combination. An example propagation index determination is described below in greater detail.

The process 220 in a process block 232 determines a sampling index corresponding to each receiver-pixel combination. An example sampling index determination is described below in greater detail.

The process 220 in a process block 234 stores the propagation indices and the sampling indices. An example storage of the indices is described below in greater detail. The process 220 ends at a stop state 236. In one embodiment, the alignment set generation process 220 is performed once for a given transducer array and a given pixel array, and does not need to be re-done during the imaging operation.

As shown in FIG. 8, an image generation process 240 determines the measured signals associated with some or all of the pixels using the previously determined alignment set for the transducer-pixel configuration. The process 240 begins at a start state 242, and in a process block 244, the process 240 obtains imaging parameters. In one embodiment, the imaging parameters include the number of transmitters and receivers, and alignment sets for transmitter-pixel and receiver-pixel combinations.

The process 240 in a process block 246 sets initial values for each of the pixels being evaluated. An example of such initialization is described below in greater detail.

The process 240 in a process block 248 transmits signal(s) into the pixel array, and samples signal(s) at indices corresponding to selected transmitter-pixel-receiver combinations. An example of selected transmitting and sampling is described below in greater detail.

The process 240 in a process block 250 determines the intensity of each of the selected pixels from the sampled signal(s). An example of such intensity determination is described below in greater detail.

The process 240 in a process block 252 processes the pixel intensities to form an image associated with the pixel array. The process 240 ends at a stop state 254.

Figure 9:
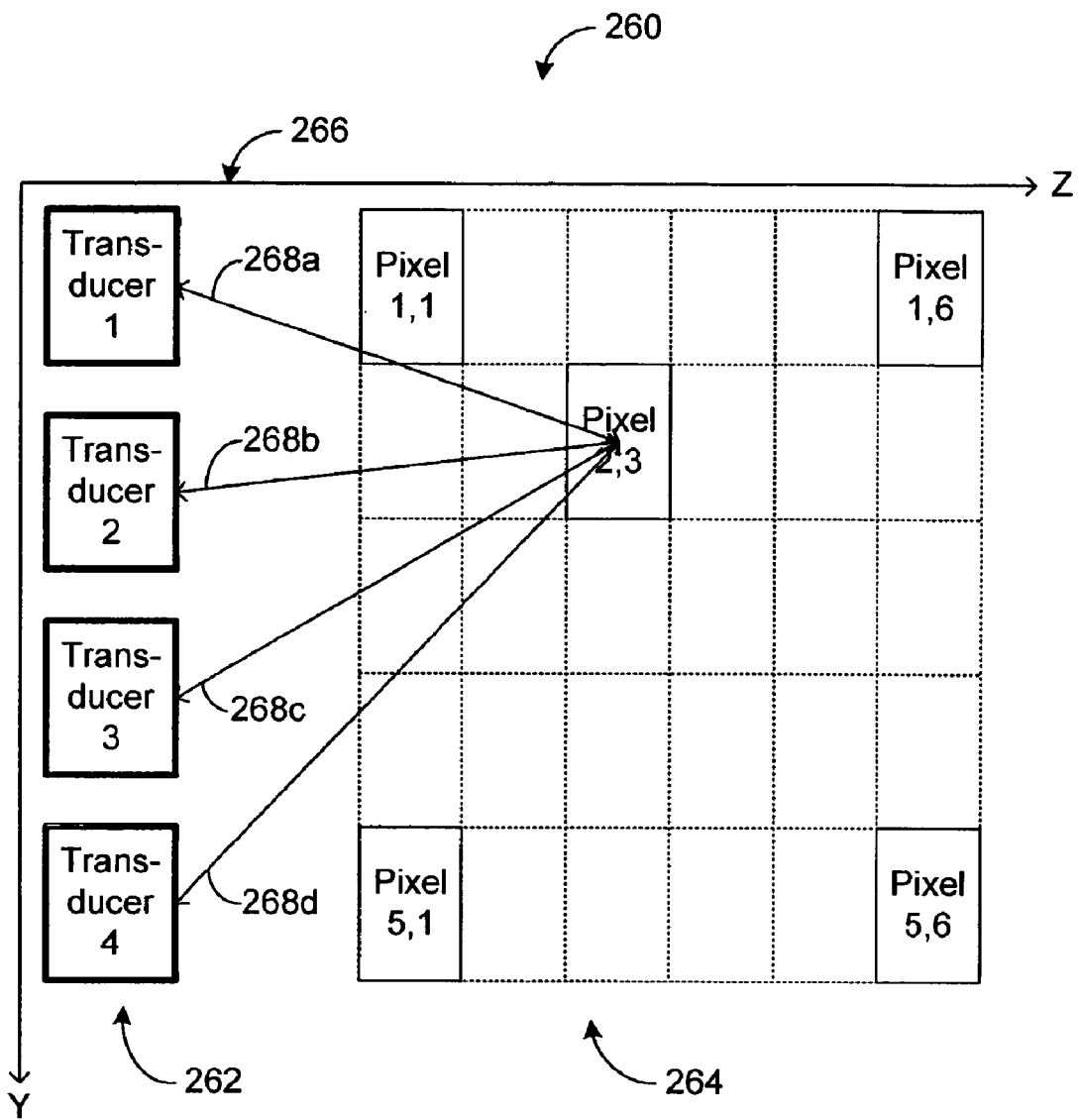
FIG. 9 shows an example of how a pixel array can be defined with respect to a transducer array, thereby allowing determination of distances between transducers and pixels.
Figure 10:
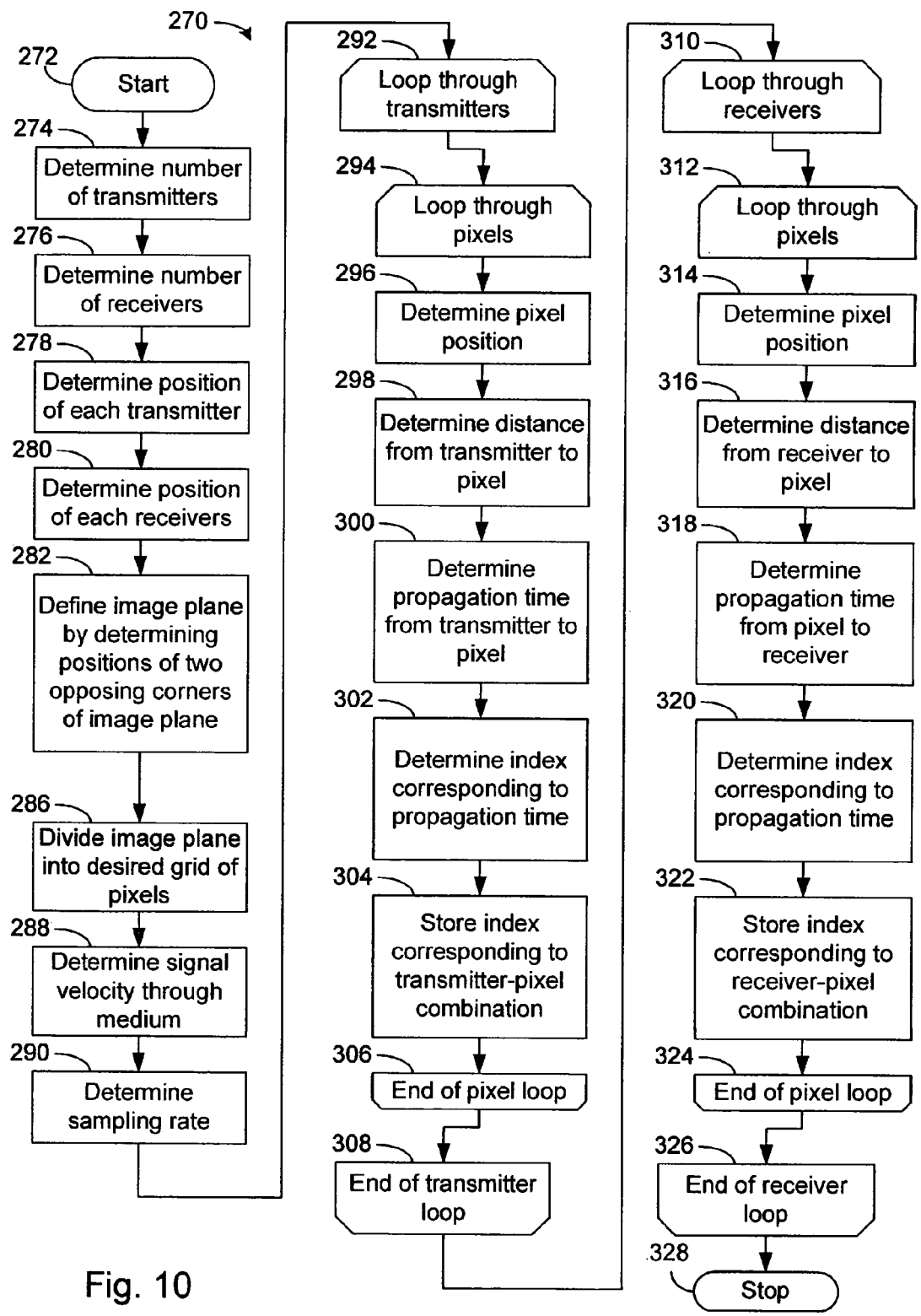
FIG. 10 shows a process that separately determines indices corresponding to various position-defined transmitter-pixel and receiver-pixel combinations.
Figure 11:
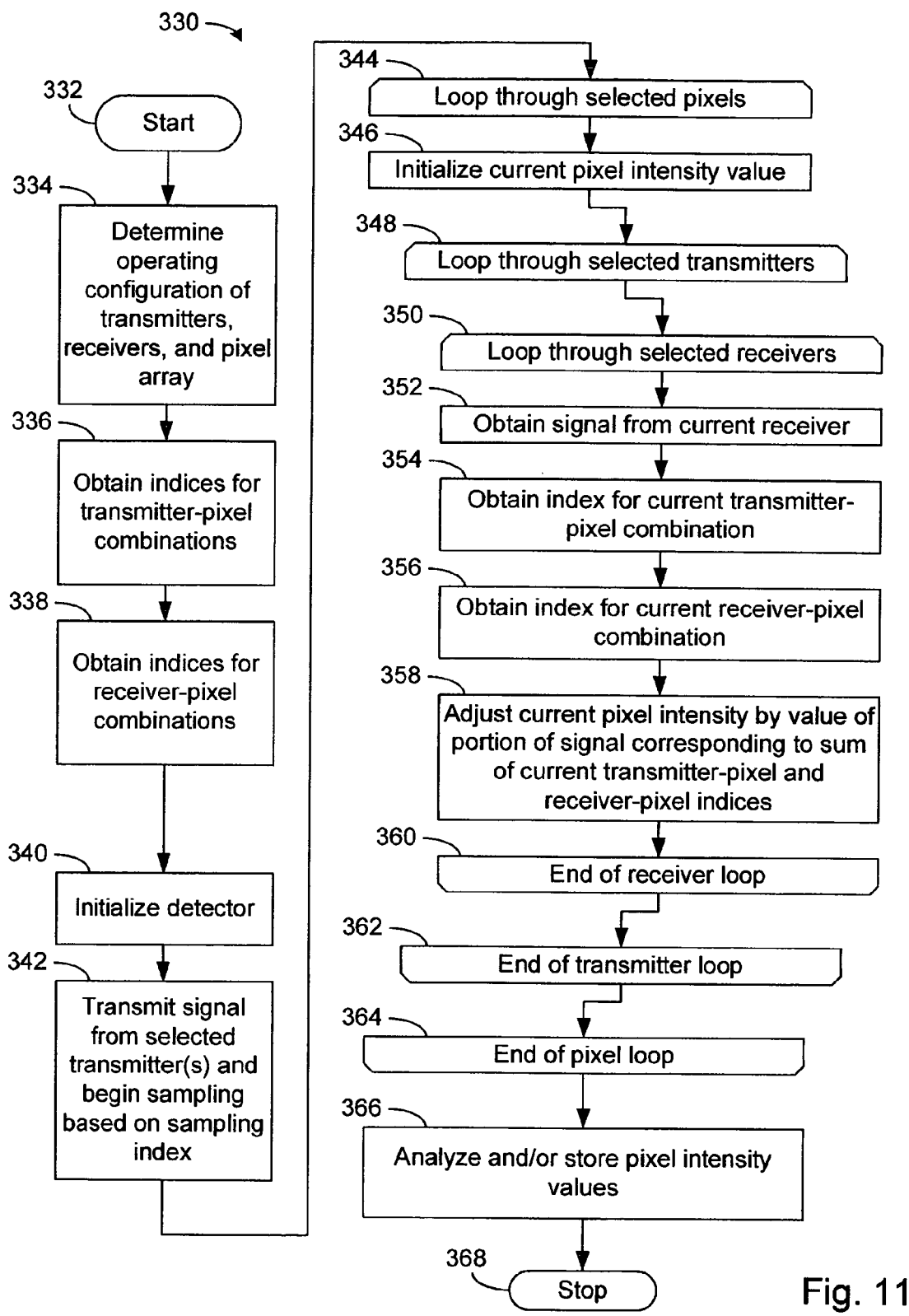
FIG. 11 shows a process that uses the transmitter-pixel and receiver-pixel indices to image selected pixels using selected transmitters and selected receivers.

FIGS. 9-11 now show a more specific manner in which the transducer and pixel arrays can be configured, and how mapping and imaging operations can be performed on such a configuration. FIG. 9 shows an example configuration 260 of array of pixels 264 relative to an array of transducers 262. It will be understood that use of four example transducers 262 is for descriptive purposes only, and is in no way intended to limit the scope of the present teachings. Similarly, the use of a 5×6 array of pixels 264 is for descriptive purposes only, and is in no way intended to limit the scope of the present teachings.

In one embodiment, the positions of the transducers 262 are defined with respect to a coordinate system 266. Although a Cartesian coordinate system is used, it will be understood that any coordinate system can be used for such definition.

In one embodiment, the array of pixels 264 is formed by dividing up an image plane into a grid (5×6 in the example) of pixel regions. One way to define such a grid is to define the positions of a set of opposing corner pixels—for example, (1,1) and (5,6), or (1,6) and (5,1), with respect to the coordinate system 266. Then, one can specify number of rows (5 in this example) and columns (6 in this example). Such a definition of the grid provides sufficient information to define the size and position of each of the pixels. One can see that the pixel grid can be defined in any number of ways. Thus, the example method disclosed herein is not intended to limit the scope of the present teachings.

Once the pixel grid 264 is established with respect to the chosen coordinate system 266, each pixel's position can be referenced to each transducer. As an example, the pixel (2,3) is shown to be referenced to transducers 1 to 4 as denoted by arrows 268a-d. Such relative positions of the pixel to the transducers can be used to obtain the transmission indices and sampling indices.

One way of obtaining an index associated with a given transducer-pixel combination is to first determine the distance between the transducer and the pixel. Such determination can be achieved by simple geometry calculation based on the chosen coordinate system. As an example, if the coordinates of the pixel and the transducer can be represented by $(x_p, y_p, z_p)$ and $(x_t, y_t, z_t)$ respectively, the distance d between the two points can be calculated as square root of the quantity $(x_t-x_p)^2 + (y_t-y_p)^2 + (z_t-z_p)^2$.

The distance d obtained in the foregoing manner can then be used to determine the propagation time t between the transducer and the pixel as t=d/v where v is the magnitude of the propagation velocity of the signal of interest in the medium. For sampling purposes, the propagation time t can further be expressed as a sample number $i_{sample}$ for situations where the received signal is sampled at a sampling rate. In one embodiment, the sample number can be represented as $i_{sample}$=(t) (sample rate). As previously described, the actual time between some "start" time and sampling time may include time(s) in addition to the propagation times. Such additional time, if any, can also be represented as a sample-rate-based quantity, and added to the propagation times.

From the foregoing description of the sample number determination, one can see that similar information can be obtained in any number of ways. Thus, it will be understood that any number of other methods, or variations of the disclosed method, can be used to obtain and store the indices associated with the transmitter-pixel and receiver-pixel combinations.

FIG. 10 now shows one implementation of a detailed process 270 for determining an alignment set for a given pixel array with respect to given transmitter and receiver arrays. The process 270 begins at a start state 272, and in a process block 274, the number of transmitters is determined. In a process block 276, the number of receivers is determined. In a process block 278, the position of each transmitter is determined. In a process block 280, the position of each receiver is determined.

In a process block 282, the process 270 defines an image plane by determining positions of two opposing corners of the image plane. In a process block 286, the image plane is divided into a grid defined by desired numbers of rows and columns of pixels.

In a process block 288, the process 270 determines the signal's velocity through the medium being imaged. In a process block 290, the sampling rate is determined.

As shown by a loop 292 (with end-loop 308), the process 270 loops through the transmitters. For each transmitter, the process 270 loops through the pixels (loop 294, with end-loop 306). Thus for each combination of the transmitter and pixel, the process 270 determines the pixel position in a process block 296. In a process block 298, the distance between the transmitter and the pixel is determined. In a process block 300, propagation time between the transmitter and the pixel is determined based on the distance and signal velocity (t=d/v). In a process block 302, an index corresponding to the propagation time is determined. In one embodiment, the index can be represented as a product of the propagation time and the sampling rate of the imaging device. In a process block 304, the index corresponding to the transmitter-pixel combination is saved for later retrieval and use. The loops 294 and 292 end at loop-ends 306 and 308 respectively.

As shown by a loop 310 (with end-loop 326), the process 270 loops through the receivers. For each receiver, the process 270 loops through the pixels (loop 312, with end-loop 324). Thus for each combination of the receiver and pixel, the process 270 determines the pixel position in a process block 314. In a process block 316, the distance between the receiver and the pixel is determined. In a process block 318, propagation time between the pixel and the receiver is determined based on the distance and signal velocity (t=d/v). In a process block 320, an index corresponding to the propagation time is determined. In one embodiment, the index can be represented as a product of the propagation time and the sampling rate of the imaging device. In a process block 322, the index corresponding to the receiver-pixel combination is saved for later retrieval and use. The loops 312 and 310 end at loop ends 324 and 326 respectively. The process 270 ends at a stop state 328.

As previously described, the alignment set generation, such as that of the process 270, is generally performed once and does not need to be repeated during subsequent imaging operations. The stored indices corresponding to the transmitter-pixel and receiver-pixel combinations allow such subsequent improved-resolution imaging operations to be performed in an efficient manner.

FIG. 11 now shows one implementation of a detailed process 330 for performing an imaging operation utilizing the alignment set obtained previously. The process 330 begins at a start state 332, and in a process block 334 an operating configuration of transmitters, receivers, and pixels is determined. In one embodiment, such an operating configuration defines the numbers and positions of the transmitters, receivers, and pixels in a manner similar to that used for the alignment set determination process. As such, one or more operating configurations can be stored, and one configuration can be either selected by a user or be used as a default.

In a process block 336, the process 330 obtains a set of indices corresponding to the transmitter-pixel combinations of the operating configuration. In a process block 338, a set of indices corresponding to the receiver-pixel combinations of the operating configuration is obtained.

In a process block 340, the process 330 initializes the imaging detector. In one embodiment, such initialization includes initializing the values of the pixel intensities.

In a process block 342, the process 330 transmits a signal from selected transmitter(s) and begins sampling for return signals from the pixel array using selected receiver(s). In one embodiment, a sampling "start" is issued at some predetermined time about the time when the signal leaves the transmitter. Referencing the samplings from such a common start time allows correlated sampling of all the transmitter-pixel-receiver combinations. By having separate sets of transmitter-pixel and receiver-pixel indices, such correlated sampling, as well as other variations of operation of the imager, can be performed more efficiently.

In one embodiment, the process 330 measures the pixel array by sampling signals associated with each of the transmitter-pixel-receiver combinations. One way to cover all the combinations is to perform nested loops for the transmitters, pixels, and receivers. Thus, the process 330 is shown to loop through the selected pixels (loop 344, end-loop 364). For each pixel in the pixel loop 344, its intensity value is initialized in a process block 346. For each initialized pixel, the process 330 loops through the selected transmitters (loop 348, end-loop 362). For each pixel-transmitter combination, the process 330 loops through the selected receivers (loop 350, end-loop 360). Thus for each pixel-transmitter-receiver combination of the nested loops 344, 348, 350, the process 330 in a process block 352 obtains a signal from the current receiver. In a process block 354, the index for the current transmitter-pixel combination is obtained. In a process block 356, the index for the current receiver-pixel combination is obtained. In a process block 358, the pixel intensity is adjusted by a value of the receiver signal corresponding to the sum of current transmitter-pixel and receiver-pixel indices.

As shown in FIG. 11, pixel intensity values obtained in the foregoing manner can be further analyzed or stored (for later analysis) in a process block 366. The process 330 ends in a stop state 368.

Figure 12:
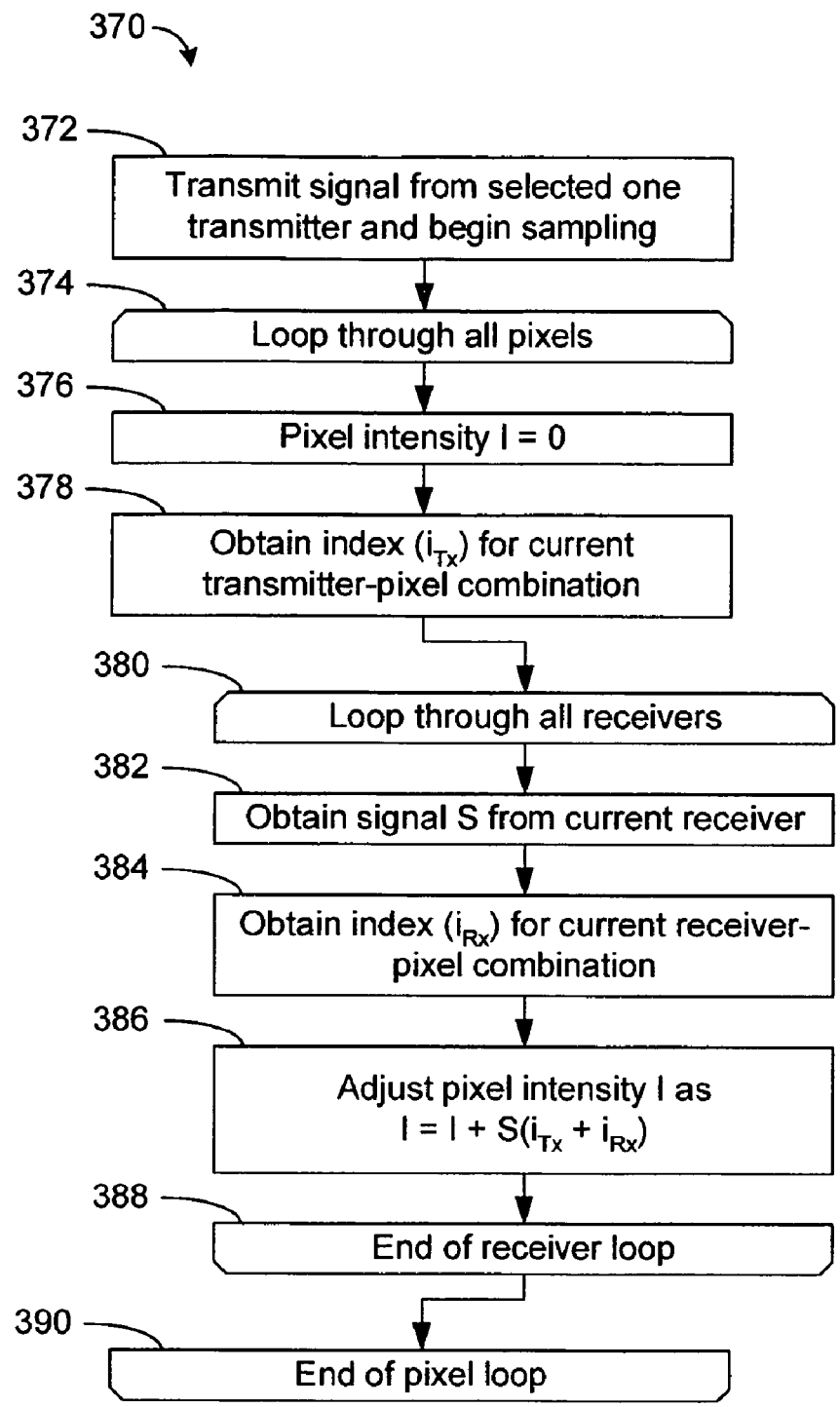
FIG. 12 shows an example process that images a pixel array by transmitting from one selected transmitter and sampling from substantially all receivers.
Figure 13:
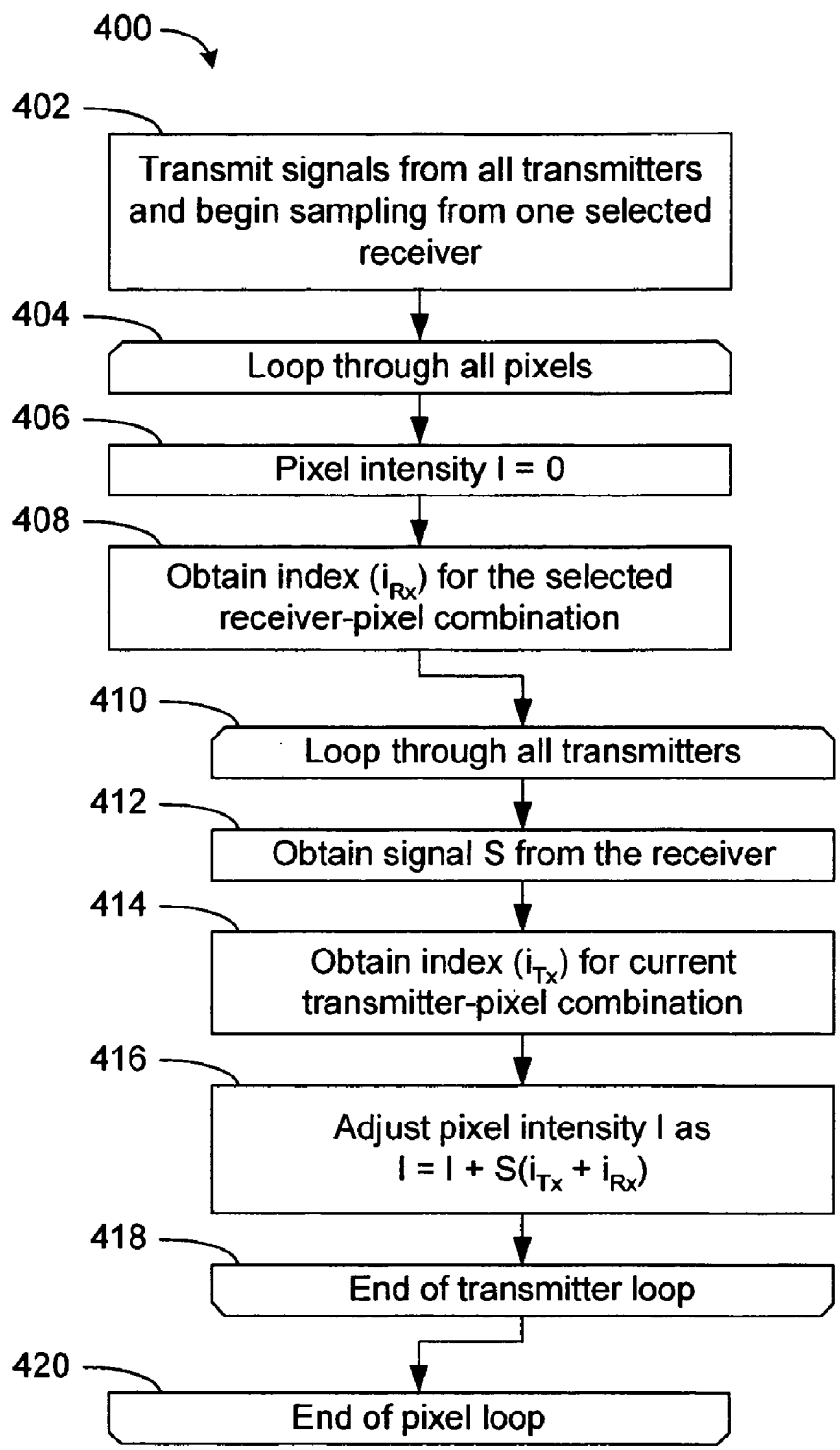
FIG. 13 shows an example process that images a pixel array by transmitting from substantially all transmitters and sampling from one receiver.

FIGS. 12 and 13 now show two specific examples of using selected transmitter(s) and selected receiver(s) to obtain an improved image quality. In FIG. 12 an example process 370 is shown where a single selected transmitter and a plurality of selected receivers are used. In FIG. 13, an example process 400 is shown where a plurality of selected transmitters and a single selected receiver are used.

As shown in FIG. 12, the example process 370 in a process block 372 transmits a signal from a selected transmitter and begins sampling. Such a beginning of sampling can be at a predetermined time relative to the time when the transmitted signal begin propagating from the transmitter. The process 370 then loops through all of the pixels in a loop 374 (with an end-loop 390). For each pixel, the process 370 sets that pixel's initial value to zero in a process block 376. Also for that pixel, the process 370 obtains the index $i_{Tx}$ for the current transmitter-pixel combination in a process block 378.

For the current pixel, the process 370 then loops over all of the selected receivers in a loop 380 (with an end-loop 388). The process 370 in a process block 382 obtains a signal S from the current receiver. In a process block 384, the index for the current pixel-receiver combination $i_{Rx}$ is obtained. In a process block 386, the current pixel's intensity value is adjusted as $I=I+S(i_{Tx}+i_{Rx})$.

As shown in FIG. 13, the example process 400 in a process block 402 transmits signals from all of the selected transmitters, and begins sampling from one selected receiver. Transmitting of the signals from the selected transmitters can be either simultaneous or in a predetermined sequence. In embodiments where the number of selected transmitters is relatively small, the signals may be transmitted substantially simultaneously, and the sampling may be able to temporally distinguish the transmitter-pixel-receiver combinations. In embodiments where the number of selected transmitters is relatively large, the signals being transmitted simultaneously may not allow effective selective sampling of the transmitter-pixel-receiver combinations.

In embodiments where the signals are transmitted simultaneously, beginning of sampling can be at a predetermined time relative to the time when the transmitted signals begin propagating from the transmitters. In embodiments where the signals are transmitted in some sequence, beginning of sampling can be defined in a variety of ways. One way is to have a common start time, and account for the different transmit times for different transmitters as adjustments to the transmitter-pixel combination indices.

The process 400 then loops through all of the pixels in a loop 404 (with an end-loop 420). For each pixel, the process 400 sets that pixel's initial value to zero in a process block 406. Also for that pixel, the process 400 obtains the index $i_{Rx}$ for the current receiver-pixel combination in a process block 408.

For the current pixel, the process 400 then loops over all of the selected transmitters in a loop 410 (with an end-loop 418). The process 400 in a process block 412 obtains a signal S from the receiver. In a process block 414, the index for the current transmitter-receiver combination $i_{Tx}$ is obtained. In a process block 416, the current pixel's intensity value is adjusted as $I=I+S(i_{Tx}+i_{Rx})$.

Figure 14:
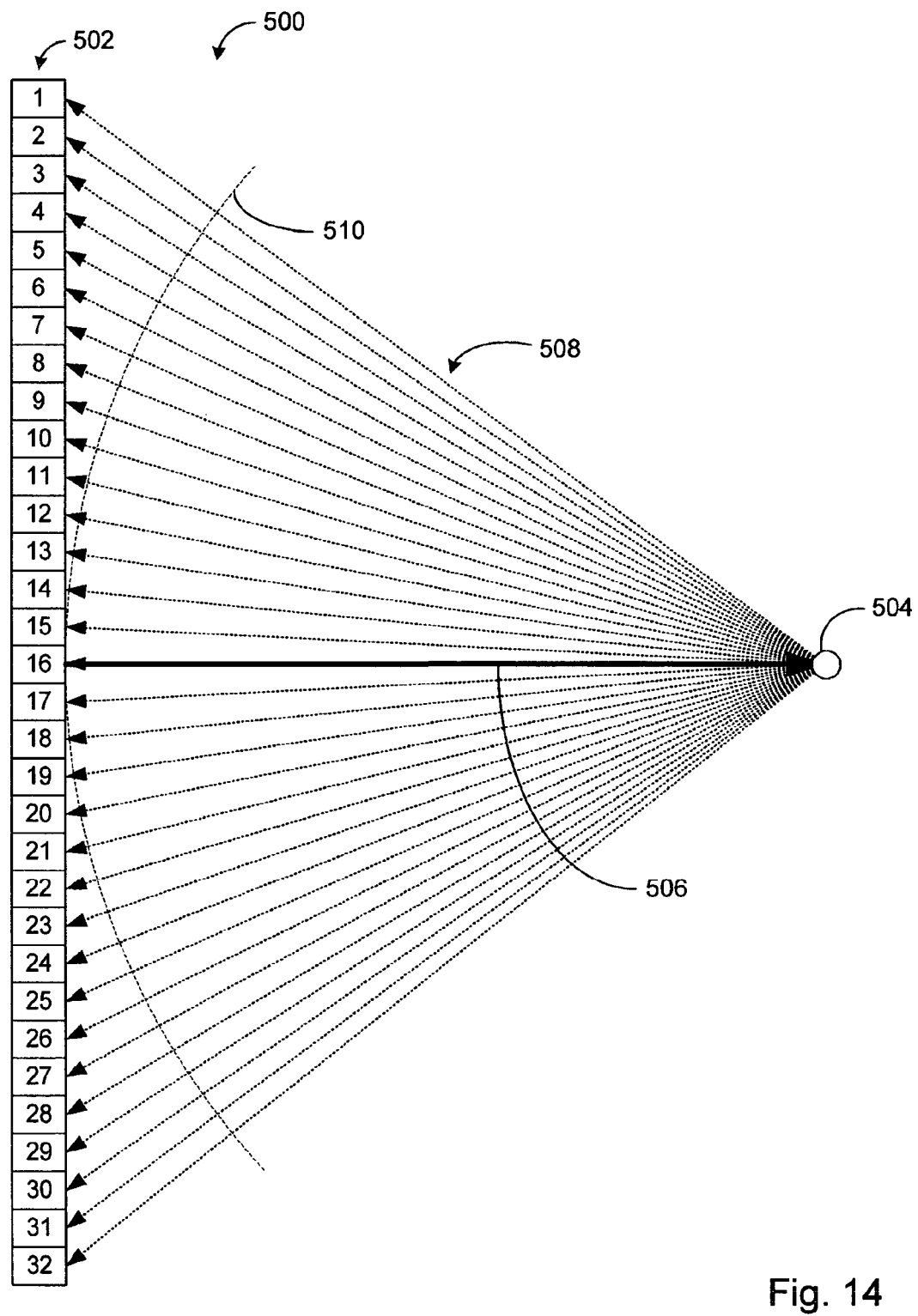
FIG. 14 shows a ray representation of an example 32-transducer device being operated in a single-transmitter/all-receiver mode.

In one embodiment as shown in FIG. 14, an imaging device includes 32 elements. In particular, FIG. 14 shows a ray representation 500 of the embodiment where one transmitter (transmitter 16) transmits a signal 506 to an object 504, resulting in a reflected wave 510 that is detected by 32 receivers (1 to 32). The reflected wave 510 propagating to the receivers 502 is represented by reflected rays 508, and the intersection of the wavefront 510 with the rays 508 represent the in-phase portions of the rays 508.

For the example embodiment 500, the index $i_{Tx}$ representative of the transmitted signal 506 is common to all of the sampling indices used by the 32 receivers. For the particular example where the object is located at the mid-level of the array 502, the reflected wave 510 reaches receiver 16 first. Thus, the sampling index associated with the pixel where the object 504 is located would have a value that causes the signal from receiver 16 to be sampled first. Thereafter, signals from receivers 15 and 17 would be sampled, followed by 14 and 18, etc. Signal from receiver 32 would be the last to be sampled at a time corresponding to the extra propagation distance of the wavefront 510.

Figure 15:
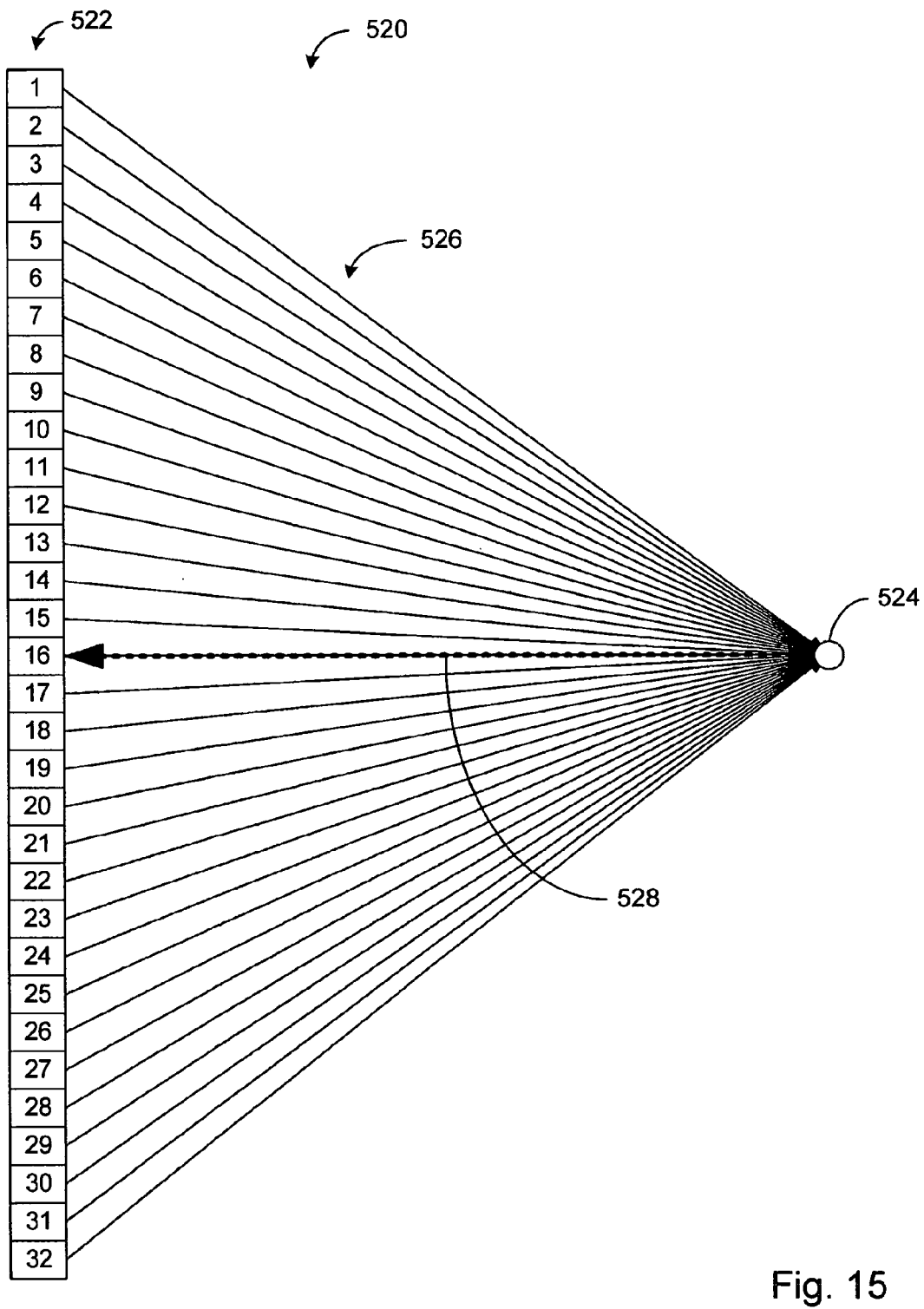
FIG. 15 shows a ray representation of the 32-transducer device being operated in an all-transmitter/single-receiver mode.

In one embodiment as shown in FIG. 15, an imaging device includes 32 elements. In particular, FIG. 15 shows a ray representation 520 of the embodiment where all 32 transmitters transmit signals 526 to an object 524, resulting in a reflected signal 528 that is detected by receiver 16. For the example embodiment 520, the index $i_{Rx}$ representative of the reflected signal 528 is common to all of the sampling indices associated with the 32 receivers.

For the particular example where the object is located at the mid-level of the array 502, the transmitted signal from transmitter 16 reaches the object 524 first (assuming that all signals are transmitted simultaneously). Thus, the sampling index associated with the pixel where the object 524 is located would have a value that causes the first sampled signal to be associated with transmitter 16. The next set of sampled signals would be associated with transmitters 15 and 17, and so on. The last set of sampled signals would be associated with transmitter 32.

As previously described in reference to FIG. 13, the plurality of signals can be transmitted from the transmitters in different ways. Sequenced transmission of signals from the plurality of transmitters can temporally separate the arrivals of the signals at the object 524, as well as reflected signals at the receiver thereafter. One way to sequence the signal transmission is to begin transmission at the transmitter 16, followed at a predetermined time by transmission at transmitters 15 and 17, etc. Such a sequence of transmission can increase the temporal separation of the samplings associated with the array of receivers 522.

FIG. 16 now shows how sampling by a plurality of transducers can yield an effective sampling rate that is greater than a sampling rate associated with each of the transducers. In an example operating configuration 600, a transmitter 602 is depicted as transmitting a transmission energy 604 into a medium (not shown) in response to a transmission signal 606. The transmission signal 606 is depicted as a periodic signal; but such a characteristic is not a requirement. The transmission signal 606 can be of any waveform having some time-characterizable feature. For example, if the transmission signal 606 is a single pulse, it may be characterized by it temporal width.

The example operating configuration 600 further includes a plurality of receivers 610 that receive respective reflection energies 612. In response to the reflection energies 612, the receivers 610 output respective signals 614 that are sampled. In this example, the plurality of receivers 610 are shown to be sampled simultaneously for the purpose of description. It will be understood that simultaneous sampling of the receiver signals is not a requirement.

Also for the purpose of description, the common sampling is shown to have a period $T_{sampling}$ that is approximately half of the transmission signal period $T_{signal}$. As such, the sampling frequency in such a situation is approximately twice the transmission signal frequency. In general, a sampling frequency should be at least twice the frequency of a signal being analyzed to be able to characterize that signal; and the "twice" lower limit is often referred to as the Nyquist limit.

As shown in FIG. 16, the example signals 614 output by the receivers 610 are shown to have an underlying "carrier" signal structure (dotted curve superimposed for descriptive purpose) that can have a similar structure as the transmission signal 606. The signals 614 can include a plurality of perturbations about the carrier signal structure. Such perturbations can be the result of the interaction of the transmission signal 606 with some feature of interest in the medium, or due to background noise. Whatever the cause may be, such perturbations may have (and are depicted as having) sub-wavelength feature sizes when compared to the carrier signal structure or the sampling period. As such, sampling of an individual receiver alone will not be able to resolve the fine-feature structures associated with noises or legitimate signals.

When a plurality of receivers are used, the receivers may be arranged so that reflected energies arrive at the receivers at different times. Such arrival time differences can be caused by differences in propagation times due to the pathlength differences and/or velocity differences caused by medium anisotropy. In FIG. 16, such an arrival difference is depicted as $\Delta T$ for the receivers 610a and 610b. For a given pair of receivers, the arrival difference $\Delta T$ can be made substantially smaller than the sampling period $T_{sampling}$ or the transmission signal period $T_{signal}$.

With an array of receivers, successive arrival differences can be introduced to the receivers. Then, a common sampling of the receivers can have an effect of having the individual receivers sampling different temporal parts of the received signals. Thus in the example configuration 600, the common sampling at time t1 causes the example signal 614c (that arrives late) to be sampled at a given temporal part of the carrier structure (beginning of the cycle in the example). Sampling at time t1 causes the example signal 614b to be sampled at a temporal part of the carrier structure at a time approximately equal to the arrival difference between the receivers 610b and 610c. Similarly, sampling at time t1 causes the example signal 614a to be sampled at a temporal part of the carrier structure at a time that is approximately equal to the arrival difference between the receivers 610a and 610b. When the samplings from the receivers 610a, b, and c are combined, the resulting measurement can be equivalent to sampling at intervals of arrival difference $\Delta T$ that is substantially smaller than the common sampling interval of $T_{sampling}$.

One can see that the number of receivers and/or the arrival time difference can be selected so that the effective sampling intervals are distributed between two common sampling intervals (for example, between common sampling times t1 and t2 in FIG. 16). Thus, with proper configuration, an array of receivers can be used to sample the received signals at a frequency that is greater than the common sampling frequency, and can thereby resolve higher frequency (than the transmission signal frequency) perturbation signal components that are "riding" on the carrier signal structure.

To be able to extract the higher frequency perturbation features, it is preferable in one embodiment to not filter the received signals. In some conventional systems, filtering is used to remove these higher frequency perturbations. Such filtering, however, can filter out a perturbation that is caused by an interaction of interest along with the noise perturbations.

One can see that sampling the received signals at a effectively higher frequency as described above is one aspect of achieving an improved imaging. Such sampling samples both the perturbations of interest and noise. Thus, another aspect of improved imaging includes a method of combining the samplings from different receivers so that the signal to noise ratio of the sampled perturbations is increased.

FIG. 17 shows an example of how combination of the samplings from a plurality of receivers can enhance a relatively weak signal from a reflection of interest from the medium. A plurality of example segments of signals 620 are shown superimposed to a carrier signal (dotted curve 622). Each of the example signal segments 620 is shown to include a relatively weak signal of interest 626 among its own set of noise structures. Each signal may have different noise structures since the signal is representative of a path that is different from other signals. If any perturbation within the signal is present in at least some significant portion of the plurality of signals 620, such a perturbation is likely due to some interaction of interest in the medium, and is likely correlated among the signals.

As described above in reference to FIG. 16, such relatively fine-featured perturbations, whether a legitimate signal or noise, are more likely to be sampled with the effective sampling rate that can be substantially greater than that of the common sampling frequency. Thus, an example of a plurality of such effective samplings are depicted as dashed lines 624. It should be understood that the effective sampling lines 624 in FIG. 17 are shown only for the purpose of demonstrating that when properly correlated, the plurality of signals 620 can yield an enhancement of the perturbation of interest over the surrounding noise perturbations. A method of forming such a correlation of signal samplings is described below in greater detail.

It should also be understood that the perturbation of interest 626 in FIG. 17 is depicted as being sampled near the peak for the purpose of description. Because the arrival differences ($\Delta T$s) among the receivers may not be uniform, spacing between the effectively increased samplings may not be uniform. Consequently, samplings of the perturbation 626 may be at different parts of the perturbation peak structure. In one embodiment, such an effect limits the resolution achievable by the effectively increased sampling.

In one embodiment, properly correlated analog signals from the selected receivers can be made to interfere with each other. In such an embodiment, the various analog signals can be provided with delays according to the manner in which the signals are correlated.

In one embodiment, the raw signals from the selected receivers are digitized during the common samplings. The plurality of receivers and their associated sampling electronics are then effectively sampling and digitizing different temporal portions of their respective signals. As shown in FIG. 17, the digitized results are shown to be correlated and combined so as to yield a combined data sequence 628. When the digitized results of the signals are combined properly, individual digitized values of the perturbation of interest 626 combine to yield an enhanced digitized value 630. In contrast, the sampled and digitized noises either combine to generally cancel each other on average, or combine in a manner that is less than that of the correlated perturbation value 630.

In principle, the combining of the signals can be performed with any receivers in the array. However, Applicant's experiences have shown that correlating and combining signals from some combinations of transmitter and receivers yield better results in the quality of images.

Figure 18A:
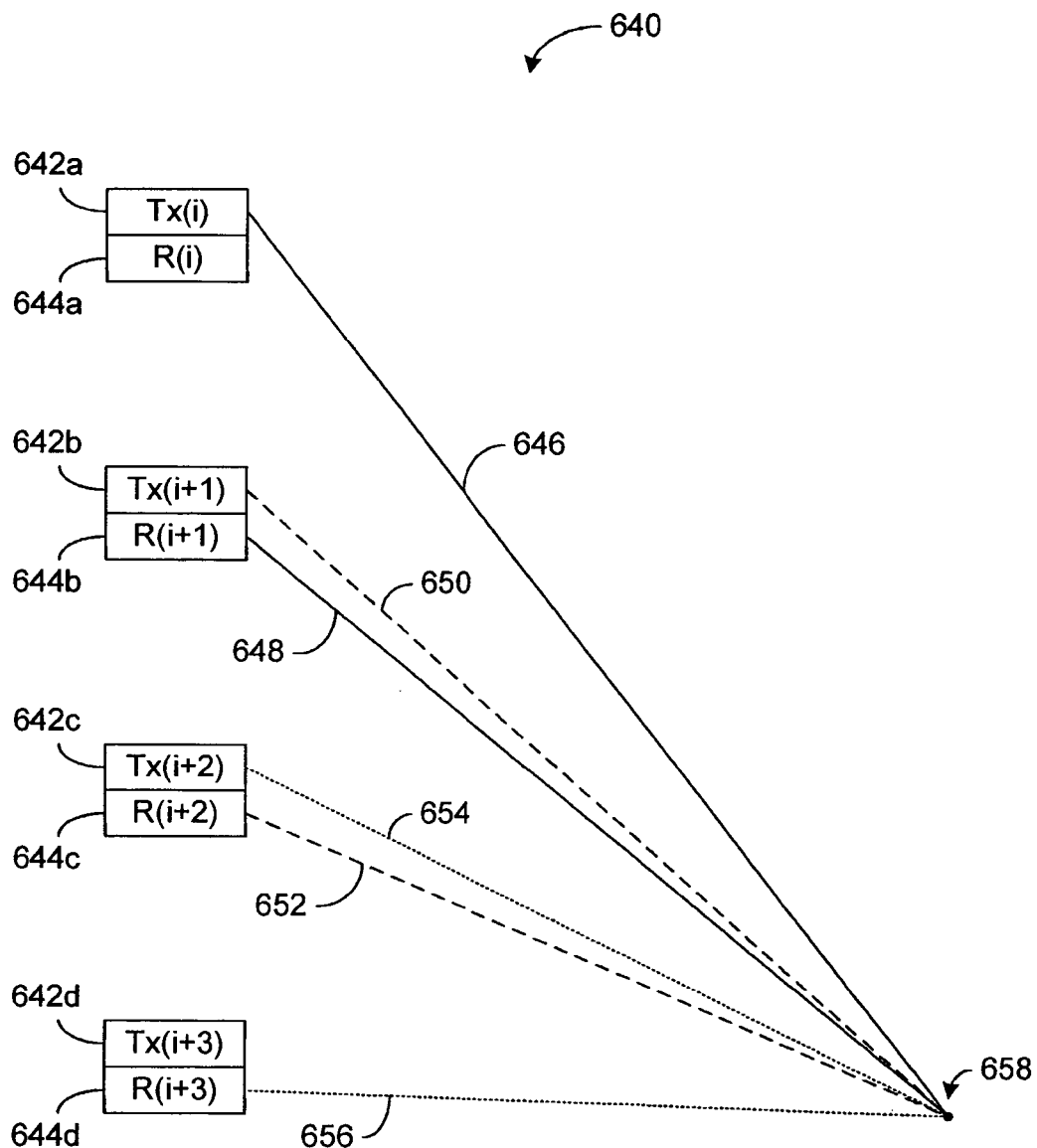
FIG. 18A shows by example how a plurality of signals from receivers that are offset by one from their respective transmitters can be combined.
Figure 18B:
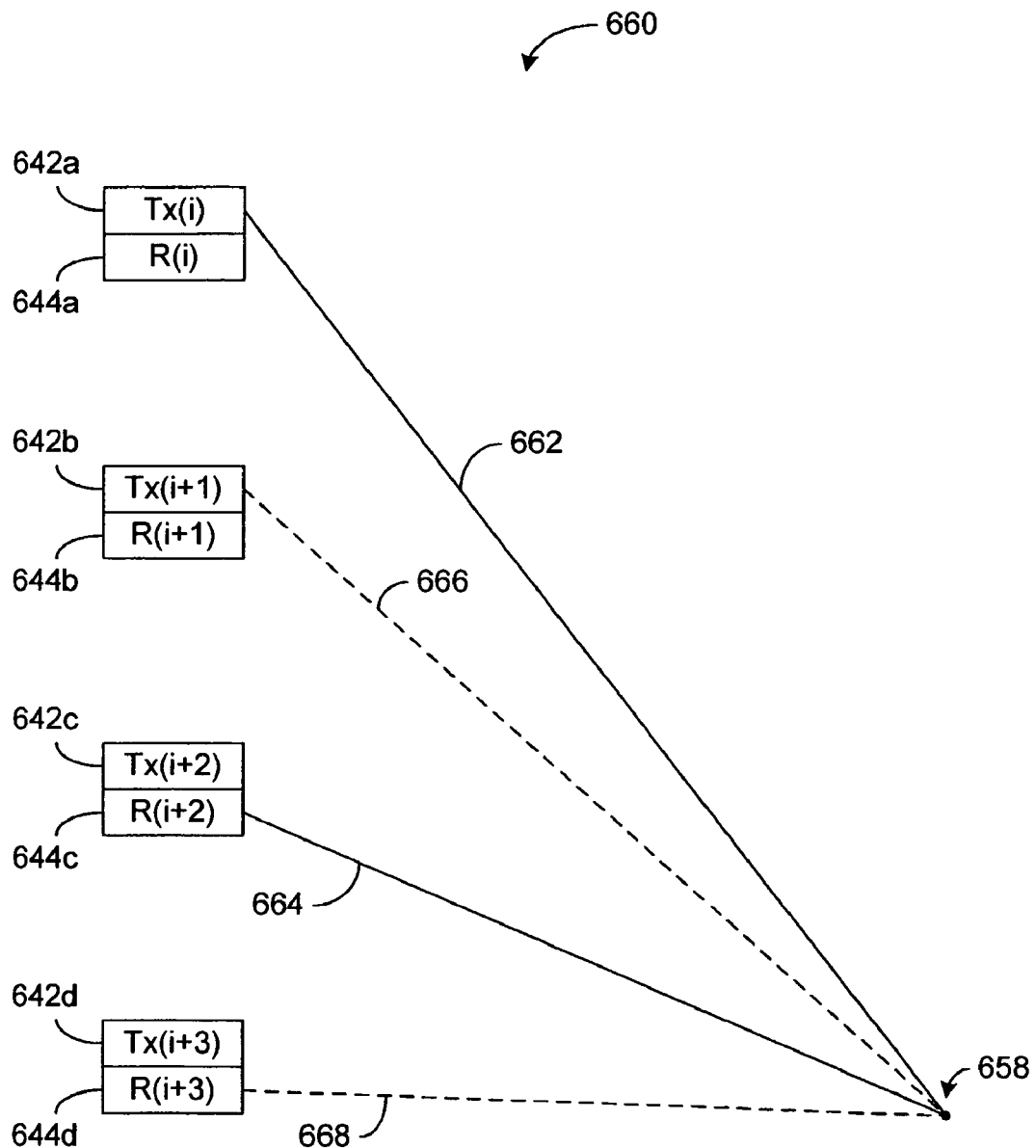
FIG. 18B shows by example how a plurality of signals from receivers that are offset by two from their respective transmitters can be combined.

FIGS. 18A and 18B show two examples of such transmitter-receiver combinations. In FIG. 18A, an example operating configuration 640 has an i-th transmitter 642a transmitting an energy 646, and a receiver (i+1) 644b that is offset by one element spacing receiving a reflected signal 648 (from an arbitrary point 658 in the medium) and generating a signal. Thus, an energy 650 from a transmitter (i+1) 642b is reflected as an energy 652 and received by a receiver (i+2) 644c.

Similarly, an energy 654 from a transmitter (i+2) 642c is reflected as an energy 656 and received by a receiver (i+3) 644d. In one embodiment, such transmit-receive combination between transducers offset by one unit provides a substantially "head-on" type of probing of the arbitrary point 658 in the medium.

In FIG. 18B, an example operating configuration 660 has the i-th transmitter 642a transmitting an energy 662, and the receiver (i+3) 644c that is offset by two element spacing receiving a reflected signal 664 (from the arbitrary point 658 in the medium) and generating a signal. Thus, an energy 666 from the transmitter (i+1) 642b is reflected as an energy 668 and received by the receiver (i+3) 644d. Such an offset can provide a more angled probing of the point 658 in the medium.

One can see that such offset pairing of the transmitter and receiver can extend to three, four, or greater offset units. In principle, any offset in the array can be used. In some applications, such a capability can be used to investigate reflections and/or emissions from a given object that are directed towards sidelobe angles.

Figure 19:
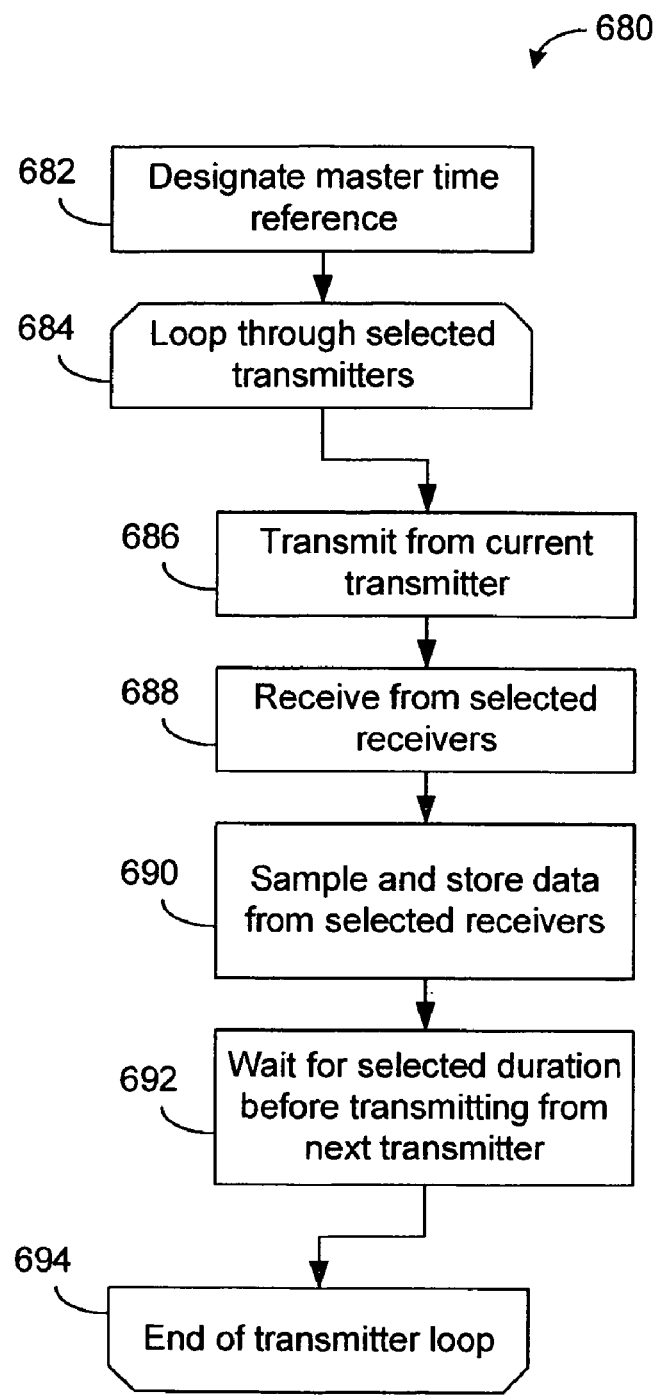
FIG. 19 shows a process for transmitting from one or more transmitters and receiving from a plurality of receivers to allow combination of resulting signals.
Figures 20, 21:
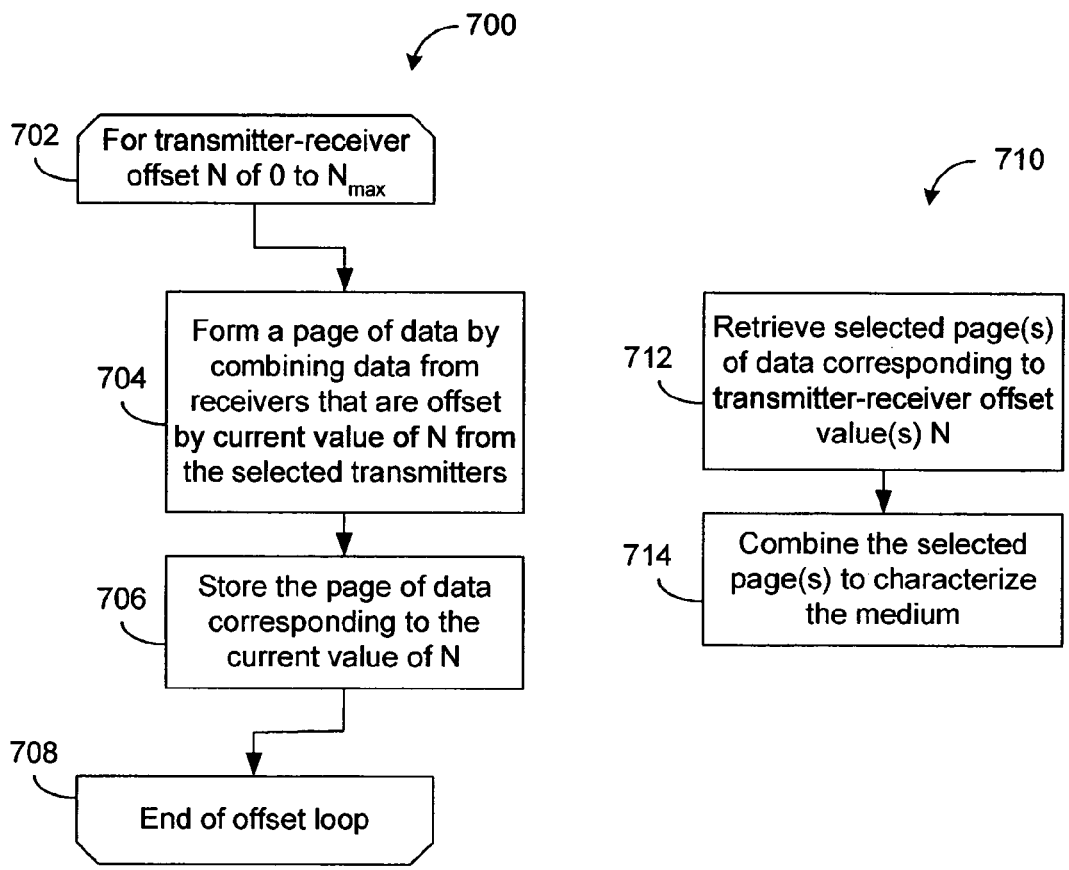
FIG. 20 shows how the received signals from the plurality of receivers can be grouped according to the receivers' respective offsets from transmitters.
FIG. 21 shows how selected groups of data based on the receiver offset can be combined.

FIGS. 19-21 now show various processes that perform the sampling and combining of signals from different transmitter-receiver offsets. FIG. 19 shows one embodiment of a process 680 that transmits from selected transmitters in a sequential manner. In one embodiment, a master time reference is designated in a process block 682. Such a master time can be used for referencing subsequent time-related operations. The process 680 then loops through the selected transmitters (begin loop 684, and end loop 694). In a process block 686, the process 680 induces the current transmitter to transmit energy into the medium. In a process block 688, the return signals are received from selected receivers. In one embodiment, all of the receivers receive return signals impinging on them. In a process block 690, the process 680 samples and stores the resulting data from the selected receivers. In one embodiment, the process 680 may wait for a selected duration before transmitting from the next transmitter.

FIG. 20 now shows one embodiment of a process 700 that combines the sampled data according to different transmitter-receiver offset groups. The process 700 loops through different values of offset N between the transmitter and the receiver of interest (begin loop 702, end loop 708). In one embodiment, the value of offset N ranges from zero to $N_{max}$, with N=0 representing a case where the receiver is in the same assembly as the transmitter. In a process block 704, the process 700 forms a "page" of data by combining data from receivers that are offset by the current value of N from the selected transmitters. In a process block 706, the process stores the page of data corresponding to the current offset value of N.

FIG. 21 now shows one embodiment of a process 710 that uses the page(s) of data to characterize the medium. In a process block 712, the process 710 retrieves selected page(s) of data corresponding to transmitter-receiver offset value(s) of N. In a process block 714, the process 712 combines the selected page(s) to characterize the medium. In one embodiment, characterization of the medium includes formation of an image of the medium.

Figure 22:
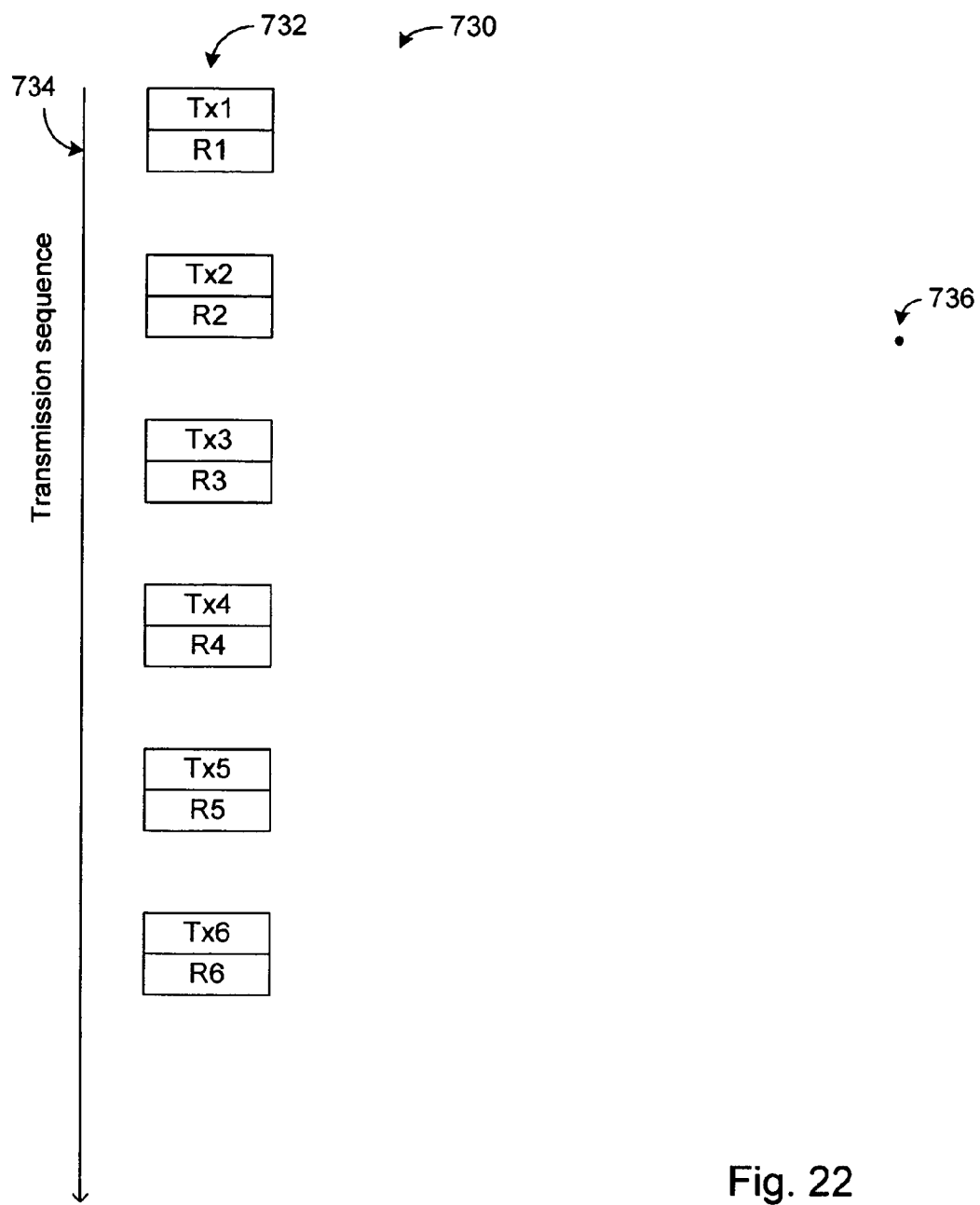
FIG. 22 shows an example of one embodiment of an array of transmitter-receiver pairs where the transmitters are triggered in sequence.

FIGS. 22 to 25 now show a specific example of the data page formation based on the offset of the transmitter and receiver pairs. For the purpose of describing by example, an example operating configuration 730 having six sets of transmitter-receiver assemblies 732 are shown in FIG. 22. It will be understood that such a configuration is only for descriptive purpose, and is not in any way intended to limit the scope of the present teachings.

In one embodiment, each transmitter-receiver assembly includes a transmitter (Tx) and a receiver (R) positioned in a close proximity to the transmitter. As depicted by an arrow 734, the six example transmitters (Tx1 to Tx6) are "fired" in sequence, starting from the first transmitter Tx1.

Also shown in FIG. 22 is an arbitrary point 736 in the medium. In one embodiment, a given transmitter does not transmit until return signals from the medium, including the point 736, would have had time to return to all of the receivers. It will be understood that the arbitrary point 736 is shown to aid in the purpose of description, and a-priori knowledge or assumption of its location with respect to the array 732 is not required.

Figure 23A:
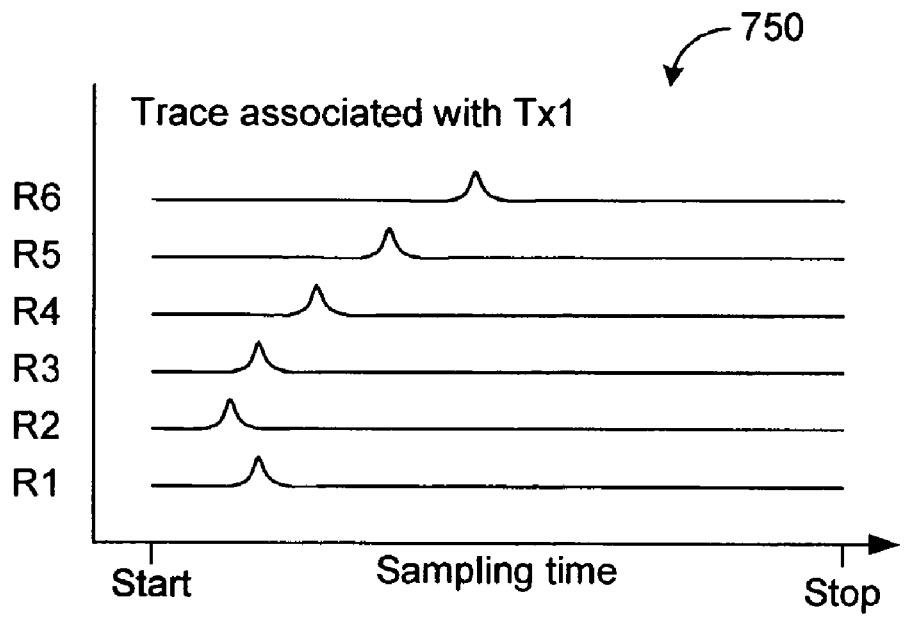
FIGS. 23A and B show a simplified depiction of example signal traces obtained from the example array of FIG. 22.
Figure 23B:
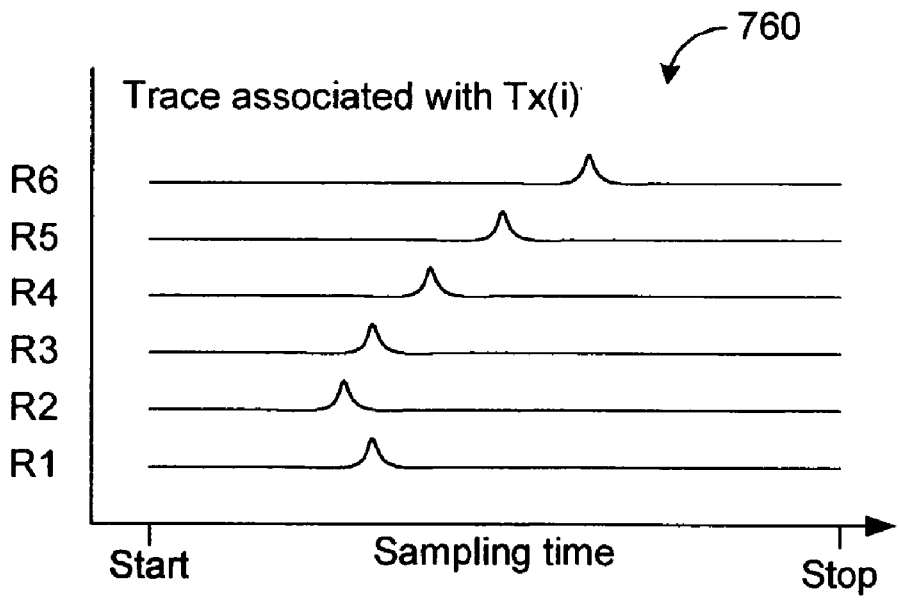

FIGS. 23A and 23B now show examples of simplified raw analog traces from the six example receivers of FIG. 22 in response to receiving of reflected signals due to a given transmitter. For the purpose of describing how a particular perturbation peak can be at different temporal portions of different traces, the traces are depicted to only show the peak. It should be understood that there will likely be other perturbation features in the traces, as described above in reference to FIGS. 16 and 17.

FIG. 23A shows example traces 750 associated with transmission from Tx1. In one embodiment, each of the traces 750 are sampled between a "Start" time and a "Stop" time while being referenced to a master time reference. Thus, if the perturbation peak is assumed to originate from the point 736 in FIG. 22, it will likely arrive at the second receiver R2 first due to that receiver being closer than others. Other receivers will likely receive the perturbation from the same point 736 successively later due to the geometry of the receivers with respect to the point 736. The differences in the arrival times can also be affected by variations in the velocity of sound in the medium. Whatever the cause may be, the arrival times need to be compensated for each of the receivers of interest from which the signals (or digitized data therefrom) are combined. One technique of performing such compensation is described below in greater detail.

FIG. 23B shows example traces 760 associated with transmission from an i-th transmitter Tx(i). Similarly, each of the sampled traces 760 can be sampled between a "Start" time and a "Stop" time while being referenced to a time reference. The time reference may or may not be the same as the master time reference described above in reference to FIG. 23A. One can see that because of the proximity of the example point 736 to the second receiver R2, the perturbation signal will likely reach R2 first, followed by successively later arrivals to other receivers spaced from R2. The arrival times within the traces 760 can also be compensated for by the method described below.

From FIGS. 23A and 23B, one can see that signal traces (raw or digitized) from different "sets" associated with different transmitters can be combined. So, if one wants to analyze the return signals from receivers that are offset by one unit from their respective transmitters, the R2 trace from the traces 750 can be combined with the trace (i+1) from the traces 760 (e.g., if i=3, then get trace from R2 and/or R4). Combining signals in such a manner allows enhancement of the perturbation signal while generally maintaining a similar "perspective" with respect to the transmitters.

FIGS. 24 and 25 now show examples of specific possible combinations of offset-one and offset-two data associated with the example operating configuration of FIG. 22. For the purpose of describing the combinations of traces associated with different transmitters, the traces are depicted in a simplified manner as to have already been digitized. Thus, the spikes in the traces represent the digitized values of the sampled perturbation signals (of FIGS. 23A and B).

FIGS. 24A-F show sampled data traces from the receivers associated with each of the six example transmitters. FIGS. 25A-F show the same sampled data traces.

FIGS. 24A-F and G show possible combinations of offset-one data, and FIGS. 25A-F and G show possible combinations of offset-two data. Thus, one can see that the same set of data traces from the receivers associated with each of the transmitters can be used for different offset combinations. Furthermore, offset-three, four, or any number can be achieved in a similar manner as that described in reference to FIGS. 24 and 25.

As shown in FIG. 24A where transmitter Tx1 is used, R2 is the offset-one receiver. As shown in FIG. 24B where transmitter Tx2 is used, R1 and R3 are offset-one receivers; thus, data from either or both receivers can be used. Similar offset-one receivers corresponding to other transmitters are shown in FIGS. 24C to 24F.

FIG. 24G shows a combined data 772 that can result from combination of data 770a-f for offset-one receivers. If the data are combined properly, the combined data 772 can include an enhanced peak 774 that corresponds to a feature of interest. A method for performing such combination is described below in greater detail.

FIGS. 25A-F and G show possible combinations of offset-two data. As shown in FIG. 25A where transmitter Tx1 is used, R3 is the offset-two receiver. As shown in FIG. 25B where transmitter Tx2 is used, R4 is the offset-two receiver. As shown in FIG. 25C where transmitter Tx3 is used, R1 and R5 are offset-two receivers; thus, data from either or both receivers can be used. Similar offset-two receivers corresponding to other transmitters are shown in FIGS. 25D to 25F.

FIG. 25G shows a combined data 782 that can result from combination of data 780a-f for offset-two receivers. If the data are combined properly, the combined data 782 can include an enhanced peak 784 that corresponds to a feature of interest. A method for performing such combination is described below in greater detail.

One can see that other receiver offset (three, four, etc.) data can also be combined in a similar manner. Thus, it will be understood that the example description of the offset-one and offset-two configurations is in no way intended to limit the scope of the present teachings.

FIGS. 26-33 now show how signals from different receivers can be combined so as to yield an enhanced signal of interest. It will be understood that the different receivers can be offset receivers, or simply part of multiple receivers.

Figure 26:
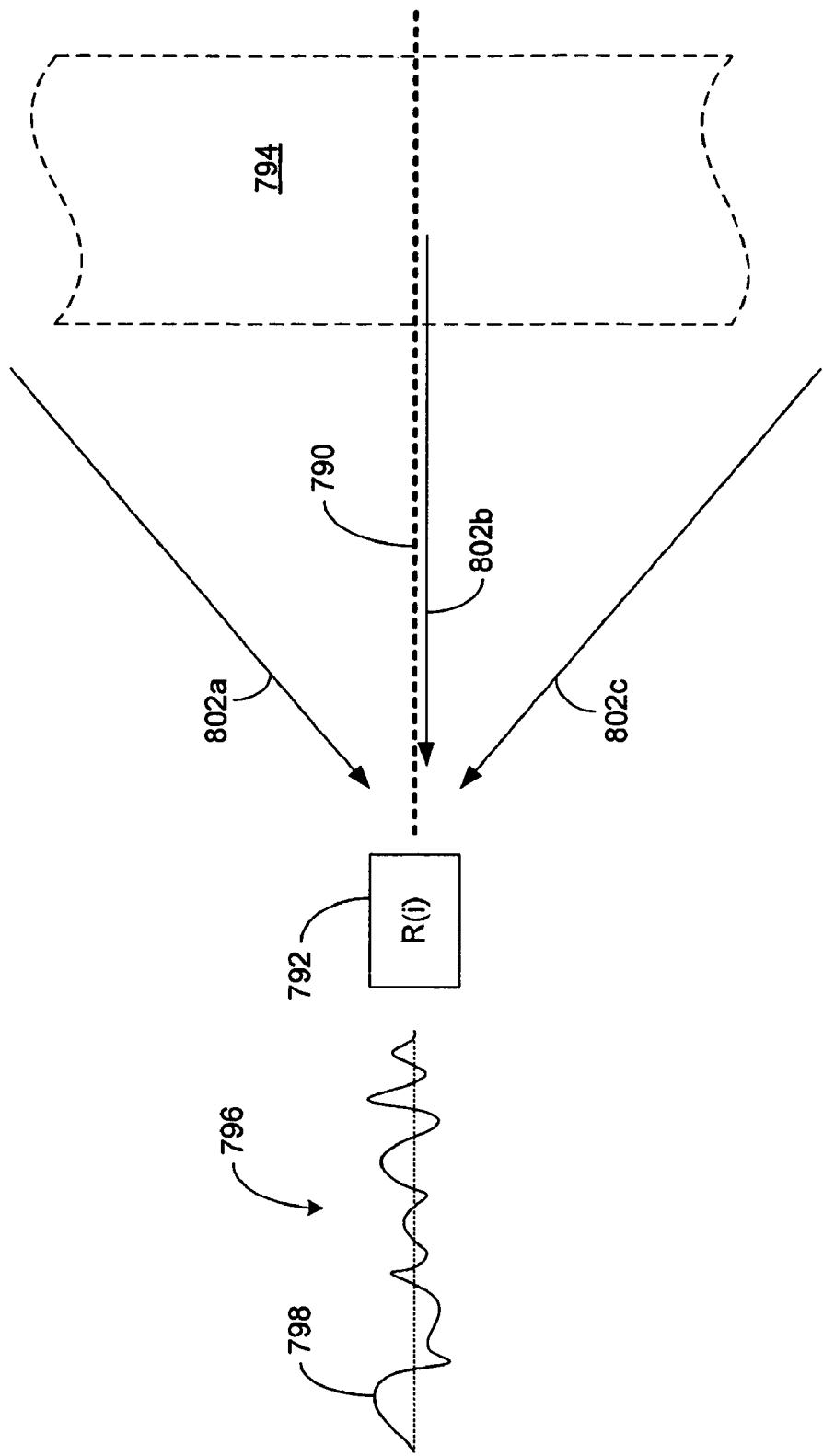
FIG. 26 shows how a signal from a given receiver can be combined with signal(s) from other receiver(s) to form a scanline for the given receiver such that the scanline has an improved performance for imaging a given layer.

FIG. 26 shows that a given receiver 792 can output an example signal 796 having fine perturbations 798 as described above in reference to FIGS. 16 and 17. The receiver signal such as the receiver signal 796 can result from return signals 802 impinging on the receiver 792 from a plurality of directions, including a direction substantially directly in front of it. An imaginary line 790 that extends substantially directly front of the receiver is shown in FIG. 26. For the purpose of description, the line 790 is shown to intersect a layer 794. Although the line 790 and the layer 794 are depicted as being perpendicular, it will be understood that such orientation is not a requirement. A line may be oriented at an angle with respect to the layer. Furthermore, a layer does not need to have a planar shape—it can be curved and form a portion of a shell-like structure about the receiver.

In one embodiment, receiver signals are combined so as to enhance or "focus" on perturbation features positioned generally along the line 790 and within the layer 794. Such "focused" combination of signals from a plurality of receivers can be thought of as a scanline associated with the receiver 792. A plurality of such scanlines associated with a plurality of receivers can then form an image along the scanlines.

Figure 27:
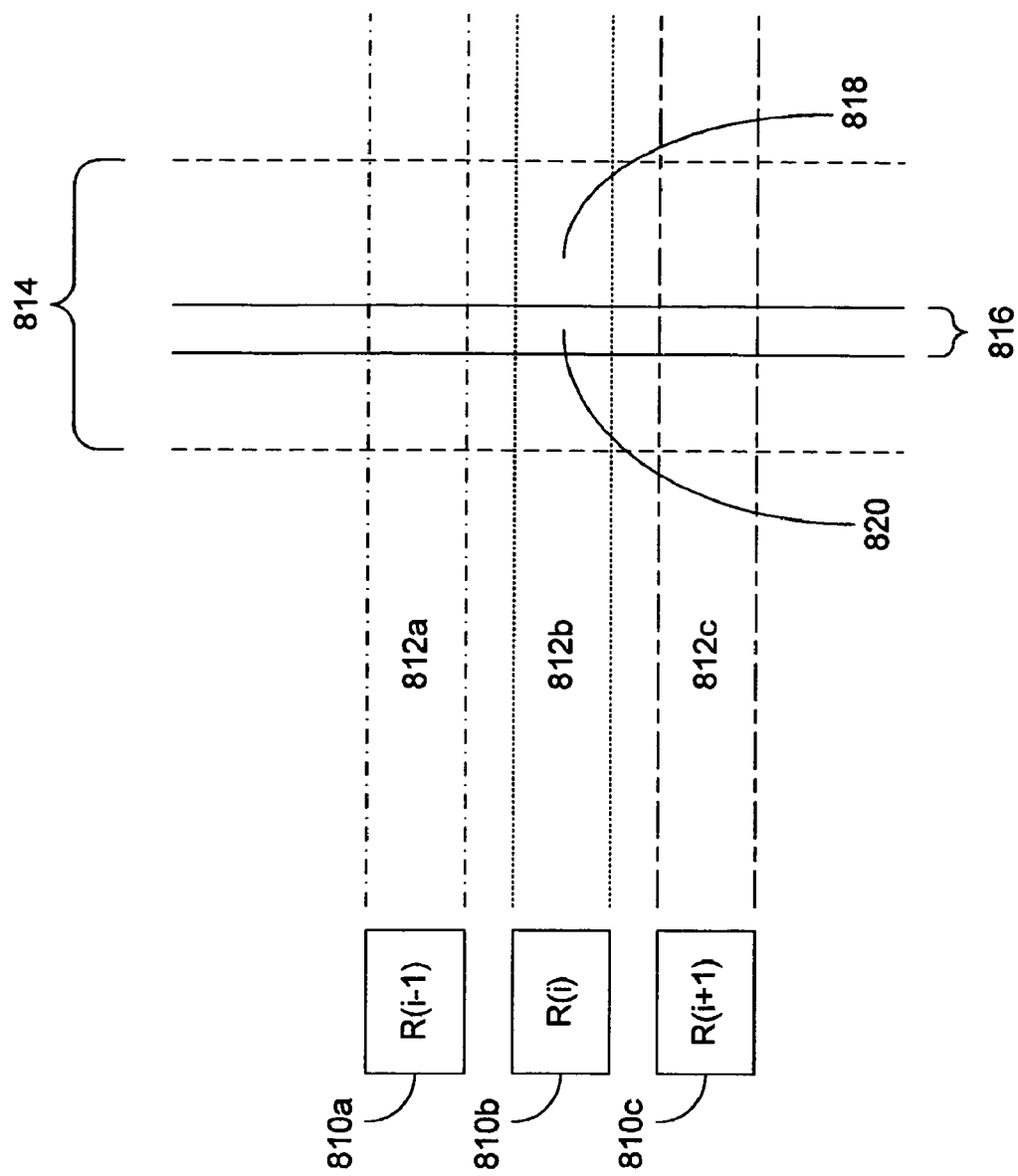
FIG. 27 shows a plurality of scanlines intersecting with a layer such that the plurality of scanlines can be focused to that layer, and wherein the layer can be split into one or more thinner layers so as to allow finer focusing of the plurality of scanlines.

FIG. 27 shows that a plurality of example scanlines 812a-c associated with a plurality of receivers 810a-c can intersect with an example layer 814. It will be understood that areas defined by such intersections are not necessarily equivalent to a "pixel." In some applications, the size of a pixel essentially places a limit on the resolution of the image generated therefrom, whether or not the detector is capable of better resolution.

In FIG. 27, an example area 818 is defined as an intersection area defined by the scanline 812b and the layer 814. In one embodiment, such an area defines a window (or depth-of-field of the scanline) in which a focus is performed. In one embodiment, if the area is not divided up any more, then that area can be considered to be a pixel for the purpose of imaging.

In one embodiment, the size of the focus area defined in the foregoing manner does not need to be fixed. As described below in greater detail, the layer 814 can be initially selected to be relatively large. Once a "coarse focus" is achieved for such a layer, that layer can be split into thinner layers. Then, the scanline(s) can be "fine focused" if desired and/or able to. Thus, as shown in FIG. 27, the layer 814 can be split into thinner layers such as an example layer 816, and a focus area 820 would be associated with that relatively thinner layer.

FIGS. 28 to 30 now show by example how scanlines associated with three example receivers can be brought into focus at different layers. For the purpose of description, an example array of three receivers 810a-c are shown in FIGS. 28A, 29A, and 30A. Associated with the receivers 810a-c are imaginary lines 812a-c that extend therefrom respectively. For the purpose of description, the lines 812a-c are divided into three example layers 822a-c. Also for the purpose of description, a first feature of interest 824 is shown to be located generally in an area defined by the line 812a and the layer 822b. A second feature of interest 826 is shown to be located generally in an area defined by the line 812b and the layer 822a. A third feature of interest 828 is shown to be located generally in an area defined by the line 812c and the layer 822c. For the purpose of showing how different features of interest can be shifted in sampling time, the three features of interest are depicted as triangle 824, circle 826, and square 828.

Figure 28A:
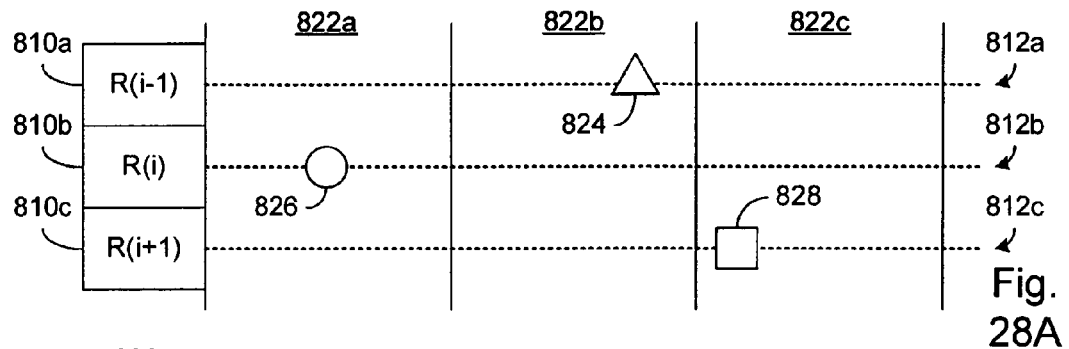
FIG. 28A shows an example of features located along different scanlines and in different layers.
Figure 28B:
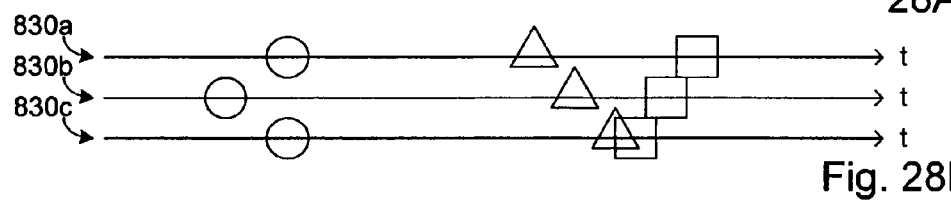
FIG. 28B shows an example of measured signal traces having components associated with the example features of FIG. 28A.
Figure 29A:
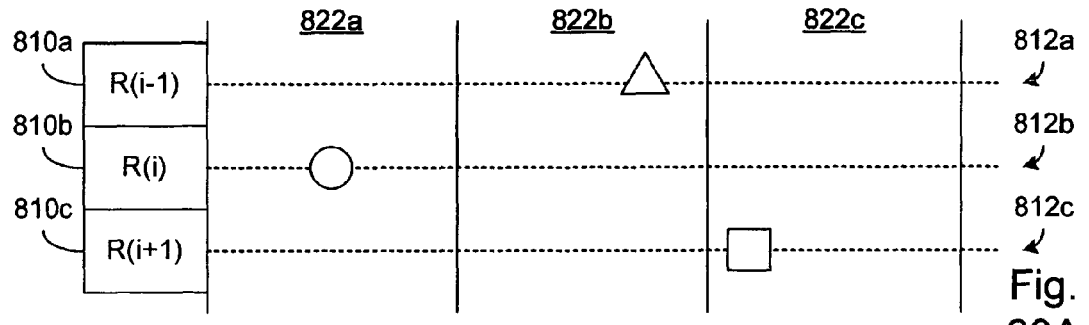
FIG. 29A shows an example of features located along different scanlines and in different layers.
Figure 29B:
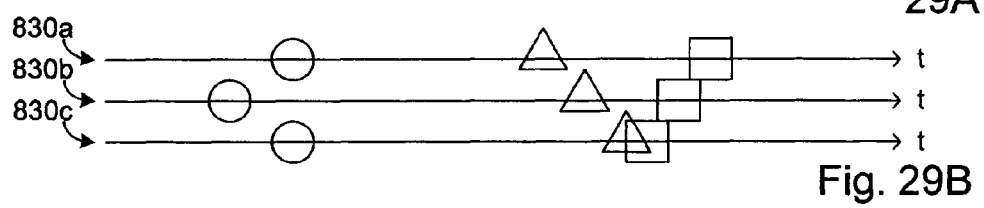
FIG. 29B shows an example of measured signal traces having components associated with the example features of FIG. 29A.
Figure 30A:
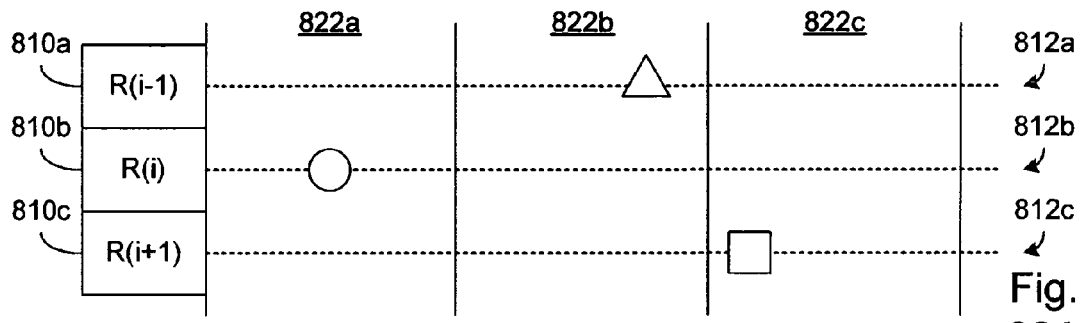
FIG. 30A shows an example of features located along different scanlines and in different layers.
Figure 30B:
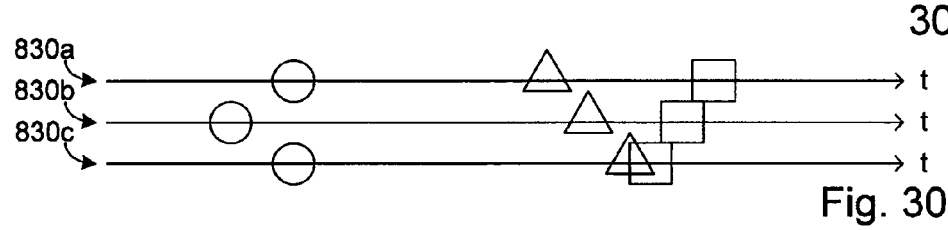
FIG. 30B shows an example of measured signal traces having components associated with the example features of FIG. 30A.

FIGS. 28B, 29B, and 30B are also common, showing that data traces 830a-c associated with their respective receivers 810a-c "see" the three example features of interest 824, 826, and 828 at relatively different times. For example, the triangle 824 is generally in front of and closest to the receiver 810a. Consequently, as the data trace 830a associated with the receiver 810a shows, the receiver 810a will likely receive a return signal from the triangle 824 first, followed by the receiver 810b, which in turn is followed by the receiver 810c. Similarly, the circle 826 is generally in front of and closest to the receiver 810b. Consequently, as the data trace 830b shows, the receiver 810b will likely receive a return signal from the circle 826 first, and the receivers 810a and 810c after that.

As shown in FIGS. 28A, 29A, and 30A, the receivers 810a-c are depicted as being arranged in an ordered array. It will be understood that such a depiction is only for the purpose of describing the concept of relative arrival times of return signals to the different receivers, and how such signals can be combined to form a focused scanline. In particular, it will be understood that although the example receivers 810a-c are shown in sequence, they do not necessarily need to be as such physically. For example, different receiver-offset data can be combined as described above; and in such situations, the receivers whose signals are being combined may not be next to or even relatively close to each other. Thus, the arrangement of the receivers 810a-c should be considered to represent a logical arrangement for the purpose of description.

Figure 28C:
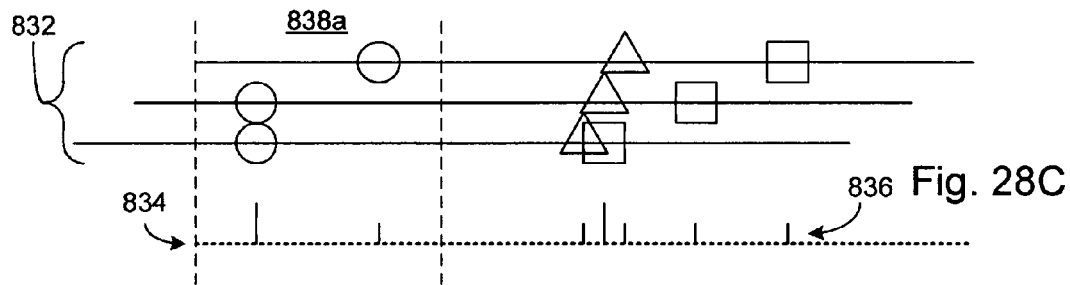
FIGS. 28C-E show by example "in-focus" combinations at various layers for the signal traces to form the scanline associated with the first example receiver.

FIG. 28C shows an example focused layer 838a for a scanline 834 associated with the receiver 810a. Depicted along with the scanline 834 are relative peak heights 836 associated with the combined return signals from the three features 824, 826, and 828 when the scanline is in focus. Relative shifting of return signal traces to achieve the focus is shown as a set 832 of shifted traces. It will be noted that one does not need to know how much to shift one trace relative to another trace beforehand to achieve a focus. A method for determining a focused state from different combinations of shifting is described below in greater detail. For the purpose of describing the result of such focusing for a given scanline in reference to FIGS. 28-30, the scanlines are depicted as being brought into focus.

Figure 28D:
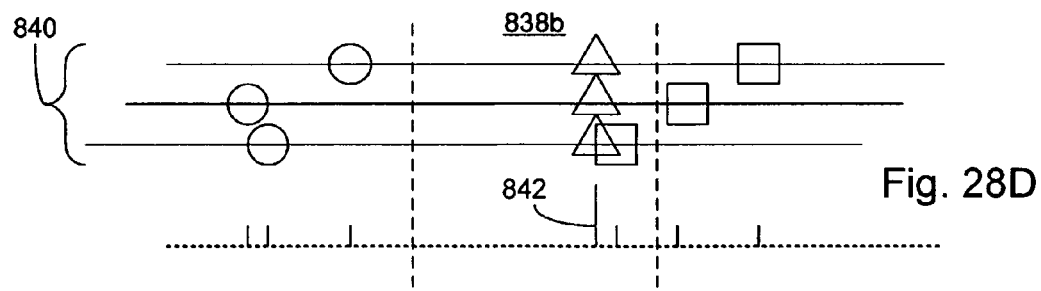

Similarly, FIG. 28D shows an example focused layer 838b for the scanline 834 associated with the receiver 810a. Depicted along with the scanline 834 are relative peak heights 836 associated with the combined return signals from the three features 824, 826, and 828 when the scanline is in focus. Relative shifting of return signal traces to achieve the focus is shown as a set 840 of shifted traces.

Figure 28E:
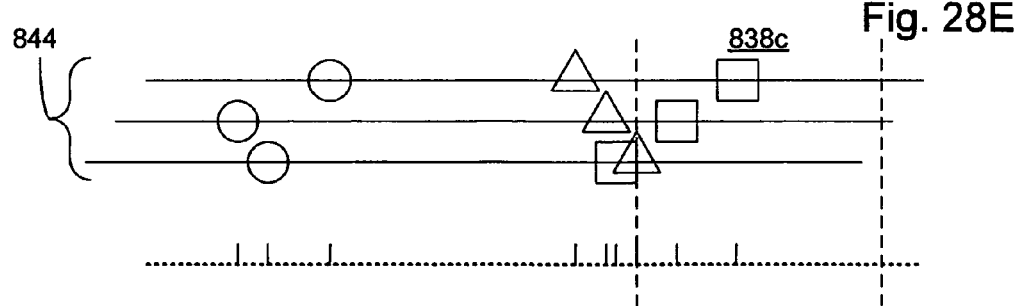

Similarly, FIG. 28E shows an example focused layer 838c for the scanline 834 associated with the receiver 810a. Depicted along with the scanline 834 are relative peak heights 836 associated with the combined return signals from the three features 824, 826, and 828 when the scanline is in focus. Relative shifting of return signal traces to achieve the focus is shown as a set 844 of shifted traces.

In FIG. 28D, one can see that the focused layer 838b results in an enhanced peak 842 corresponding to the aligning (by proper shifting of the data traces) of the triangle 824. Such enhanced peaks can be utilized to determine whether a scanline is in focus in a given layer. Such determination is described below in greater detail.

Also note that for the line 812a associated with the receiver 810a, the first and third layers 822a and 822c do not have any features. Thus, an image resulting from a properly focused scanline should not show features in those two layers 822a and 822c. In one embodiment, such result can be achieved by making a threshold cut on the peak(s) in a given focused layer so that peaks below that threshold are not processed for image formation. For example, if one was to set the threshold so as to accept the enhanced peak 842 but reject lower peaks, the first and third focused layers 838a and 838c can form focus areas having substantially null images.

Figure 29C:
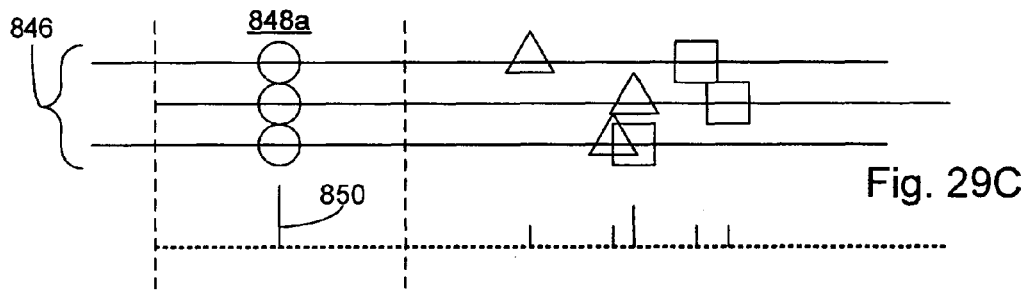
FIGS. 29C-E show by example "in-focus" combinations at various layers for the signal traces to form the scanline associated with the second example receiver.

FIG. 29C shows an example focused layer 848a for a scanline associated with the receiver 810b. Depicted along with the scanline are relative peak heights associated with the combined return signals from the three features 824, 826, and 828 when the scanline is in focus. Relative shifting of return signal traces to achieve the focus is shown as a set 846 of shifted traces.

Figure 29D:
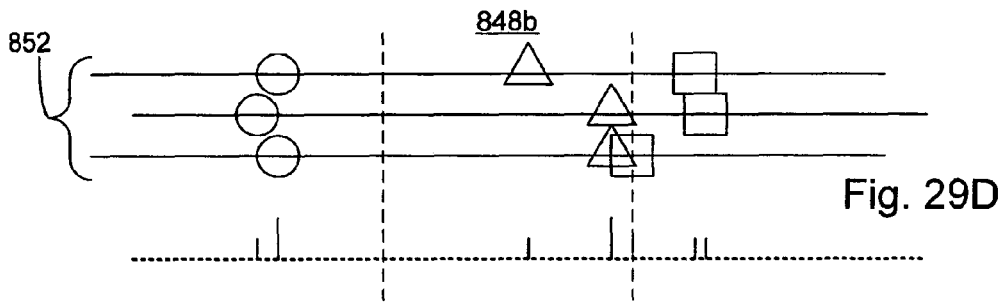

Similarly, FIG. 29D shows an example focused layer 848b for the scanline associated with the receiver 810b. Depicted along with the scanline are relative peak heights associated with the combined return signals from the three features 824, 826, and 828 when the scanline is in focus. Relative shifting of return signal traces to achieve the focus is shown as a set 852 of shifted traces.

Figure 29E:
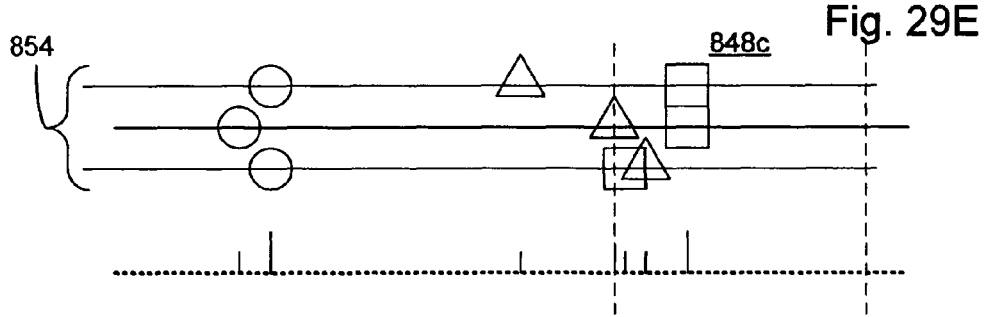

Similarly, FIG. 29E shows an example focused layer 848c for the scanline associated with the receiver 810b. Depicted along with the scanline are relative peak heights associated with the combined return signals from the three features 824, 826, and 828 when the scanline is in focus. Relative shifting of return signal traces to achieve the focus is shown as a set 854 of shifted traces.

In FIG. 29C, one can see that the focused layer 848a results in an enhanced peak 850 corresponding to the aligning (by proper shifting of the data traces) of the triangle 826. Such an enhanced peak can be used to form an image for the area associated with the line 812b and the layer 848a.

Figure 30C:
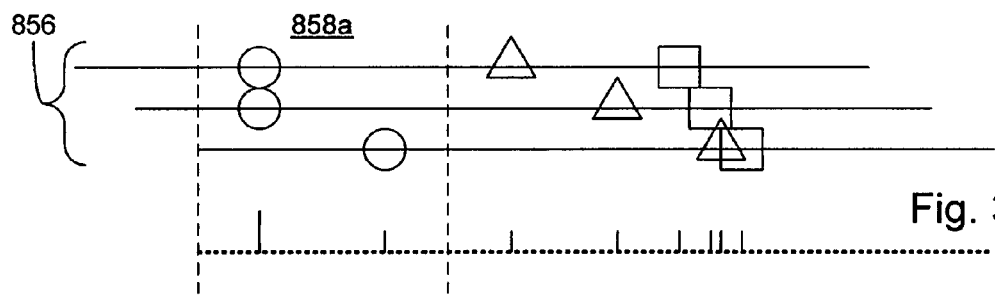
FIGS. 30C-E show by example "in-focus" combinations at various layers for the signal traces to form the scanline associated with the third example receiver.

FIG. 30C shows an example focused layer 858a for a scanline associated with the receiver 810c. Depicted along with the scanline are relative peak heights associated with the combined return signals from the three features 824, 826, and 828 when the scanline is in focus. Relative shifting of return signal traces to achieve the focus is shown as a set 856 of shifted traces.

Figure 30D:
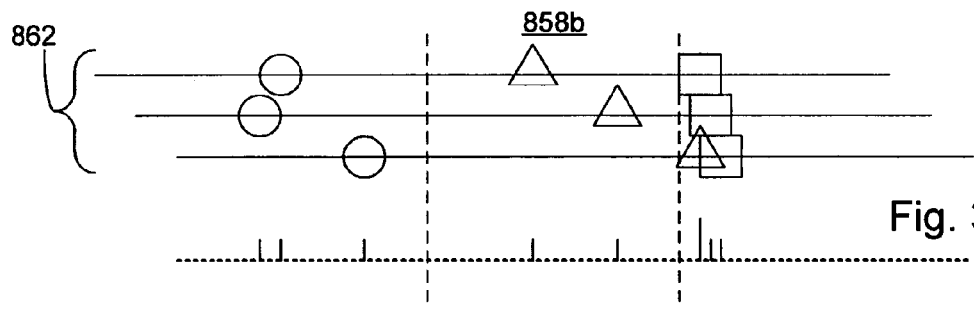

Similarly, FIG. 30D shows an example focused layer 858b for the scanline associated with the receiver 810c. Depicted along with the scanline are relative peak heights associated with the combined return signals from the three features 824, 826, and 828 when the scanline is in focus. Relative shifting of return signal traces to achieve the focus is shown as a set 862 of shifted traces.

Figure 30E:
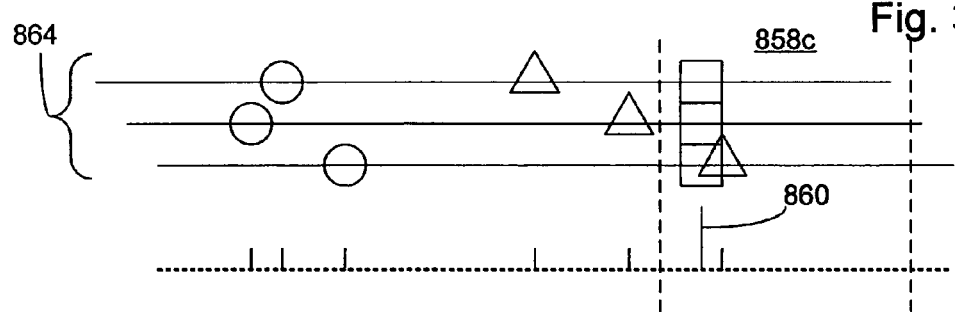

Similarly, FIG. 30E shows an example focused layer 858c for the scanline associated with the receiver 810c. Depicted along with the scanline are relative peak heights associated with the combined return signals from the three features 824, 826, and 828 when the scanline is in focus. Relative shifting of return signal traces to achieve the focus is shown as a set 864 of shifted traces.

In FIG. 29E, one can see that the focused layer 858c results in an enhanced peak 860 corresponding to the aligning (by proper shifting of the data traces) of the square 826. Such an enhanced peak can be used to form an image for the area associated with the line 812c and the layer 858c.

In one embodiment, a layer closest to a given receiver is focused first, followed by successive layers therefrom. Focusing of a given layer allows determination of propagation time within that layer, since the amount of shifting of various data traces depends on how much differences there are in the propagation times. Thus, a given layer is brought into focus when the proper amount of shifting is applied (i.e., when the proper propagation time is determined for that layer).

In one embodiment, the foregoing focusing process and/or the focus results therefrom can be implemented with physical movements of one or more transducer elements. For example, arrays having movable elements similar to that of adaptive optics can be adjusted to either aid the focusing process, or to re-position the elements so that subsequent focusing process can be achieved more efficiently. In one specific example, suppose that a focused section of a scanline is achieved when data traces from one or more receivers are shifted so as to be near their limits. In such cases, the corresponding receivers may be moved so as to introduce changes in propagation times thereto, so that likely "focused" sections of the corresponding data traces are now located more centrally, thereby providing more "working" room in the shifting of data traces.

By focusing on the closest layer, the propagation time for that layer is determined. Focusing of the next layer can then be facilitated by the knowledge of the first layer. This building of propagation time information can build successively outward away from the receiver.

It will be understood that the shifting of data traces described for the purpose of combining those data traces refer to shifting in time. In one embodiment where each data trace includes a series of digital representations of samplings, each sampling has a time associated with it. Thus, time-shifting can be in the form of shifting data trace based on such "time stamp" of the samplings. Based on the foregoing, a "time-shift combination" operation includes shifting of time or phase associated with portions of a plurality of data traces with respect to each other. For example, if a scanline is being focused at a given layer, temporal ranges of data traces being combined can be identified (for example, by an initial estimation based on geometry). Then, digital data within those ranges can be shifted with respect to each other and combined to yield a quality value associated with that combination.

Figure 31A:
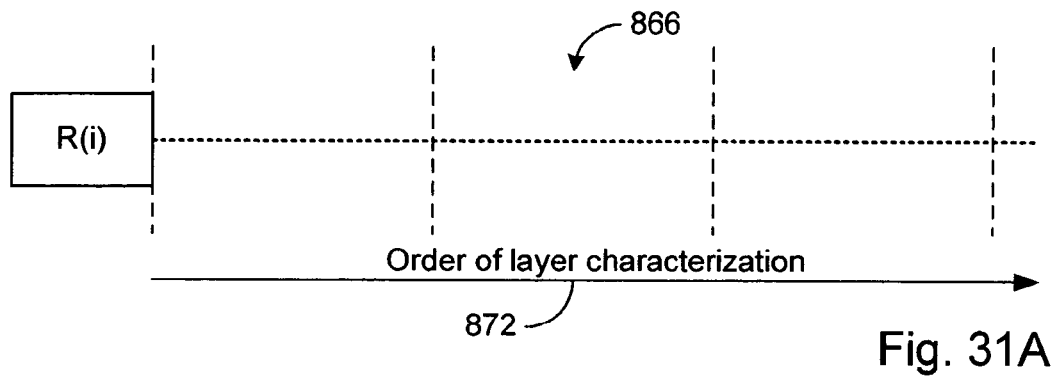
FIGS. 31A-C show that in one embodiment, a scanline can be focused from the layer closest to the receiver, and that a given layer can be split into finer layers for finer focusing.
Figure 31B:
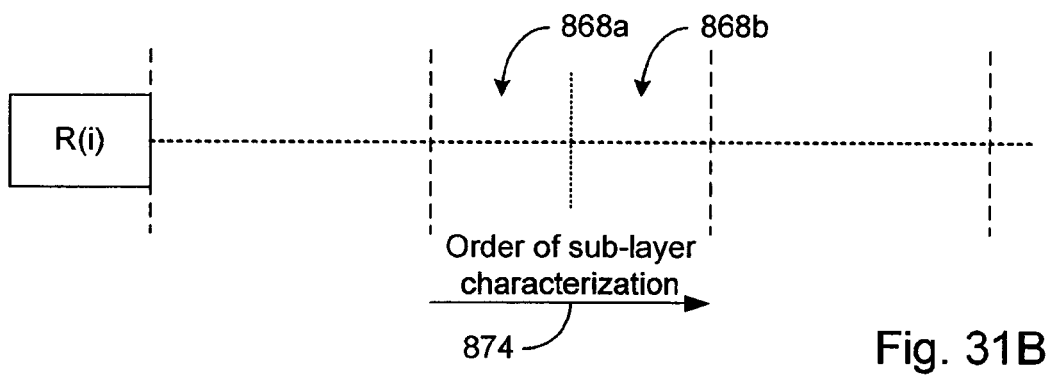
Figure 31C:
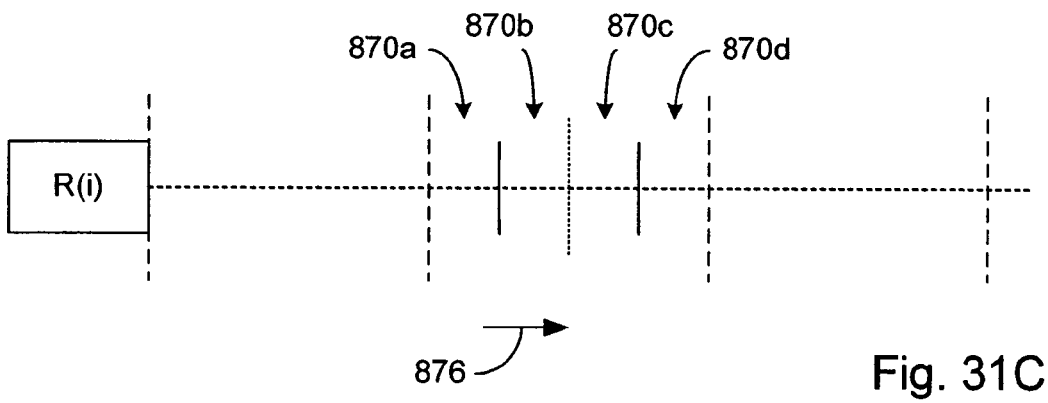

FIGS. 31A-C show such a successive layer characterization method. In FIG. 31A, an arrow 872 directed away from a receiver indicates the order of layer characterization. Also in FIG. 31A, an example layer 866 is shown. If that layer is to be split for finer focusing, such as layers 868a and 868b in FIG. 31B, characterization of those sublayers can be characterized successively beginning from the sub-layer closest to the receiver (as indicated by an arrow 874). Similarly, each of the sub-layers 868 can be split further into layers 870a-b and 870c-d. Again, such layers can be characterized successively beginning from the one closest to the receiver (as indicated by an arrow 876).

It will be understood that the foregoing successive layer characterization (beginning with the closest layer to the receiver) is just one example of focusing on the plurality of layers. As described herein, focusing on a given layer does not necessarily depend on the knowledge of another layer. Thus, focusing can begin at any layer in the medium without departing from the scope of the present teachings.

Figure 32:
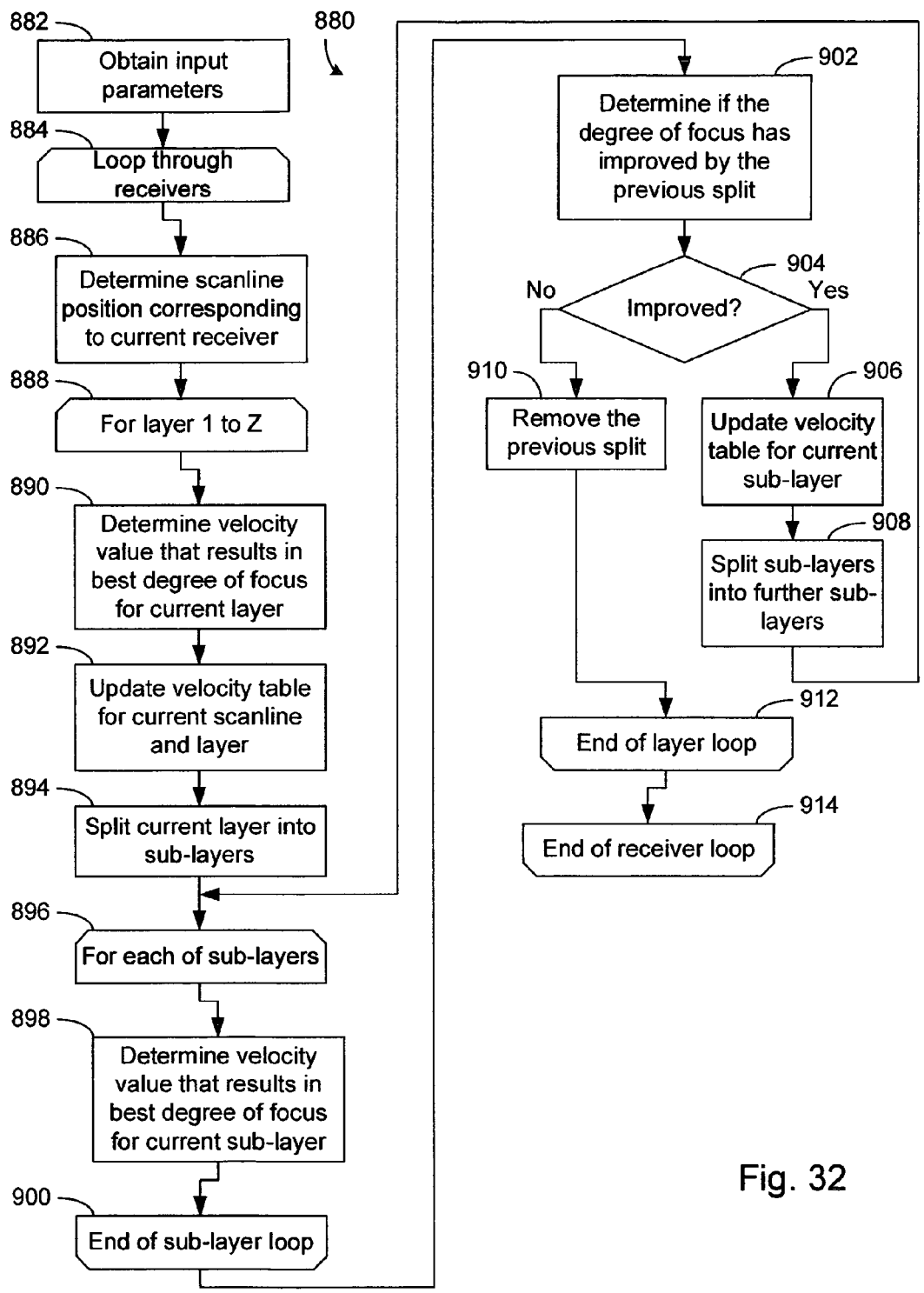
FIG. 32 shows a process for focusing a plurality of scanlines in a plurality of layers, such that a given layer can be split for finer focusing if advantageous to do so.
Figure 33:
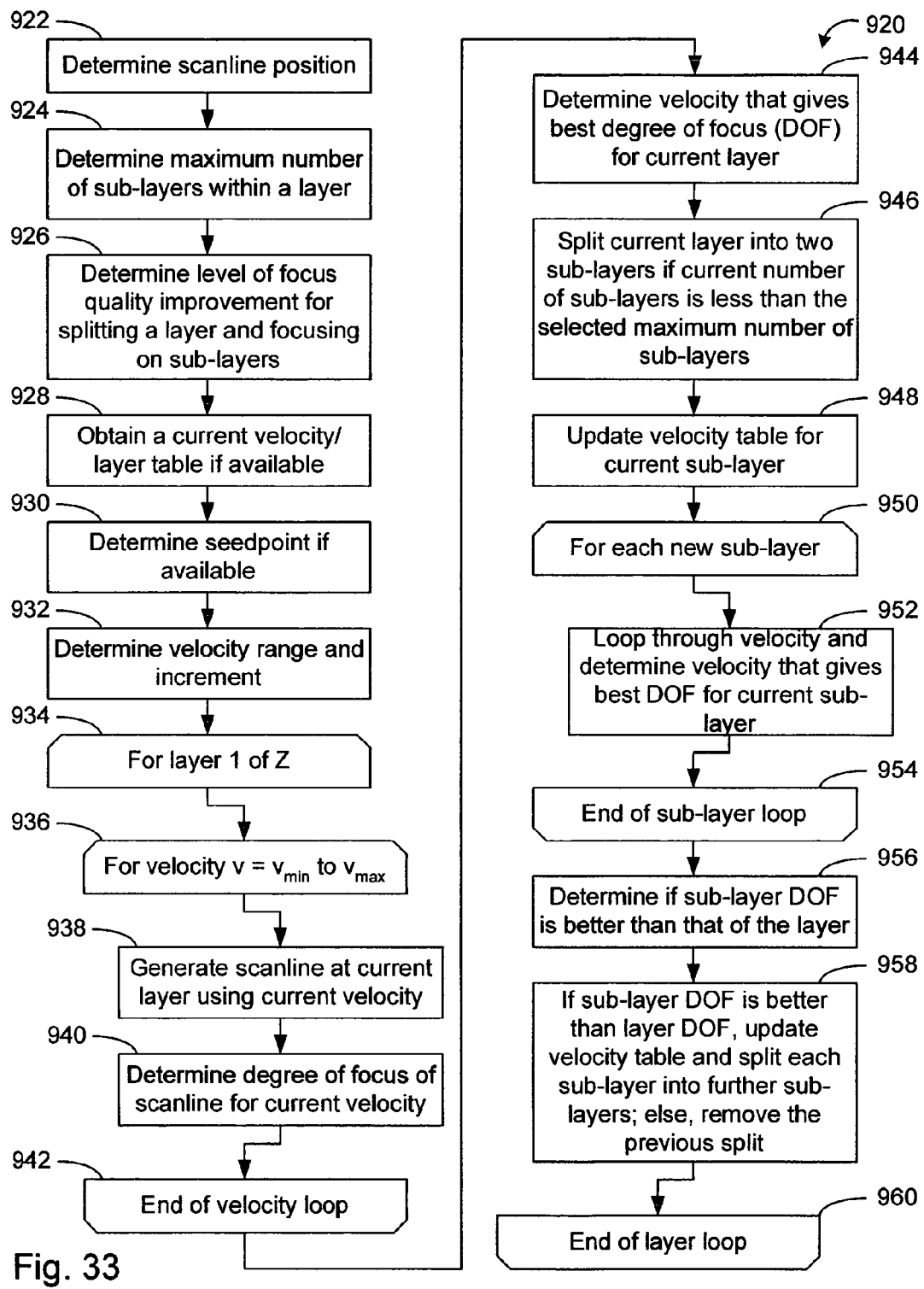
FIG. 33 shows a more specific example of the process of FIG. 32.

FIGS. 32-33 now show how a scanline can be focused at a given layer—that is, how signal traces from different receivers can be combined so as to optimally enhance perturbation features of interest. For the purpose of describing the focusing technique, "velocity" (generally inversely proportional to time) is used to characterize the propagation time within a given layer. It should be noted that in the focusing technique of FIG. 32-33, a prior knowledge of velocity is not necessary.

FIG. 32 shows a process 880 for determining focused scanlines for one or more receivers at different layers. In one embodiment, the process 880 further includes finer-focusing capability that splits a given layer if that split provides an improved scanline focus quality. The process 880 in general includes a process block 882 where input parameters are obtained. Some of the input parameters are described in a more specific process in reference to FIG. 33.

The process 880 then loops through the receivers (end loop 914). In a process block 886, the process 880 determines the position of a scanline corresponding to the current receiver. For the current receiver, the process 880 loops through each of the Z layers (end loop 912). In one embodiment, the layers are successively looped through from layer one to layer Z, with layer one being the closest to the receiver.

For the current receiver and the current layer, the process 880 in a process block 890 determines a velocity value that results in the best degree of focus for the current scanline in the current layer. Various methods of determining the degree of focus selecting the "best" therefrom are described below in greater detail. As previously described, a prior knowledge of velocity value is not necessary. However, providing a likely range of velocity values may result in a more efficient combinatoric computation for combining and determining the degree of focus.

The process 880 in a process block 890 then updates the velocity data corresponding to the current scanline and the layer. Such data can be stored as a table, or any manner that allows retrieval for later use.

In one embodiment, the current layer is initially split into sub-layers in a process block 894, and focusing is performed in each of the newly created sub-layers in a sub-layer loop 896 (end loop 900). Each of these sub-layers may be further split, and each of those newly created layers may undergo similar loop. This successive splitting process may continue further. Thus, for the purpose of description, the sub-layer loop 896 is depicted as a module that can be accessed whenever a set of sub-layers are looped through.

Within the sub-layer loop 896, the process 880 in a process block 898 determines a velocity value that results in the best degree of focus for the current sub-layer. Whether that velocity value will replace the existing velocity value for the area overlapping the current sub-layer depends on whether the current sub-layer focus is an improvement. In one embodiment, such determination can be made on a sub-layer by sub-layer basis, or collectively for the set of sub-layers. As an example, an average of the degrees of focus for the sub-layers can be compared to the degree of focus for the parent layer. For the purpose of description, the process 880 is shown to determine if the degree of focus has improved collectively by the split in a process block 902.

Once such determination is made, the process 880 in a decision block 904 determines whether the focus has improved by the split. If the answer is "yes," then the process 880 in a process block 906 updates the velocity table for the sub-layers of the current layers. To see if the focus can be made even finer, thereby improving the resolution, each of the current sub-layers are further split in a process block 908, and focusing is performed on each of the newly created sub-layers by invoking the sub-layer loop 896. If the answer in the decision block 904 is "no," then the process 880 removes the previous split in a process block 910, since the finer "focus" did not yield a better result.

FIG. 33 now shows a more specific example process 920 of how the process 880 of FIG. 32 can be implemented. For the purpose of simplicity, the process 920 is described for one given receiver. But as shown in FIG. 32, such a process can be looped over a plurality of receivers.

The process 920 in a process block 922 determines the position of a scanline associated with the receiver being analyzed. In a process block 924, a maximum number of sub-layers within a given layer is obtained. In one embodiment, that maximum number places a limit on the extent of splitting for finer focusing. In a process block 926, the process 920 obtains a level of focus quality improvement to trigger additional splitting for finer focusing. In a process block 928, the process 920 obtains a current velocity table for the layers if available and/or desired. In a process block 930, a seedpoint (such as a value representative of a lowest expected velocity) is obtained if available and/or desired. In a process block 932, the process 920 obtains the range and increment of velocity for determining the velocity associated with the best degree of focus.

The process 920 then loops through layers one to Z in a loop 936 (end loop 960). For each current layer, the process 920 loops through the range of velocity values in a loop 936 (end loop 942). For the current velocity value, the process 920 generates a scanline at the current layer in a process block 938. The process 920 then determines a degree of focus of the scanline for the current velocity in the process block 940.

Once the process loop 936 is completed, the process 920 in a process block 944 determines a velocity that results in the best degree of focus for the current layer. In a process block 946, the process 920 splits the current layer into two sub-layers if the current number of sub-layers is less than the selected maximum number of sub-layers (obtained in the process block 924). In a process block 948, the velocity table is updated with the velocity value that gave the best degree of focus for the current layer.

The process 920 then loops through the newly created sub-layers (if any) in the process block 946 in a loop 950 (end loop 954). For each sub-layer, the process 920 in a process block 952 loops through the velocity range and determines a velocity value that results in the best degree of focus for that sub-layer in a manner similar to that of the loop 936. The process 920 then determines if degree of focus associated with the sub-layers is better than that of the parent layer in a process block 956. In one embodiment, the new degree of focus is considered to be better than that of parent layer if it exceeds the level of focus quality improvement obtained in the process block 926.

If the sub-layer degree of focus is better than the parent layer degree of focus, the process 920 in a process block 958 updates the velocity table and splits each of the current sub-layers into two sub-layers. Again, this splitting can be limited by the maximum number of sub-layer as determined in the process block 924. If the sub-layer degree of focus is not better than the parent degree of focus, the process 920 removes the previous split and retains the parent layer level of focus.

Figure 34A:
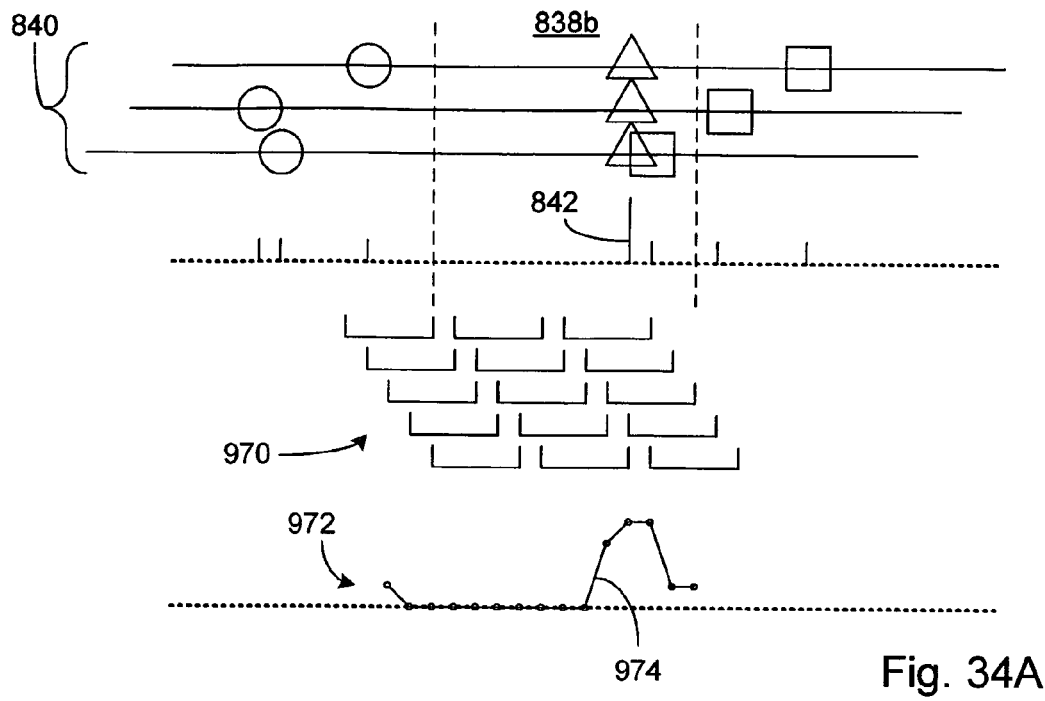
FIGS. 34A-B show some of the many possible ways of combining various signal traces to obtain a best in-focus scanline at a given layer.

In the description herein in respect to FIGS. 26-33, various references are made about focusing, degree of focus, and the like. FIGS. 34A and B now show by example how a focus can be achieved by determining a parameter representative of the best degree of focus. A "focus" associated with an array of signal values can be determined in a variety of ways. For example, some autofocus cameras compare relative contrasts of adjacent or nearby signal values—the reason being that a sharply focused image will have more of a sudden change in the contrast. A similar method can be applied for determining the degree of focus for a scanline of interest.

In one embodiment, the splitting of layers can provide a substantial advantage in how effectively a given volume can be imaged. As an example, suppose that a volume includes a relatively small group of features of interest localized in a relatively small region. The rest of the volume is substantially homogeneous for the purpose of propagating signals. Such homogeneous portions likely will not need to be split, since the velocity therein is substantially uniform. When the small inhomogeneous region is encountered, it can be split into smaller layers to allow characterization of sub-regions with different velocity values. Thus, one can see that the combining process does not need to waste time attempting to split the homogeneous portion. Moreover, the inhomogeneous region can be characterized better by the splitting method, thereby allowing improved characterization of the volume.

FIG. 34A shows the shifted data trace set 840 corresponding to "in focus" configuration as described above in reference to FIG. 28D. FIG. 34A further shows one of a number of possible ways of determining the degree of focus for the trace combination set 840. In one embodiment, a running average of the combined scanline is obtained for a selected window. In one embodiment, such a window may overlap the focus layer 838*b* and extend beyond. In one embodiment, the window may be defined as temporally substantially similar to the boundaries corresponding to the focus layer 838*b*.

In one embodiment, the running averages are formed by a plurality of partially overlapping averaging intervals 970. Average values 972 associated with the intervals 970 are depicted at the approximate centers of the intervals 970.

Figure 34B:
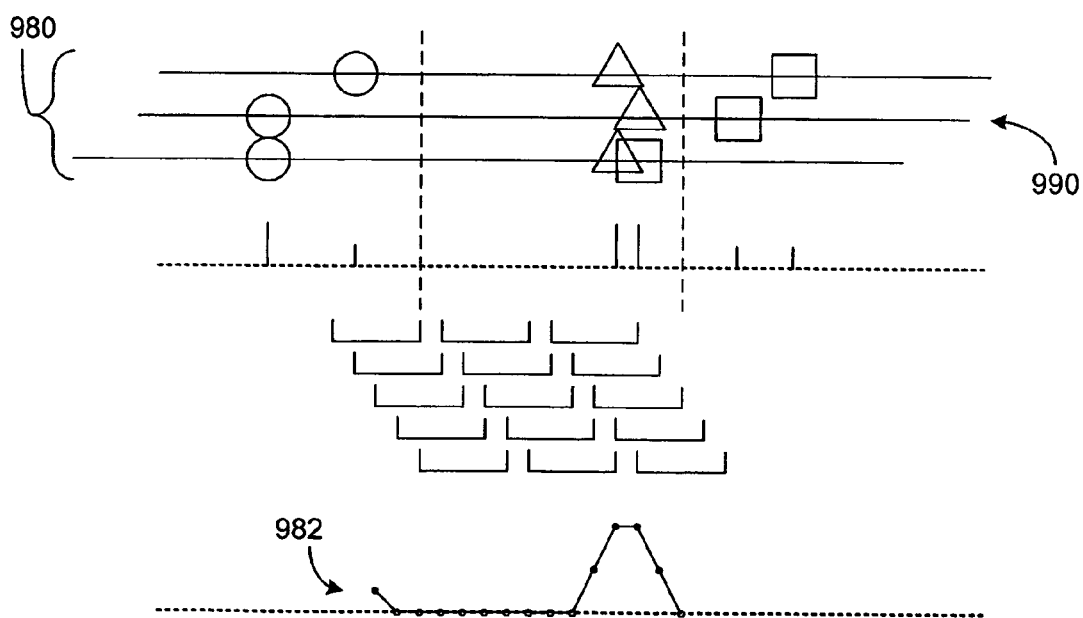

FIG. 34B shows a shifted data trace set 980 corresponding to "almost in focus" configuration. In particular, the combination 980 has the second trace (990 in FIG. 34B) not shifted as much as that of FIG. 34A. Average values 982 associated with the running average intervals are also shown.

In one embodiment, a best degree of focus can be determined by looking for the greatest change in the running average value. Thus in the example scanlines shown in FIGS. 34A and B, a change in average denoted as 974 has the greatest slope (i.e., the greatest "contrast") within the window. The data trace combination 840 corresponds to the greatest slope 974, and thus represents the "in focus" scanline having the best degree of focus value (in this example, the greatest slope).

In another embodiment, a best degree of focus can be determined by looking for the greatest sum of average values within the window. In FIGS. 34A and B, one can see that the average values 972 add up to a greater value than that of the average values 982. Thus, the data trace combination 840 can be said to be the "in focus" scanline having the best degree of focus value (in this example, the sum of average values).

One can see that there are many other ways of determining the best degree of focus. Thus, it will be understood that the two examples described above in reference to FIGS. 34A and B are not to be construed as limiting the scope of the present teachings. Furthermore, "quality value" can represent the various degrees of focus described herein, and "best quality value" can represent the corresponding "best degree of focus." It will be understood that the term "best" does not necessarily mean a value having the largest value. It can mean a value having the smallest value, or any value that represents a particular combination having the desired property for the purpose of assigning to a scanline.

Figure 35A:
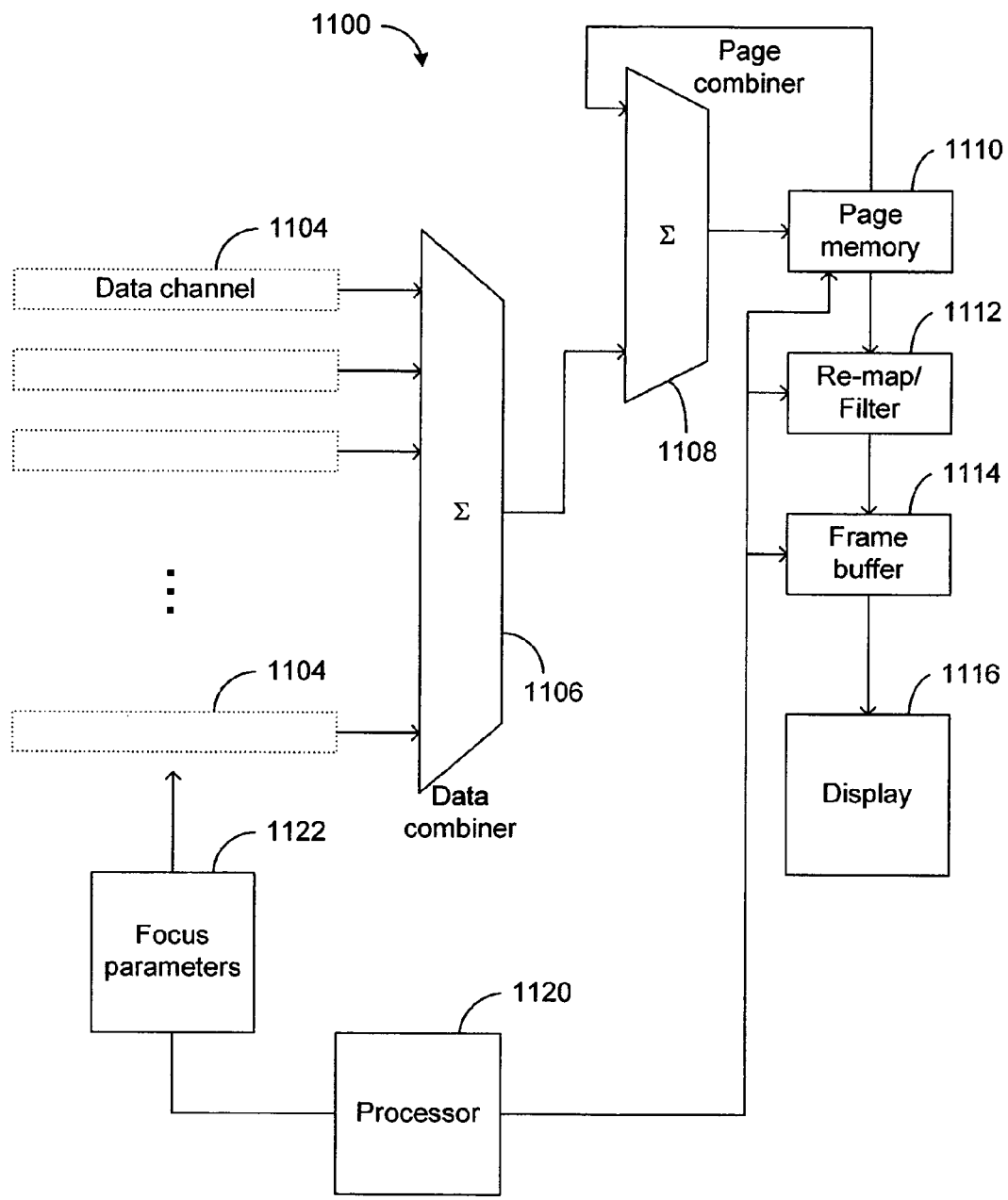
FIGS. 35A and B show by way of example one embodiment of a signal processing system that combines signals from the plurality of receivers.

FIGS. 35A and B now show block diagrams of one embodiment of a signal processing assembly 1100 that can perform various functions described herein (such as obtaining data traces from receivers, digitally sampling, and combining the digitally sampled data). As shown in FIG. 35A, one embodiment of the assembly 1100 includes a plurality of data channels 1104 that are input into a data combiner 1106. Each data channel 1104 forms a stream of digital data corresponding to data traces from one or more receivers in a manner described below in greater detail. Thus in one embodiment, such digital data represents digital echo signals having amplitudes and time information of samplings of the data traces.

As shown in FIG. 35A, such digital data from the data channels 1104 are combined by a data combiner 1106. In one embodiment, the data combiner 1106 combines the digital data according to the relative orientation of the receivers with respect to transmitters. For example, data corresponding to offset-one receivers can be combined as one set of data. In one embodiment, such combining of data is performed by parallel processing (as depicted in FIG. 35A) so as to allow timely processing of relatively large amount of data.

In one embodiment, each stream of data in the channel 1104 is associated with a receiver and a transmitter. Thus, focus information can be associated with such receiver and/or transmitter and can be provided to the channel 1104 by a focus parameter database 1122. For example, for pixel imaging, the focus information can include the transmitter and receiver alignment sets. For focusing on a layer along a scanline, the focus information can include a default velocity information for the receivers.

Thus in one embodiment, an output from the data combiner 1106 represents group(s) of data corresponding to different receiver-transmitter combinations. As shown in FIG. 35A, such combined data can form a "page" of data, and such pages of data can be further combined by a page combiner 1108. For example, pixel intensity as determined by selected groups of transmitter-receiver combinations (pages) can be further combined to enhance the real signal from that pixel, by using the transmitter-pixel and pixel-receiver geometries. In another example, pages of data can be combined with respect to a scanline for a receiver at a given layer, such that each combination yields a degree of focus or a quality value. As described above, a "best" degree of focus or quality value can be determined in a number of ways to select a "best" scanline for the receiver.

As shown in FIG. 35A, an output from the page combiner 1108 can be stored in a page memory 1110. Such stored page combinations can be refined further as shown. For example, the finer focusing by layer-splitting described above can be facilitated by such a feature.

In one embodiment, the page memory 1110 can include a plurality of "final" pages of data that can be used for imaging. As shown in FIG. 35A, such pages of data can be processed further to clean up the data and/or mapped to a display representation in a re-map/filter block 1112. Output from the block 1112 can be built into a frame of an image in a frame buffer 1114, and be displayed via a display 1116.

Figure 35B:
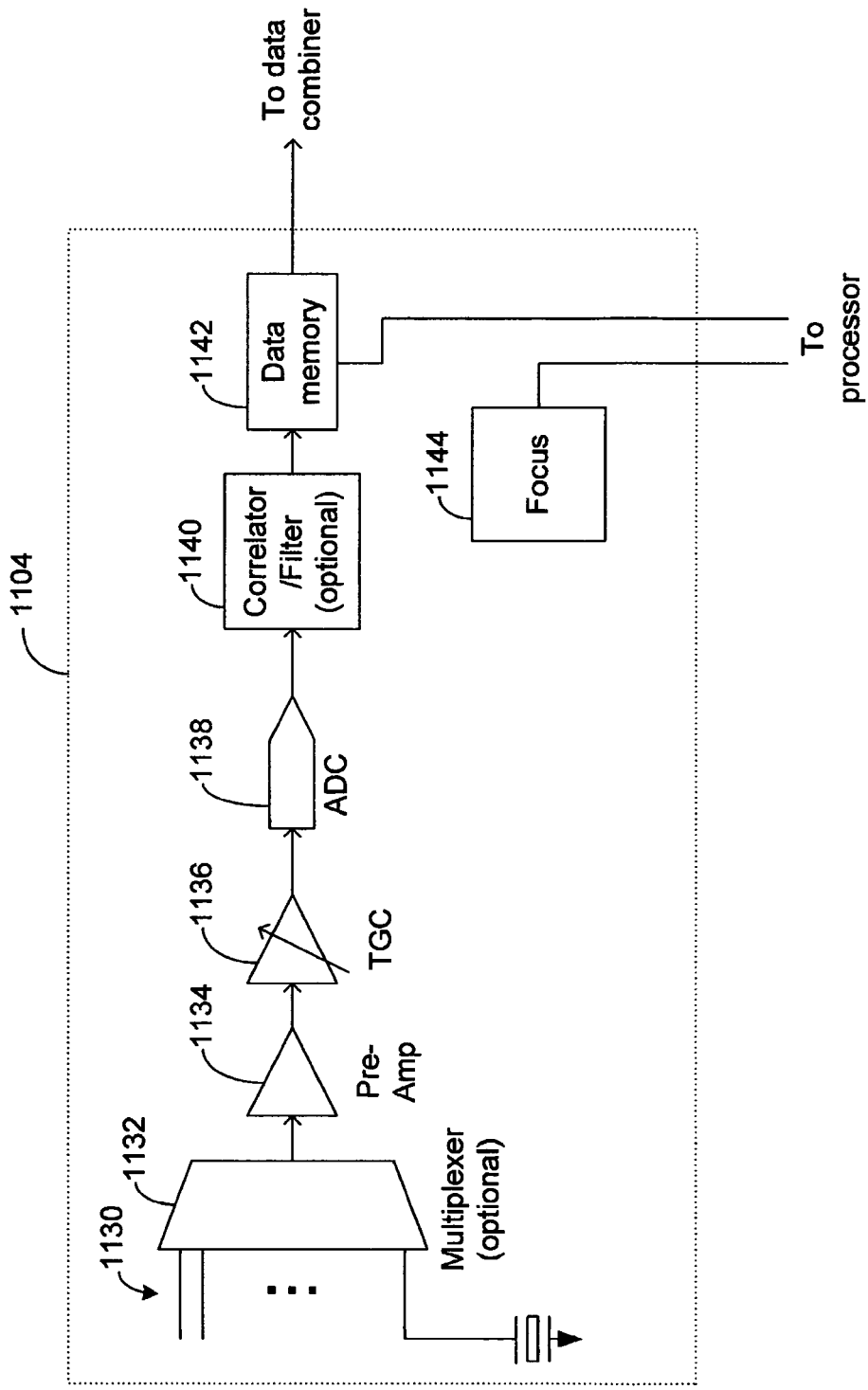

FIG. 35B now shows one embodiment of the data channel 1104 described above in reference to FIG. 35A. The data channel 1104 is shown to include an optional multiplexer 1132 that receives as inputs 1130 analog data traces from a plurality of receivers (not shown). In one embodiment, the multiplexer is not used, and data trace from one receiver is input into one data channel.

As shown in FIG. 35B, the multiplexer output (or signal from the receiver) can be amplified by a pre-amp 1134 and have its temporal gain corrected by a TGC 1136. The output from the TGC 1136 is shown to be digitally sampled by an ADC 1138 (analog-digital converter). In one embodiment, the ADC 1138 is a 12- or 16-bit amplitude ADC that samples the amplitude of the data trace at a sampling frequency.

As shown in FIG. 35B, the output from the ADC 1140 can be cleaned up and/or formatted for subsequent processing by an optional correlator/filter 1140. The output from the correlator/filter 1140 is input into a data memory 1142 for combining with the focus information from a focus database 1144 as described above in reference to FIG. 35A. The output from the data memory 1142 is then sent to the data combiner (1106 in FIG. 35A).

One can see that foregoing example signal and data processing, such as combining of different pages of data to determine the best scanline for a given receiver, can involve a substantially large amount of computation. Timely computation of such a task can be achieved, in one embodiment, by parallel processing.

One can also reduce the amount of computation in combining of data by limiting the combinations to a selected window in time. For example, suppose each digital echo data has N samples so as to represent a sampling duration of T. As described above, one way to form an image of a scanline is to focus onto a layer that intersects with the scanline. Such a layer with a given thickness is positioned from the receiver in a known manner. Thus one can estimate the approximate time values associated with the layer based on its relative position and its thickness by knowing the average propagation velocity of the echo signal in the medium. So to image the scanline for that layer, one can limit the digital echo data to a range that corresponds to the layer thickness.

Figure 36A:
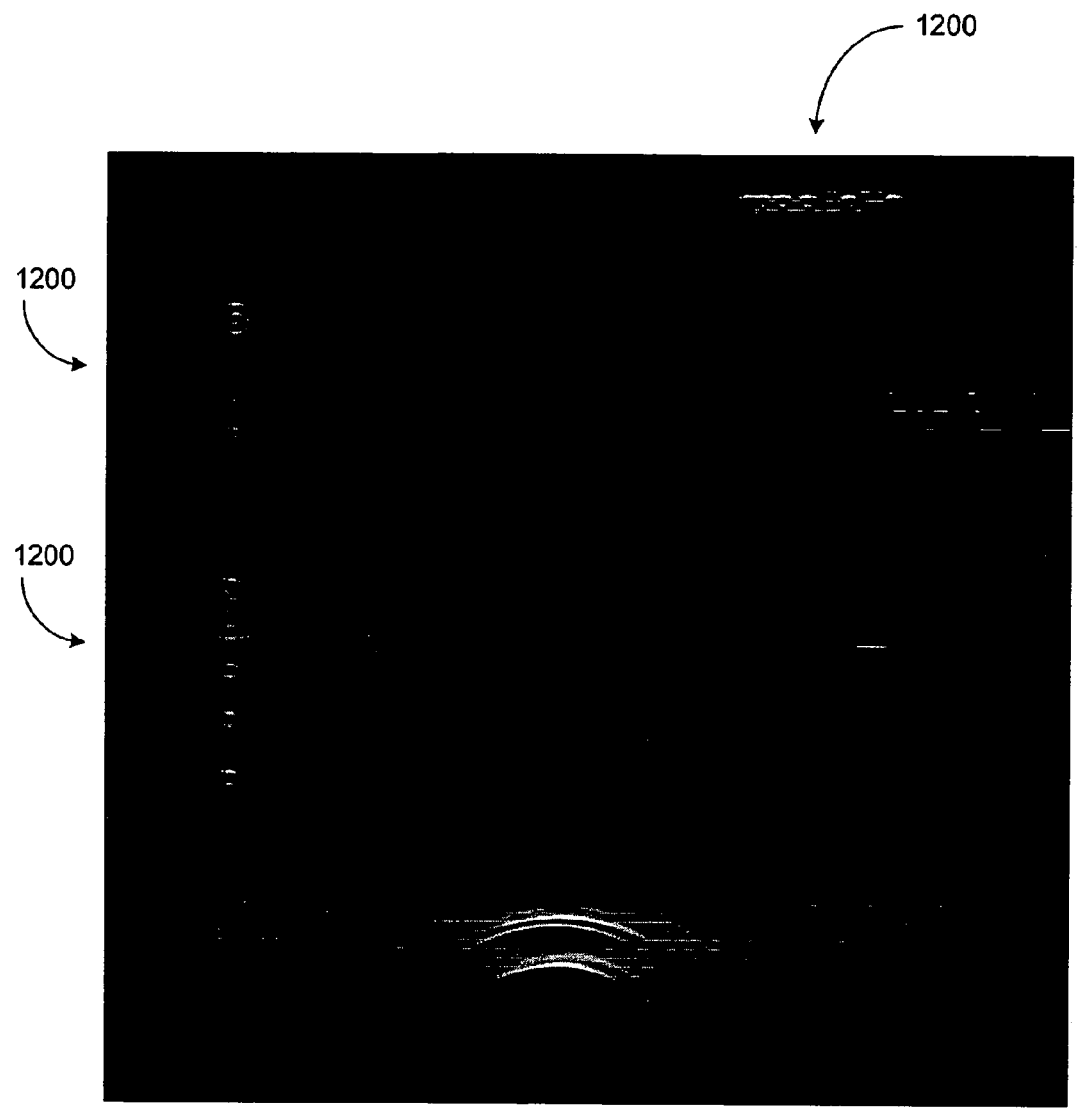
FIG. 36A shows a photograph of an example of an actual image obtained using multiple receivers and by combining signals therefrom in a manner described herein.
Figure 36B:
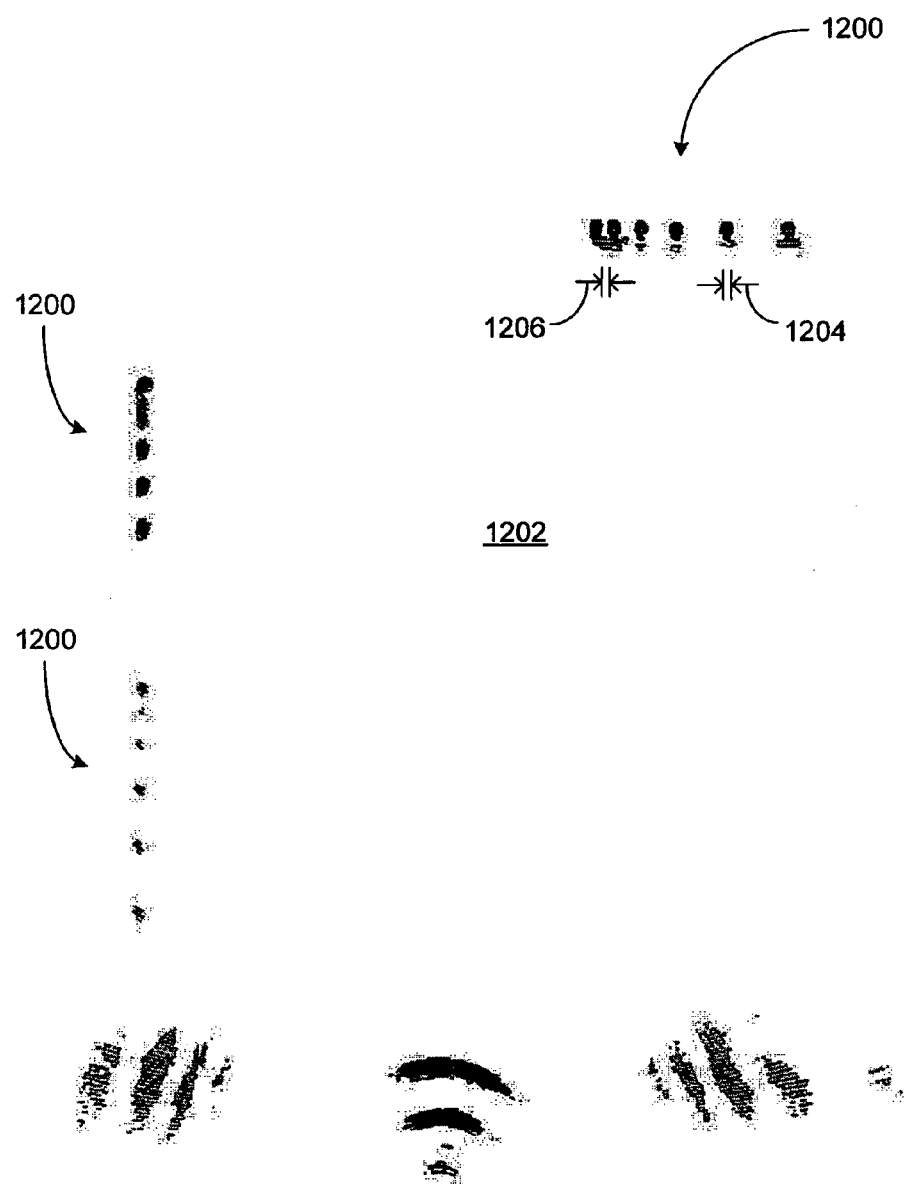
FIG. 36B shows a negative image of the photograph of FIG. 36A.

FIGS. 36A and B now show an example image obtained using some of the imaging methods described herein. FIG. 36A shows a black-and-white photograph of the image. FIG. 36B shows a negative image of the photograph of FIG. 36A. A sectional view of a plurality of wires 1200 is formed by imaging a slice through a medium 1202 where the wires are located. Each wire has a diameter (denoted as 1204) of approximately 100 micrometers, and a spacing (denoted as 1206) between (edge-to-edge) two closest adjacent wires is approximately 100 micrometers. The medium 1202 is water contained in a volume of approximately 350 $cm^3$, and the wires are located approximately 6.7 cm from an array of receivers (not shown).

To obtain such an image, 32 receivers were used to receive echo signals that resulted from sequenced transmission energy from 32 transmitters. The transmission energy was transmitted at approximately 3.5 MHz, and the echo signals detected by the receivers were sampled at a rate of approximately 20 MHz.

One can readily see from FIGS. 36A and B that the resulting high quality and contrast image displays a spatial resolution that appears to be better than 100 micrometers. For the example transmitted 3.5 MHz signal, a corresponding wavelength in water is approximately 440 micrometers (for an average velocity of 1540 m/s). Thus, one can see that resolving of a 100 micrometers feature at the transmitted energy frequency of 3.5 MHz is equivalent to a resolution being better than quarter of the operating wavelength.

In terms of Nyquist sampling criteria, the example 3.5 MHz signal would require sampling at a rate of approximately 7 MHz (twice the signal frequency) or higher for conventional devices. In a similar token, measurement of an example feature size of 100 micrometers would require a sampling rate of approximately 30.8 MHz (twice the frequency that can be assigned to a 100-micrometer feature size—i.e., 1540 [m/s]/100 [micrometers]=15.4 MHz) for conventional devices. Thus, one can see that sampling at multiple receivers and combining data therefrom can yield a high-quality result even if the sampling rate (example, 20 MHz) is less than the conventional Nyquist limit (example, 30.8 MHz).

From the description of the example image and the methods used herein, it is apparent that one can obtain a spatial resolution that is less than the wavelength associated with an operating transmission energy. Intrinsic resolution of a detector is often expressed in terms of $\lambda/D$, a ratio of the operating wavelength $\lambda$ and the effective aperture size D of the detector. A constant factor associated with such a ratio can vary depending on the configuration of a particular detector. For the purpose of description herein, it will be assumed that the intrinsic angular resolution is represented as $\theta=\lambda/D$.

One can reduce the value of $\theta$ (i.e., increase or "better" the resolution) by either reducing the wavelength and/or increasing the detector size D. The effective size D of the detector can be increased either by increasing the individual detector size, or by forming an array whose overall size can be substantially larger than that of each detector. Such methods have been used in some fields. In the field of ultrasound imaging, Applicant believes that currently, the image quality and resolution as disclosed herein has not been achieved using conventional systems and methods. For example, one embodiment of the imaging system and method yields an angular resolution that is equivalent to using a wavelength that is less than a quarter of the operating wavelength for a given detector size D. That is, the resolution is better than $\theta=(0.25)\lambda/D$ in one embodiment.

From the description herein it is also apparent that the sampling frequency can be less than the frequencies associated with perturbation features that "ride" on the "carrier-wave" echo of the transmission energy. One way to characterize such performance is by way of Nyquist criteria that essentially states that a signal needs to be sampled at a frequency F that is at least twice the frequency of the signal to obtain any useful information. Thus for example, if a signal has a frequency of 1 MHz, it needs to be sampled at 2 MHz or higher.

If the sampling frequency is less than twice the signal frequency, an effect known as "aliasing" occurs, where frequencies above the Nyquist frequency (F/2) "fold over" to behave like lower frequencies. As is known, aliased frequency f in the range F/2 to F becomes f' that can be expressed as |f−F|.

From the description herein, it is apparent that in one embodiment (that produces the example image of FIGS. 36A and B, for example), the sampling frequency can be less than twice the frequency associated with the size feature of interest. For example, the feature size of the wires in FIGS. 36A and B is approximately 100 micrometers, and its corresponding "frequency" can be represented as approximately (1540 m/s)/(100 micrometers)=15.4 MHz. From the results obtained by sampling at approximately 20 MHz (which is less than twice the frequency corresponding to the feature size), one can see that such relatively small perturbation features can be imaged with excellent quality and resolution.

It should be noted that for the purpose of description, the term "frequency" means the frequency associated with the central peak associated with the signal. Thus, if the signal is a sinusoidal wave, its frequency corresponds to the standard meaning. If the signal is a pulse (e.g., Gaussian shaped), then the frequency corresponds to the central peak of the pulse. If the signal is a perturbation feature having a peak structure, then the frequency corresponds to that peak.

With such example definition of frequency, one can characterize the performance of the present teachings as being able to image an echo signal in terms of spectral frequency components. If a given echo signal has a maximum intensity value, then the resolvable spectral frequency components above the Nyquist frequency of F/2 can include higher frequency components having intensities that are above a predetermined value. Such a predetermined value can be set at different values, such as 50 dB, 40 dB, 30 dB, 20 dB, 10 dB, or 5 dB less than the maximum intensity value of the echo signals.

FIGS. 37-42 show an example of an operating principle that could explain why the various techniques of the present disclosure can yield relatively high resolution images (for example, images shown in FIGS. 36A and 36B). FIG. 37 shows an example detectable analog signal 1302 having various fine features. Some of the fine features are noise, and some may be signal(s) of interest that result from interaction of the acoustic energy with one or more objects in the medium. In general, whether a given feature is noise or signal of interest is not known in advance. For the purpose of description, however, a feature 1306 will be assumed to be a signal feature of interest, and the rest of the features on the example signal 1302 will be assumed to be noise. Also, for the purpose of providing a visual reference, an example carrier signal 1304 is superimposed with the signal 1302. Essentially, the signal 1302 includes the carrier signal combined with the various signal features, including the noise and the example signal feature of interest 1306.

As further shown in FIG. 37, the analog signal 1302 is shown to be sampled periodically at example times t1 to t8. Solid dots at the intersections of the analog signal 1302 and the sampling times indicate the signal values at the sampling times.

FIG. 38 shows an example table of data 1310 that can be obtained from sampling of the analog signal at times t1 to t8. The first column represents the sampling time; the second column represents the signal value S; and the third column represents the digitized value D of the signal value S. Thus, for example, S5 represents the value of the signal 1302 at time t5, and D5 represents the digitized value obtained from sampling of the signal value S5.

In many applications, the signal values (for example, analog measurement values) are not obtained. Instead, the analog signal 1302 is digitally sampled at the sampling times.

FIG. 39 shows a plot 1320 of the example digitally sampled values (D1 to D8) at the sampling times t1 to t8. As one can see, it can be a challenge to be able to reconstruct the original detectable analog signal 1302 from the sample set 1302 of digitally sampled data. In fact, there can be introduction of ambiguities that may or may not be resolved.

Such challenges are faced routinely in the known field of digital signal processing. In general, a signal having a frequency $f_o$ is not reconstructable, without ambiguity, from digitally sampled data if the sampling frequency $f_s$ is less than twice the signal frequency $f_o$. If a signal contains various frequency components in a bandwidth B, then that signal is considered to be not reconstructable, without ambiguity, from digitally sampled data is the sampling frequency $f_s$ is less than twice the bandwidth B. Such a constraint generally imposes a minimum sampling frequency of $2f_0$ (or 2B) commonly referred to as a Nyquist frequency. An ambiguity that results from sampling at a frequency below the Nyquist frequency is generally referred to as "aliasing."

It is, however, possible to obtain a useful result even when the sampling frequency is less than the Nyquist frequency. In digital signal processing, sampling of bandpass signals is one example known situation where a sub-Nyquist sampling frequency can yield useful results. For example, aliasing can be avoided when the sampling frequency $f_s$ is in the range defined by $$\frac{2f_c - B}{m} \geq f_s \geq \frac{2f_c + B}{m+1},$$

where m is a positive integer, $f_c$ is the center frequency of the signal, $f_s$ is the sampling frequency, and B is the bandwidth of the bandpass signal. In one example where $f_c$=20 MHz, and B=5 MHz, the above aliasing-avoidance condition can be satisfied $f_s$=22.5, 17.5, or 11.25 MHz for m=1, 2, or 3. These example sampling frequencies are below the commonly-known "Nyquist frequency" of $2f_c$ (=40 MHz in this example); however, they are all above the Nyquist frequency defined in terms of the bandwidth (2B=10 MHz). Additional details about sub-Nyquist sampling and related topics can be found in commonly available textbooks such as "Understanding Digital Signal Processing," Richard G. Lyons, Prentice Hall PTR Publication.

However one defines what sub-Nyquist frequency is, resulting frequency spectrums of the sampling that avoided aliasing (for example, by sampling bandpass signals under certain conditions) have various gaps where frequency components do not exist. Such gaps can be on either or both sides of the frequency $f_s/2$ (that is, half of the sampling frequency) in the frequency space distribution. In some applications, such gaps, and even the use of bandpass signals to avoid aliasing, may be undesirable for various reasons.

As described herein, one or more embodiments of the present disclosure do not necessarily suffer from the constraints associated with techniques such as a bandpass filtering technique. As described above in reference to FIGS. 37-39, the sampled data, whether in the raw form S or the digitized form D, represent the values of the signal 1302 at the sampling times. There is, in general, no ambiguity with respect to the validity of such sampled data. It is known that an i-th data $D_i$ represents the value of the signal 1302 at time $t_i$. Given the data $D_i$, it is possible to reconstruct the portion of the signal 1302 at time $t_i$. As described above, ambiguities can arise when one attempts to reconstruct the entire signal 1302 from a group of such discrete data (for example, the digital data set 1320 of FIG. 39).

It should be understood that the example signal 1302 and the resulting example discrete data set 1320 are associated with a given detector. Thus, if a given system only has one detector, then the signal reconstructing capability is essentially constrained by the sampling frequency and other conventional digital signal processing parameters.

Figure 40:
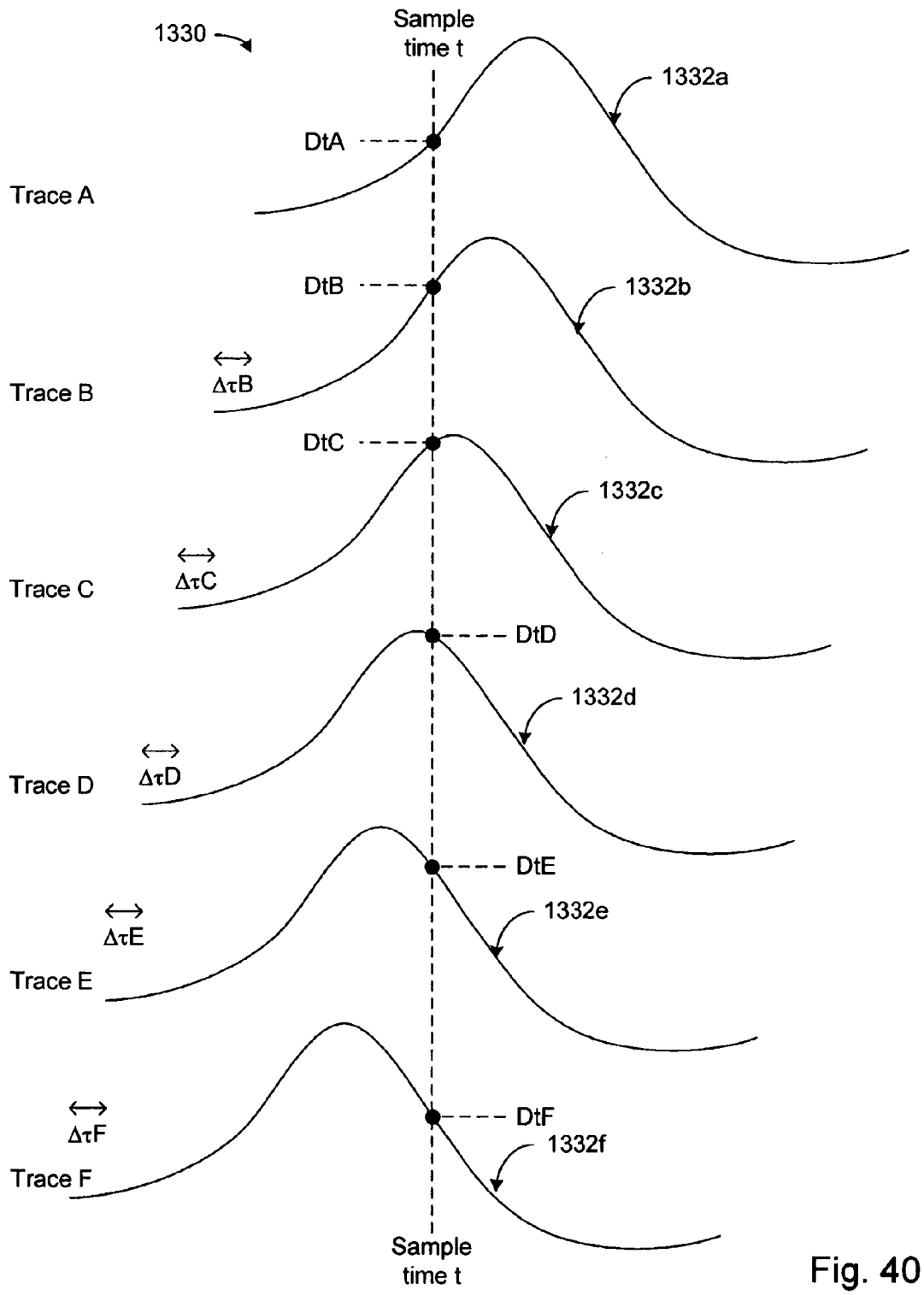
FIG. 40 shows an example of a relatively fine feature of the analog signal of FIG. 37 being sampled at different phases via various example detectors.

In one or more embodiments of the present disclosure, however, use of a plurality of detectors can allow improved characterization of a signal feature of interest without being constrained by aliasing concerns. FIG. 40 shows an example of a plurality of signal traces 1330 that can be obtained by use of a plurality of detectors. For the purpose of description, it will be understood that trace A is from detector A, and so on. Also for the purpose of description, only the signal feature of interest 1332 is depicted. In general, the signal feature of interest 1332 may vary when detected at different detectors. For example, the amplitude may decrease if the propagation distance increases. Also, the medium may vary for propagation paths to different detectors.

As further shown in FIG. 40, each of the example detectors A to F are shown to be sampled at time t. Thus, trace A from detector A yields a sampled value of DtA, trace B from detector B yields a sampled value of DtB, and so on.

As further shown in FIG. 40, the signals 1332 are shown to arrive at the detectors in succession. For example, the signal 1332b is shown to arrive at detector B after a delay of $\Delta \tau B$ from the arrival time of the signal 1332a at detector A. The signal 1332c is shown to arrive at detector C after a delay of $\Delta \tau C$ from the arrival time of the signal 1332b at detector B, and so on. Such delays in arrival times may result from the geometry of the arrangement of the detectors.

As described above, there is in general no ambiguity in the sampled data themselves. Thus, the sampled data DtA unambiguously represents the signal 1332a at time t. Similarly, the sampled data DtB unambiguously represents the signal 1332b at time t, and so on. One can thus see that the independently obtained data via different detectors unambiguously represent the signal 1332 at different phases of that signal 1332. If such signals are phase shifted and combined properly, the resulting sampled data representing the different phases can be essentially equivalent to sampling the signal at a higher frequency.

One or more embodiments of the present disclosure relate to combining a plurality of signal traces from a plurality of detectors so as to allow imaging of relatively fine features in a medium. For example, one embodiment of a method for combining digitally sampled data has been described above in reference to FIGS. 22 to 30.

Figure 41:
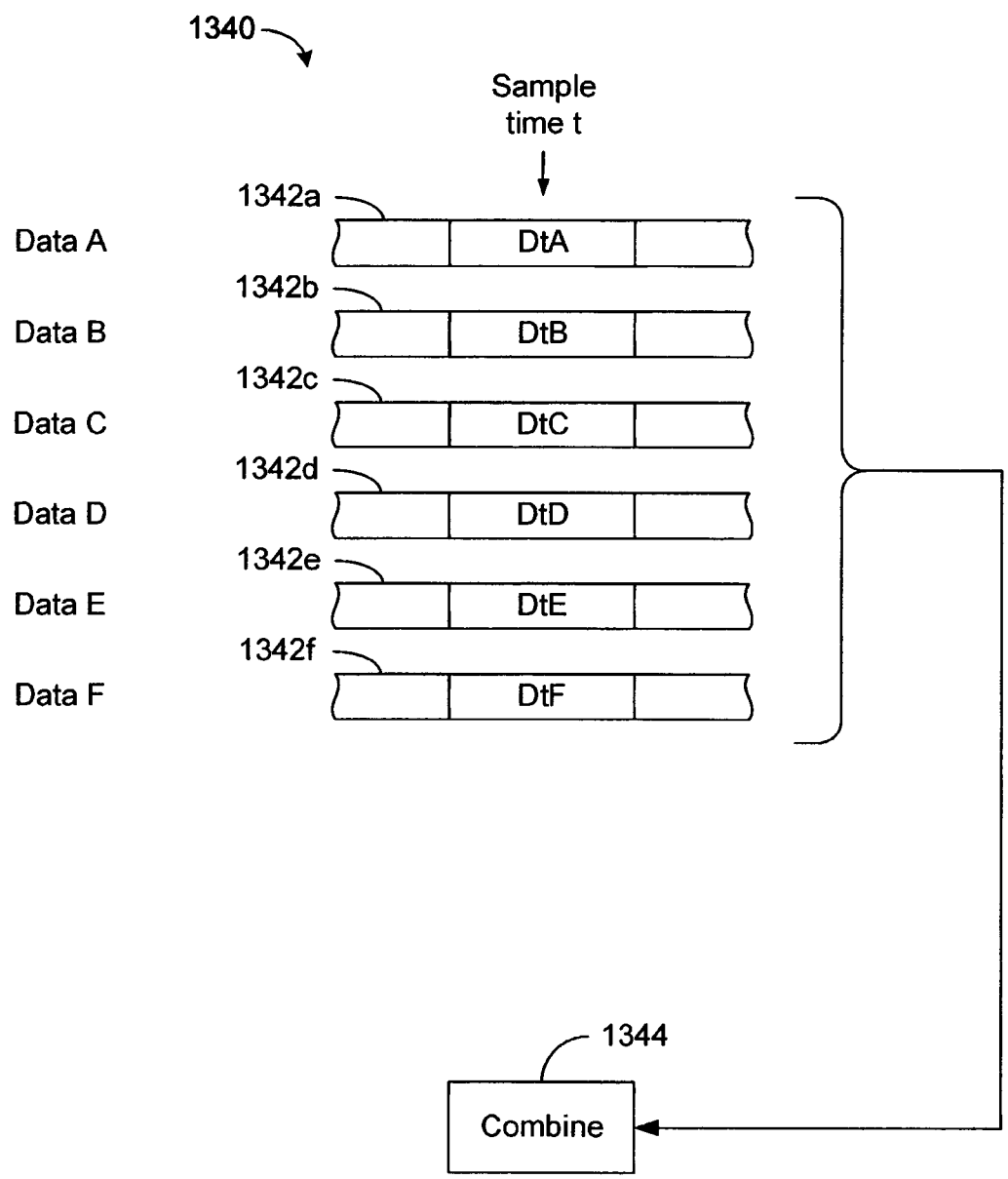
FIG. 41 shows an example of digitally sampled data corresponding to the example samplings via the example detectors.

In one embodiment, a similar combining technique 1340 may be applied to the example sampled data associated with the example traces A to F of FIG. 40. Thus, as shown in FIG. 41, a plurality of digital data sets A to F containing portions (DtA, DtB, etc.) are shown to be combined in a similar manner via a component 1344. As described above, such combining can yield an enhancement of the signal of interest while the noise components cancel substantially.

Figure 42:
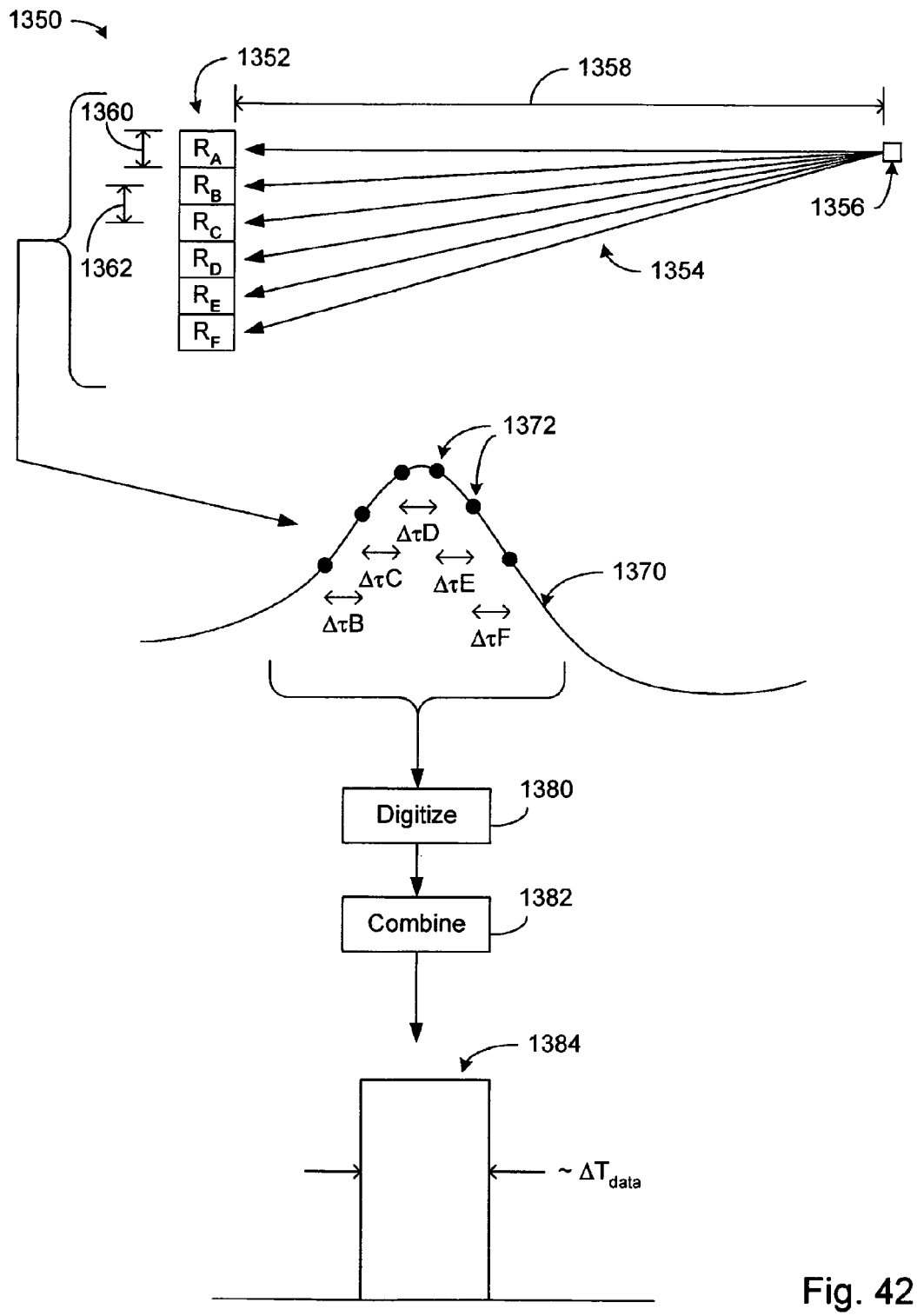
FIG. 42 shows how various parameters related to detection configuration and sampling configuration can determine an effective sampling frequency facilitated by phase-shifted samplings via a plurality of detectors.

FIG. 42 now shows an overview 1350 of the example process described above in reference to FIGS. 40 and 41. In one embodiment, the above-described delays in arrivals of signals 1354 can be facilitated by an orientation of an array of detectors 1352 with respect to a reflecting object 1356. In the example shown, the array 1352 is oriented so a line between the object 1356 and detector A is generally perpendicular to the array 1352. Thus, detector A is closest to the object 1356 in the example of FIG. 42. Distances from the object 1356 to detectors B to F are successively greater.

As further shown in FIG. 42, the differences in pathlengths to the different detectors can depend on factors such as distance 1358 from the array 1352 to the object 1356 and detector spacing 1362. The detector spacing can depend on the detector dimension (for example, when the detectors are closely packed).

As further shown in FIG. 42, the sampling of offset signal traces can yield a plurality of sampled values 1372 that can be equivalent to sampling of a signal 1370 at intervals determined by the arrival offsets (for example, due to pathlength differences). As described herein, one generally does not know that the sampled values belong to the same signal 1370. As also described herein, the sampled data 1372 can be digitized in a component 1380, and the digitized data can be combined in a component 1382 so as to yield a combined data 1384.

As further shown in FIG. 42, such combination of the digitized data can match data "packets" that correspond a given feature of interest. In one embodiment, a given data packet for a given signal trace can represent a sampling period. Thus, combining a plurality of such data packets can yield a combined packet representative of an average sampling period (that is, inverse of the sampling frequency) $\Delta T_{data}$.

Based on the foregoing, one can see that the resolution associated with the combined digital data can have a time resolution that depends on the sampling period. One can also see that the number of sampled data that can be combined into a given sampling period can depend on how phase separated the signal traces are at the detectors. As described above in reference to FIG. 42, phase separations can be affected by factors such as differences in the pathlengths to different detectors. One can also see that the quality and/or efficiency of the combined digital data can be affected by the number of detectors and/or the actual sampling interval. While a larger number of detectors and a smaller actual sampling interval may be desirable, one may need to balance such benefit with detector-imposed geometries and/or computing requirements.

As described herein, introduction of phase differences to a plurality of independent detectors, and independently sampling at those different phases can be generally equivalent to sampling a single signal at an effective sampling interval corresponding to the phase differences. The effective sampling interval can be affected (and sometimes selected) by factors such as a detector geometry with respect to a given reflecting object, medium, and/or the actual sampling frequency. These factors are introduced by independent sampling by a plurality of detectors, and are generally not constrained by the aliasing effect associated with sampling of a single signal.

Furthermore, the overall sampling resolution of the combined digital data can be selected based on the effective sampling interval and the number of detectors to combine, both of which can affect how many sampled digital data get combined into a given combined packet.

When one considers the foregoing, it is apparent that the overall sampling resolution and the corresponding spatial resolution depend on factors that are generally not affected by aliasing. Consequently, it is believed that the present disclosure allows sampling of analog echo signals having substantial frequency components (for example, noise and/or features of interest) in essentially any range. In one embodiment, such a range includes frequency components from (and including) zero to F/2, where F is the actual sampling frequency for sampling of the analog echo signal; and from (and including) F/2 and higher. Such sampling can produce corresponding digital echo signals, and such digital signals can be combined so as to yield an image having a relatively high resolution.

In one embodiment, the foregoing examples of combining sampled analog echo signals can be considered as substantially negating the effects of aliasing within at least the sampled analog echo signals. That is, without such combining of the sampled analog echo signals, reconstruction of analog signals would be subject to aliasing effects, and thus be subject to constraints of certain range(s) of sampling frequency(ies).

Figure 43:
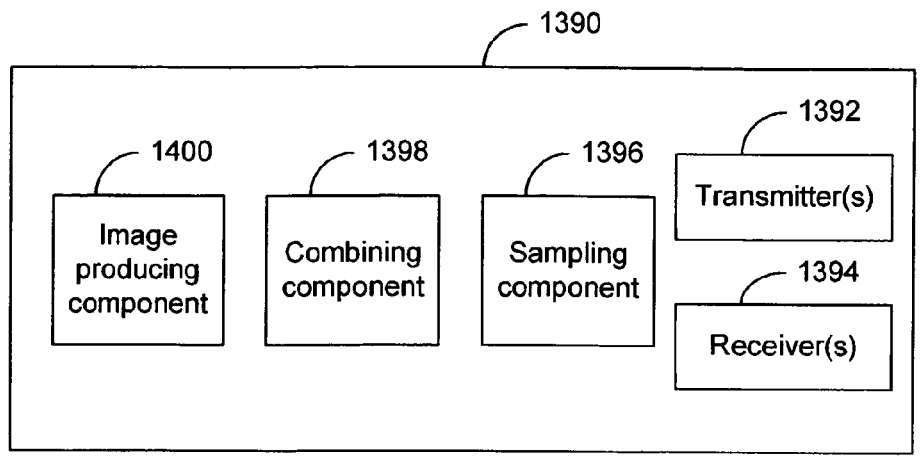
FIG. 43 shows a block diagram of one embodiment of an apparatus having a sampling component and a combining component that allows detection and imaging of analog echo signals resulting from relatively fine features in a medium.

FIG. 43 shows that in one embodiment, various techniques that facilitate production of relatively high resolution images can be implemented in a system 1390 having different components or modules. For example, the system 1390 can have a transmitter component 1392, a receiver component 1394, a sampling component 1396, a combining component 1398, and/or an image producing component 1400. Each, some, or all of these example components or modules may represent a physical device, a process, or any combination thereof. Moreover, a given component or a module can represent one or more devices, one or more processes, or any combination thereof, such that the given component achieves or facilitates a given functionality of the system 1390.

For example, the sampling component or module 1396 can include one or more devices, one or more processes, or any combination thereof, such that the component 1396 facilitates digital sampling of one or more analog echo signals. In one embodiment, the sampling component 1396 includes an analog-to-digital converter (ADC). In one embodiment, a plurality of ADCs can be associated with respective plurality of analog echo signals from a plurality of receivers. In one embodiment, the sampling component or module 1396 may provide a functionality of digital sampling of a plurality of analog echo signals. In one embodiment, the sampling component 1396 includes a processor. In some embodiments, the sampling component 1396 can include devices or components such as, but not limited to, one or more computers, one or more of various types of filters that facilitate processing of signals, one or more ADCs, and/or one or more devices such as sigma-delta converters.

Similarly, the combining component or module 1398 can include one or more devices, one or more processes, or any combination thereof, such that the component 1398 facilitates combining of a plurality of digital echo signals. In one embodiment, the combining component 1398 includes a processor.

Figure 44A:
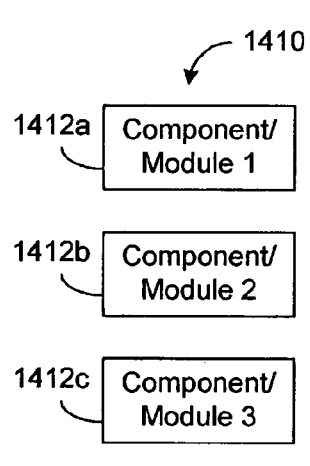
FIGS. 44A-44C show by examples various ways modules or components can be configured in various embodiments of the present teachings.
Figure 44B:
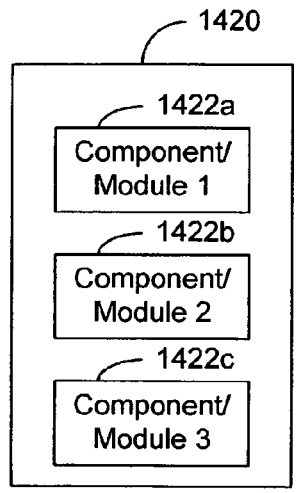
Figure 44C:
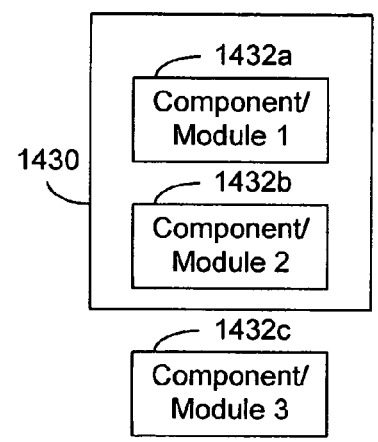

In general, as shown in FIGS. 44A-44C, modules or components described herein can be separate units and/or processes, be part of a same unit and/or process, or any combination thereof. For example, as shown in FIG. 44A, example modules 1410 are depicted as including separate modules 1412a-c, where each module can be configured to perform certain function(s) so as to achieve a desired functionality overall. As shown in FIG. 44B, an example modules 1422a-c are depicted as being parts of a unit or process 1420, such that the unit or process 1420 can be configured to perform different functions via the example modules 1422a-c so as to achieve a desired functionality overall. As shown in FIG. 44C, example modules 1432a and b are depicted as being parts of a unit or process 1430, such that the unit or process 1430 can be configured to perform different functions via the example modules 1332a and b. The functionality of the unit or process 1430 can be combined with a functionality of a separate example module 1432c, so as to achieve a desired functionality overall.

Figure 45A:
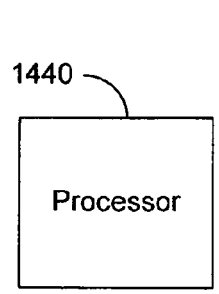
FIGS. 45A and 45B show by examples various ways a processor can be configured in various embodiments of the present teachings.
Figure 45B:
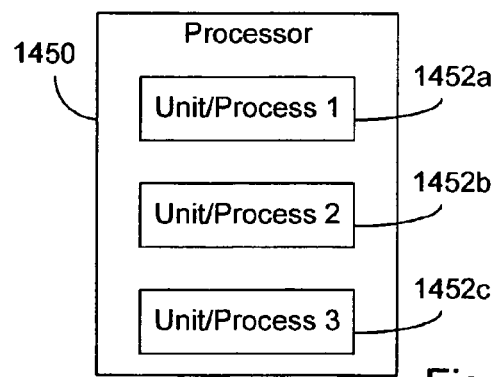

FIGS. 45A and 45B show how such different example configurations can be applied to processors that are configured to facilitate various processes as described herein. In some embodiments, as shown in FIG. 45A, a processor 1440 can be configured to perform or facilitate performance of one or more processes. In one embodiment, the example processor 1440 can be incorporated into a single unit.

In some embodiments, as shown in FIG. 45B, a processor 1450 may include a plurality of units 1452 that are configured to provide certain functionalities, such that some combination of such individual functionalities provides one or more functionalities of the processor 1450. In one embodiment, the example processor 1450 includes a plurality of separate units.

In some embodiments, the example configurations of FIGS. 45A and 45B can be combined in any manner. For example, a processor functionality may be provided by one or more first processors that are similar to that described above in reference to FIG. 45A, and one or more second processors that are similar to that described above in reference to FIG. 45B.

Any of the foregoing techniques, either individually or in any combination, may be used for medical or non-medical purposes. Moreover, in some embodiments, various means for providing various functionalities described herein can be achieved by various modules or components also described herein. For example, FIGS. 43-45 show various examples of modules or components that can be configured to perform various techniques of the present disclosure.

Although the above-disclosed embodiments have shown, described, and pointed out the fundamental novel features of the invention as applied to the above-disclosed embodiments, it should be understood that various omissions, substitutions, and changes in the form of the detail of the devices, systems, and/or methods shown may be made by those skilled in the art without departing from the scope of the invention. Consequently, the scope of the invention should not be limited to the foregoing description, but should be defined by the appended claims.

What is claimed is:

1. An ultrasound imaging apparatus, comprising:
   a plurality of transmitters configured to transmit acoustic energy to an object in a medium such that said acoustic energy becomes scattered;
   a plurality of receivers configured to receive said scattered energy and in response produce respective analog echo signals, each of said analog signals comprising substantial spectral frequency components above a frequency F/2 and comprising substantial nonnegative spectral frequency components below or at said frequency of F/2;
   a sampling module configured to sample said analog echo signals at a frequency of F, said sampling producing a respective plurality of digital echo signals;
   a combining module configured to combine said plurality of digital echo signals, each of said digital echo signals being offset by time with respect to another of said digital echo signals, so as to produce a combined digital signal comprising a sequence of samples having a sample frequency exceeding F; and
   an image producing module configured to produce an image pixel of said object based at least in part on said combined digital signal.

2. The apparatus of claim 1, wherein the image producing module is configured to produce a plurality of image pixels, wherein said plurality of image pixels are produced from a plurality of combined digital signals, different ones of the combined digital signals comprising samples from different combinations of said plurality of digital echo signals, said plurality of combined digital signals each having a sampling frequency exceeding F.

3. The apparatus of claim 1, wherein the combining module is configured to combine said plurality of digital echo signals by a process that comprises:
 selecting a first digital echo signal associated with a first receiver; and
 performing a plurality of time-shift combinations of the first digital echo signal with one or more digital echo signals associated with one or more other receivers about a selected time window of the first signal, wherein each of said plurality of combinations has a quality value indicative of a quality of said combination.

4. The apparatus of claim 3, wherein said process further comprises assigning one of said plurality of combinations having a particular quality value to a scanline for said first receiver.

5. The apparatus of claim 4, wherein said selected time window corresponds to a layer having a first thickness along said scanline.

6. The apparatus of claim 5, wherein said particular quality value comprises a running average of an amplitude of said one of said plurality of combinations.

7. The apparatus of claim 5, wherein said particular quality value comprises a slope of a running average of an amplitude with respect to time of said one of said plurality of combinations.

8. The apparatus of claim 5, wherein said process further comprises:
 splitting a parent layer into two or more sublayers;
 performing time-shift combinations on each of said sublayers;
 determining a best quality value for each of said sublayers;
 comparing a best quality value of said parent layer to said best quality value of each of said sublayers;
 if said best quality value of said parent layer is substantially less than said best quality value of each of said sublayers, then continuing to divide each of said sublayers into final sublayers, wherein each of the best quality values of said final sublayers is less than the best quality value of a parent layer of said final sublayers.

9. The apparatus of claim 8, wherein said process further comprises assigning a combined digital signal of said parent layer of said final sublayers to the scanline.

10. The apparatus of claim 5, wherein the scanline is divided into a plurality of layers, and wherein determinations of the particular qualities of said combinations are performed successively starting from a layer closest to the receiver.

11. The apparatus of claim 1, wherein the combining module is configured to combine the plurality of digital echo signals in a manner that substantially negates the effects of aliasing within at least the sampled analog echo signals.

12. A method of imaging an object in a medium with ultrasound, the method comprising:
 transmitting acoustic energy from a transmitter to the object such that said acoustic energy becomes scattered;
 receiving said scattered energy at a plurality of receivers so as to produce respective analog echo signals, each of said analog signals comprising substantial spectral frequency components above a frequency F/2 and comprising substantial nonnegative spectral frequency components below or at said frequency of F/2;
 sampling said analog echo signals at a frequency of F, said sampling producing a respective plurality of digital echo signals;
 combining said plurality of digital echo signals, each of said digital echo signals being offset by time with respect to another of said digital echo signals, so as to produce a combined digital signal comprising a sequence of samples having a sample frequency exceeding F; and
 producing an image pixel of said object from said combined digital signal.

13. The method of claim 12 further comprising producing a plurality of image pixels wherein said plurality of image pixels are produced from a plurality of different combined digital signals, the different combined digital signals comprising samples from different combinations of said plurality of digital echo signals.

14. The method of claim 13, wherein said substantial spectral frequency components above a frequency of F/2 comprise a higher frequency component having an intensity that is above a predetermined value.

15. The method of claim 14, wherein said predetermined value is set relative to a maximum intensity of the spectral frequency components of one of said sampled analog echo signals.

16. The method of claim 13, wherein combining said plurality of digital echo signals comprises:
 selecting a first digital echo signal associated with a first receiver;
 performing a plurality of time-shift combinations of the first digital echo signal with one or more digital echo signals associated with one or more other receivers about a selected time window of the first signal, wherein each of said plurality of combinations has a quality value indicative of a quality of said combination.

17. The method of claim 16, further comprising assigning one of said plurality of combinations having a particular quality value to a scanline for said first receiver based at least in part on said quality value.

18. The method of claim 17, wherein said selected time window corresponds to a layer having a first thickness along said scanline.

19. The method of claim 18, wherein said particular quality value comprises a running average of an amplitude of said one of said plurality of combinations.

20. The method of claim 18, wherein said particular quality value comprises a slope of a running average of an amplitude with respect to time of said one of said plurality of combinations.

21. The method of claim 18, further comprising:
 splitting a parent layer into two or more sublayers;
 performing time-shift combinations on each of said sublayers;
 determining a best quality value for each of said sublayers;
 comparing a best quality value of said parent layer to said best quality value of each of said sublayers;
 if said best quality value of said parent layer is substantially less than said best quality value of each of said sublayers, then continuing to divide each of said sublayers into final sublayers, wherein each of the best quality values of said final sublayers is less than the best quality value of a parent layer of said final sublayers.

22. The method of claim 21, further comprising assigning a combined digital signal of said parent layer of said final sublayers to the scanline.

23. The method of claim 18, wherein the scanline is divided into a plurality of layers, and wherein determinations of the particular qualities of said combinations are performed successively starting from a layer closest to the receiver.

24. The method of claim 13, wherein combining of the plurality of digital echo signals substantially negates the effects of aliasing within at least the sampled analog echo signals.

25. An ultrasound imaging apparatus, comprising:
a sampling module configured to sample, at a frequency of F, a plurality of analog echo signals received from a respective plurality of receivers, each of said analog echo signals comprising substantial spectral frequency components above a frequency of F/2 and comprising substantial nonnegative spectral frequency components below or at said frequency of F/2, said sampling producing a respective plurality of digital echo signals;
a combining module configured to combine said plurality of digital echo signals, each of said digital echo signals being offset by time with respect to another of said digital echo signals, so as to produce a combined digital signal comprising a sequence of samples having a sample frequency exceeding F; and
an image-producing module configured to produce an image pixel of an object from said combined digital signal.

26. An ultrasound imaging apparatus, comprising:
a plurality of sampling modules, each configured to sample, at a frequency of F, an analog echo signal received from a receiver, each of said analog echo signals comprising substantial spectral frequency components above a frequency of F/2 and comprising substantial nonnegative spectral frequency components below or at said frequency of F/2, said plurality of sampling modules producing a respective plurality of digital echo signals;
a combining module configured to combine said plurality of digital echo signals, each of said digital echo signals being offset by time with respect to another of said digital echo signals, so as to produce a combined digital signal comprising a sequence of samples having a sample frequency exceeding F; and
an image-producing module configured to produce an image pixel of an object from said combined digital signal.

27. An ultrasound imaging apparatus, comprising:
a plurality of means for sampling, each means for sampling configured to sample, at a frequency of F, an analog echo signal received from a receiver, each of said analog echo signals comprising substantial spectral frequency components above a frequency of F/2 and comprising substantial nonnegative spectral frequency components below or at said frequency of F/2, said plurality of means for sampling producing a respective plurality of digital echo signals;
means for combining said plurality of digital echo signals, each of said digital echo signals being offset by time with respect to another of said digital echo signals, so as to produce a combined digital signal comprising a sequence of samples having a sample frequency exceeding F; and
means for producing an image pixel of an object from said combined digital signal.

28. An ultrasound imaging apparatus, comprising:
a plurality of transmitters configured to transmit acoustic energy to an object in a medium such that said acoustic energy becomes scattered;
a plurality of receivers configured to receive said scattered energy and in response produce respective analog echo signals, each of said analog signals comprising substantial spectral frequency components above a frequency F/2 and comprising substantial nonnegative spectral frequency components below or at said frequency of F/2;
a plurality of sampling modules, each configured to sample, at a frequency of F, a corresponding one of said plurality of analog echo signals, said plurality of sampling modules producing a respective plurality of digital echo signals;
a combining module configured to combine said plurality of digital echo signals, each of said digital echo signals being offset by time with respect to another of said digital echo signals, so as to produce a combined digital signal comprising a sequence of samples having a sample frequency exceeding F; and
an image producing module configured to produce an image pixel of said object from said combined digital signal.

\* \* \* \* \*